US010100111B2

(12) United States Patent
Borras et al.

(10) Patent No.: US 10,100,111 B2
(45) Date of Patent: Oct. 16, 2018

(54) STABLE AND SOLUBLE ANTIBODIES INHIBITING TNF ALPHA

(71) Applicant: ESBATech, an Alcon Biomedical Research Unit LLC, Schlieren (CH)

(72) Inventors: Leonardo Borras, Schlieren (CH); Tea Gunde, Zurich (CH); David Urech, Hombrechtikon (CH)

(73) Assignee: ESBATech, an Alcon Biomedical Research Unit LLC, Schlieren (CH)

( * ) Notice: Subject to any disclaimer, the term of this patent is extended or adjusted under 35 U.S.C. 154(b) by 0 days.

(21) Appl. No.: 15/157,641

(22) Filed: May 18, 2016

(65) Prior Publication Data

US 2016/0251428 A1 Sep. 1, 2016

Related U.S. Application Data

(62) Division of application No. 14/134,779, filed on Dec. 19, 2013, now Pat. No. 9,422,366, which is a division of application No. 13/000,345, filed as application No. PCT/CH2009/000219 on Jun. 25, 2009, now Pat. No. 8,673,310.

(60) Provisional application No. 61/075,640, filed on Jun. 25, 2008, provisional application No. 61/155,041, filed on Feb. 24, 2009, provisional application No. 61/075,692, filed on Jun. 25, 2008, provisional application No. 61/075,697, filed on Jun. 25, 2008, provisional application No. 61/075,956, filed on Jun. 26, 2008.

(51) Int. Cl.
*C07K 16/24* (2006.01)

(52) U.S. Cl.
CPC ........ *C07K 16/241* (2013.01); *C07K 2317/24* (2013.01); *C07K 2317/55* (2013.01); *C07K 2317/565* (2013.01); *C07K 2317/567* (2013.01); *C07K 2317/622* (2013.01); *C07K 2317/92* (2013.01)

(58) Field of Classification Search
CPC ........ C07K 2317/567; C07K 2317/622; C07K 2317/565; C07K 2317/24; C07K 16/241
USPC ...................................................... 424/133.1
See application file for complete search history.

(56) References Cited

U.S. PATENT DOCUMENTS

| | | | |
|---|---|---|---|
| 4,275,149 A | 6/1981 | Litman et al. | |
| 4,318,980 A | 3/1982 | Boguslaski et al. | |
| 4,376,110 A | 3/1983 | David et al. | |
| 4,704,362 A | 11/1987 | Itakura et al. | |
| 4,737,456 A | 4/1988 | Weng et al. | |
| 4,881,175 A | 11/1989 | Ladner | |
| 4,946,778 A | 8/1990 | Ladner et al. | |
| 5,013,653 A | 5/1991 | Huston et al. | |
| 5,091,513 A | 2/1992 | Huston et al. | |
| 5,132,405 A | 7/1992 | Huston | |
| 5,225,539 A | 7/1993 | Winter | |
| 5,258,498 A | 11/1993 | Huston et al. | |
| 5,260,203 A | 11/1993 | Ladner et al. | |
| 5,304,489 A | 4/1994 | Rosen | |
| 5,455,030 A | 10/1995 | Ladner et al. | |
| 5,476,786 A | 12/1995 | Huston | |
| 5,482,858 A | 1/1996 | Huston et al. | |
| 5,530,101 A | 6/1996 | Queen et al. | |
| 5,585,089 A | 12/1996 | Queen et al. | |
| 5,644,034 A | 7/1997 | Rathjen et al. | |
| 5,654,407 A | 8/1997 | Boyle et al. | |
| 5,693,761 A | 12/1997 | Queen et al. | |
| 5,693,762 A | 12/1997 | Queen et al. | |
| 5,741,957 A | 4/1998 | Deboer et al. | |
| 5,795,967 A | 8/1998 | Aggarwal et al. | |
| 5,837,821 A | 11/1998 | Wu | |
| 5,849,992 A | 12/1998 | Meade et al. | |
| 5,859,205 A | 1/1999 | Adair et al. | |
| 6,090,382 A | 7/2000 | Salfeld et al. | |
| 6,180,370 B1 | 1/2001 | Queen et al. | |
| 6,407,213 B1 | 6/2002 | Carter et al. | |
| 6,509,015 B1 | 1/2003 | Salfeld et al. | |
| 6,548,640 B1 | 4/2003 | Winter | |
| 6,632,927 B2 | 10/2003 | Adair et al. | |
| 6,639,055 B1 | 10/2003 | Carter et al. | |
| 6,693,762 B2 | 2/2004 | Liu et al. | |
| 6,982,321 B2 | 1/2006 | Winter | |
| 7,022,500 B1 | 4/2006 | Queen et al. | |

(Continued)

FOREIGN PATENT DOCUMENTS

| | | |
|---|---|---|
| CA | 2688829 | 11/2008 |
| EP | 1918302 A2 | 7/2005 |

(Continued)

OTHER PUBLICATIONS

Borras et al. (The Journal of Biological Chemistry vol. 285, No. 12, pp. 9054-9066, (Mar. 19, 2010)).*

(Continued)

*Primary Examiner* — Lynn A Bristol

(74) *Attorney, Agent, or Firm* — Jason J. Derry

(57) ABSTRACT

The present invention relates to particularly stable and soluble scFv antibodies and Fab fragments specific for TNF, which comprise specific light chain and heavy chain sequences that are optimized for stability, solubility, in vitro and in vivo binding of TNF, and low immunogenicity. Said antibodies are designed for the diagnosis and/or treatment of TNF-mediated disorders. The nucleic acids, vectors and host cells for expression of the recombinant antibodies of the invention, methods for isolating them and the use of said antibodies in medicine are also disclosed.

21 Claims, 12 Drawing Sheets

Specification includes a Sequence Listing.

(56) References Cited

U.S. PATENT DOCUMENTS

| | | | |
|---|---|---|---|
| 7,241,877 | B2 | 7/2007 | Adair et al. |
| 7,244,615 | B2 | 7/2007 | Adair et al. |
| 7,244,832 | B2 | 7/2007 | Adair et al. |
| 7,262,050 | B2 | 8/2007 | Adair et al. |
| 7,429,487 | B2 | 9/2008 | Pytela et al. |
| 7,431,927 | B2 | 10/2008 | Couto et al. |
| 7,517,963 | B2 | 4/2009 | Rathjen et al. |
| 8,227,199 | B2* | 7/2012 | Urech .................. C07K 16/22 435/40.51 |
| 8,293,235 | B2 | 10/2012 | Borras et al. ............ 424/133.1 |
| 8,673,310 | B2* | 3/2014 | Borras ................ C07K 16/241 424/158.1 |
| 9,422,366 | B2* | 8/2016 | Borras ................ C07K 16/241 |
| 2004/0086979 | A1 | 5/2004 | Zhang et al. |
| 2005/0033031 | A1 | 2/2005 | Couto |
| 2005/0048578 | A1 | 3/2005 | Zhang |
| 2006/0099204 | A1 | 5/2006 | Couto et al. |
| 2006/0216293 | A1 | 9/2006 | Couto et al. |
| 2014/0212421 | A1* | 7/2014 | Hulmann-Cottier ........................ A61K 9/0043 424/135.1 |
| 2017/0107282 | A1* | 4/2017 | Shamshiev .......... C07K 16/241 |

FOREIGN PATENT DOCUMENTS

| | | |
|---|---|---|
| WO | 1986001533 | 3/1986 |
| WO | 198906692 | 7/1989 |
| WO | 199007861 A1 | 7/1990 |
| WO | 199101753 | 2/1991 |
| WO | WO1992/11383 A1 | 7/1992 |
| WO | 199409817 A1 | 5/1994 |
| WO | 200148017 A1 | 7/2001 |
| WO | 200202781 A1 | 1/2002 |
| WO | 2003097697 | 11/2003 |
| WO | 2004016740 | 2/2004 |
| WO | 2004087216 A2 | 10/2004 |
| WO | 2005016950 A1 | 2/2005 |
| WO | 2005035575 A2 | 4/2005 |
| WO | 2006131013 A2 | 12/2006 |
| WO | 2007001851 A | 1/2007 |
| WO | 2007042775 A2 | 4/2007 |
| WO | 2007042809 A2 | 4/2007 |
| WO | 2007047112 A | 4/2007 |
| WO | 2007124610 A | 11/2007 |
| WO | 2007140371 A | 12/2007 |
| WO | 2008004834 A | 1/2008 |
| WO | 2008006235 A2 | 1/2008 |
| WO | 2008063932 A2 | 5/2008 |
| WO | 2008110348 A1 | 9/2008 |
| WO | 2008144757 A1 | 11/2008 |
| WO | 2009000098 A2 | 12/2008 |
| WO | 2009000099 A2 | 12/2008 |
| WO | 2009155723 A2 | 12/2009 |
| WO | 2009155724 A1 | 12/2009 |
| WO | 2009155725 A1 | 12/2009 |
| WO | 2009155726 A2 | 12/2009 |

OTHER PUBLICATIONS

Adamis et al.; "Inhibition of vascular endothelial growth factor prevents retinal ischemia-associated iris neovascularization in a nonhuman primate"; Arch. Ophthalmol. vol. 114; pp. 66-71 (1996).
Aiello et al.; "Vascular endothelial growth factor in ocular fluid of patients with diabetic retinopathy and other retinal disorders"; N. Engl. J. Med.; vol. 331; pp. 480-487 (1994).
Kaija Alfthan, et al., "Properties of a Single-Chain Antibody Containing Different Linker Peptides," Protein Engineering, 1995, pp. 725-731, vol. 8, No. 7.
Allen; "Ligand-targeted therapeutics in anticancer therapy"; Nature; Reviews; Cancer; vol. 2; pp. 750-763 (Oct. 2002).
Auf Der Maur et al; "Antigen independent selection of stable intracellular single-chain antibodies"; FEBS Letters: vol. 508; pp. 407-412 (2001).
Banyay et al.; "Three-dimensional imaging in in situ specimens with low-dose electron tomography to analyze protein conformation"; Assay and Drug Development Technologies; vol. 2; No. 5; pp. 561-567; (Nov. 5, 2004).
Berkman et al.; "Expression of the vascular permeability factor/vascular endothelial growth factor gene in central nervous system neoplasms"; J. Clin. Invest.; vol. 91; pp. 153-159 (1993).
Bird et al.; "Single-chain antigen-binding proteins"; Science; vol. 242; pp. 423-426 (Oct. 21, 1988).
Borgstrom et al.; "Complete inhibition of angiogenesis and growth of microtumors by anti-vascular endothelial growth factor neutralizing antibody: novel concepts of angiostatic therapy from intravitral videomicroscopy" Cancer Research; vol. 56; pp. 4032-4039 (Sep. 1, 1996).
Boulianne et al.; "production of functional chimaeric mouse/human antibody"; Letters to nature; Nature; vol. 312; pp. 643-646 (Dec. 13, 1984).
Brennan et al.; "Preparation of bispecific antibodies by chemical recombination of monoclonal immunoglobulin G1 fragments"; Science; vol. 229; pp. 81-83 (1985).
Brown, et al; "Expression of vascular permeability factor (vascular endothelial growth factor) and its receptors in adenocarcinomas of the gastrointestinal tract"; Cancer Research; vol. 53; pp. 4727-4735 (Oct. 1, 1993).
Brown et al.; "Expression of vascular permeability factor (vascular endothelial growth factor) and its receptors in breast cancer"; Human Pathology; vol. 26; pp. 86-91 (1995).
Brummell et al.; "Probing the combining site of an anti-carbohydrate antibody by saturation-mutagenesis: role of the heavy-chain CDR3 residues"; Biochemistry; vol. 32; pp. 1180-1187 (1993).
Burks et al.; "In vitro scanning saturation mutagenesis of an antibody binding pocket"; Proc. Natl. Acad. Sci.; vol. 94; pp. 412-417 (Jan. 1997).
Beutler and Cerami; "Cachectin and tumour necrosis factor as two sides of the same biological coin"; Nature; vol. 320; pp. 584-588 (Apr. 17, 1986).
Calandra et al.; "Prognostic values of tumor necrosis factor/cachectin, interleukin-1, interferon-alpha, and interferon-γ in the serum of patients with septic shock"; Journal of Infectious Diseases; vol. 161; pp. 982-987 (1990).
Carter et al; "Improved oligonucleotide site-directed mutagenesis using M13 vectors"; Nucleic Acids Research; vol. 13; No. 12; pp. 4431-4443; (1985).
Cerami and Beutler; "The role of cachectin/TNF in endotoxic shock and cachexia"; Immunology Today; vol. 9; No. 1; pp. 28-31 (1988).
Choi et al.; "Recombinant chimeric OKT3 scFv IgM antibodies mediate immune suppression while reducing T cell activation in vitro"; Eur. J. Immunol.; vol. 31; pp. 94-106 (2001).
Clark; Antibody humanization: a case of the 'Emperor's new clothes'?; review; Immunology today; vol. 21; No. 8; pp. 397-402 (2000).
Co et al; "Chimeric and humanized antibodies with specificity for the CD33 antigen"; The Journal of Immunology; vol. 148; pp. 1149-1154 (Feb. 15, 1992).
Cornette et al; "Hydrophobicity scales and computational techniques for detecting amphipathic structures in proteins"; J. Mol. Biol., vol. 195; pp. 659-685 (1987).
Debets et al.; "Plasma tumor necrosis factor and mortality in critically ill septic patients"; Critical Care Medicine; vol. 17; No. 6; pp. 489-494 (Jun. 1989).
Devries et al.; "The fms-like tyrosine kinase, a receptor for vascular endothelial growth factor"; Science; vol. 255; pp. 989-991; (Feb. 21, 1992).
Dillman et al.; "Human anti-mouse antibody response in cancer patients following single low-dose injections of radiolabeled murine monoclonal antibodies"; vol. 9; No. 1; pp. 17-29 (1994).
Doring et al.; "Identification and characterization of a TNF alpha; antagonist derived from a monoclonal antibody"; Molecular Immunology; vol. 31; No. 5; pp. 1059-1067 (1994).
Dumoulin et al; "Single-domain antibody fragments with high conformational stability"; Protein Science; vol. 11; pp. 500-515 (2002).

(56) References Cited

OTHER PUBLICATIONS

Dvorak et al.; "Vascular permeability factor/vascular endothelial growth factor, microvascular hyperpermeability, and angiogenesis"; American Journal of Pathology; vol. 146; No. 5; pp. 1029-1039 (May 1995).
Ewert et al.; "Structure-based improvement of the biophysical properties of immunoglobulin VH domains with a generalizable approach"; Biochemistry, American Chemical Society; vol. 42; No. 6; pp. 1517-1528 (Feb. 18, 2003).
Ewert et al.; "Stability improvement of antibodies for extracellular and intracellular applications: CDR grafting to stable frameworks and structure-based framework engineering"; Methods: A Companion to Methods in Enzymology; vol. 34; No. 2; pp. 184-199 (Oct. 1, 2004).
Ferrara and Davis-Smyth; "The biology of vascular endothelial growth factor"; Endocrine Reviews; vol. 18; No. 1; pp. 4-25 (Feb. 25, 2005).
Folkman and Shing; Angiogenesis; The Journal of Biological Chemistry; vol. 267; No. 16; pp. 10931-10934 (1992).
Fuh et al.; Structure-function studies of two synthetic anti-vascular endothelial growth factor fabs and comparison with the Avastin (TM) fab; The Journal of Biological Chemistry; vol. 281; No. 10; pp. 6625-6631 (Mar. 10, 2006).
Furrer et al.; "Pharmacokinetics and posterior segment biodistribution of ESBA105, an anti-TNF-alpha single-chain antibody, upon topical administration to the rabbit"; Investigative Ophthalmology & Visual Science; vol. 50; No. 2; pp. 771-778 (Feb. 1, 2009).
Gawaz et al.; "Llgand bridging mediates integrin allphallbbeta3 (Platelet GPIIB-IIIA) dependent homotypic and heterotypic cell-cell interactions"; J. Clin. Invest.; vol. 88; pp. 1128-1134 (Oct. 1991).
Glennie et al.; "Preparation and performance of bispecific F(ab'y)2 antibody containing thioether-linked Fab'y fragments"; The Journal of Immunology; vol. 139; No. 7; pp. 2367-2375 (Oct. 1, 1987).
Grell et al.; "The transmembrane form of tumor necrosis factor is the prime activating ligand of the 80 kDa tumor necrosis factor receptor"; vol. 83; pp. 793-802; (Dec. 1, 1995).
Hamers-Casterman et al.; "Naturally occurring antibodies devoid of light chains"; Letters to Nature; vol. 363; pp. 446-448 (Jun. 3, 1993).
Ho et al; "Site-directed mutagenesis by overlap extension using the polymerase chain reaction"; Gene; vol. 77; pp: 51-59 (1989).
Hollinger et al.; "Diabodies: small bivalent and bispecific antibody fragments"; Proc. Natl. Acad. Sci.; vol. 90; pp. 6444-6448 (Jul. 1993).
Honegger and Pluckthun; "Yet another numbering scheme for immunoglobulin variable domains: an automatic modeling and analysis tool"; J. Mol. Biol.; vol. 309; pp. 657-670 (2001).
Horak et al; "Angiogenesis, assessed by platelet/endothelial cell adhesion molecule antibodies, as indicator of node metastases and survival in breast cancer"; The Lancet; vol. 340; pp. 1120-1124 (Nov. 7, 1992).
Houck, et al.; "The vascular endothelial growth factor family: identification of a fourth molecular species and characterization of alternative splicing of RNA"; Molecular Endocrinology; vol. 5; pp. 1806-1814 (1991).
Hu et al.; "Minibody: a novel engineered anti-carcinoembryonic antigen antibody fragment (single-chain Fv-CH3) which exhibits rapid, high-level targeting of xenografts"; Cancer Research; vol. 56; pp. 3055-3061 (Jul. 1, 1996).
Huston et al.; "Protein engineering of antibody binding sites: recovery of specific activity in an anti-digoxin single-chain Fv analogue produced in *escherichia coli*"; Proc. Natl. Acad. Sci.; vol. 85; pp. 5879-5883 (Aug. 1988).
Jones et al.; "Replacing the complementarity-determining regions in a human antibody with those from a mouse"; Nature; vol. 321; pp. 522-525 (May 1986).
Jones; "Analysis of polypeptides and Proteins"; Advanced Drug Delivery Reviews; vol. 10: pp. 29-90 (1993).

Jung et al.; "Improving in vivo folding and stability of a single-chain FV antibody fragment by loop grafting"; Protein Engineering; vol. 10; No. 8; pp. 959-966 (Jan. 1, 1997).
Karpovsky et al.; "Production of target-specific effect or cells using hetero-cross-linked aggregates containing anti-target cell and anti-Fcy receptor antibodies"; Journal of Experimental Medicine; vol. 160; pp. 1686-1701 (Dec. 1984).
Borras, Leonardo, Prosecution History, U.S. Appl. No. 14/011,831, Filed Aug. 28, 2013, 2374 pages.
De Pascalis et al. The Journal of Immunology (2002) 169, 3076-3084.
Vajdos et al. ((2002) J. Mol. Biol. 320, 415-428).
Wu et al. (J. Mol. Biol. (1999) 294, 151-162).
Coleman (Research in Immunol. 145:33-36 (1994)).
Dufner (Trends Biotechnol. 24(11):523-29 (2006)).
Royt, A., "Enzymatic digestion of human IgG1"; Immunology, Moscow, "Mir", 200, Chapter 6; p. 110-111. "Interaction of antibodies with antigens"; Chapter 9 p. 150.
Kim et al.; "Inhibition of vascular endothelial growth factor-induced angiogenesis suppresses tumour growth in vivo"; Letters to Nature; vol. 362; pp. 841-844 (Apr. 29, 1993).
Kipriyanov et al; "Bispecific tandem diabody for tumor therapy with improved antigen binding and pharmacokinetics"; J. Mol. Biol.; vol. 293; pp. 41-56 (1999).
Klagsbrun; "Regulators of angiogenesis"; Annu. Rev. Physiol.; vol. 53; pp. 217-239 (1991).
Knappik et al; "Fully synthetic human combinatorial antibody libraries (HuCAL) based on modular consensus frameworks and CDRs randomized with trinucleotides"; J. Mol. Biol.; vol. 296; pp. 57-86 (2000).
Kobayashi et al; "Tryptophan H33 plays an important role in pyrimidine (6-4) pyrimidone photoproduct binding by a high-affinity antibody"; Protein Engineering; vol. 12; No. 10; pp. 879-884 (1999).
Kriegler et al.; "A novel form of TNF/cachectin is a cell surface cytotoxic transmembrane Protein: ramifications for the complex physiology of TNF;" Cell; vol. 53; pp. 45-53 (Apr. 8, 1988).
Kugler et al.; "Stabilizatin and humanization of a single-chain Fv antibody fragment specific for human lymphocyte antigen CD19 by designed point mutations and CDR-grafting onto a human framework"; Protein Engineering, Design & Selection; vol. 22; No. 3; pp. 135-147 (Feb. 1, 2009).
Kunkel; Rapid and efficient site-spectic mutagenesis without phenotypic selection; Proc. Natl. Acad. Sci.; vol. 82; pp. 488-492 (Jan. 1985).
Leong and Hibma; "A flow cytometry-based assay for the measurement of protein regulatin of E-cadherin-mediated adhesion"; Journal of Immunological Methods; vol. 302; pp. 116-124 (2005).
Leung et al.; "Vascular endothelial growth factor is a secreted angiogenic mitogen"; Science; vol. 246; pp. 1306-1309 (Dec. 8, 1989).
Liang et al.; "Cross-species vascular endothelial growth factor (VEGP)-blocking antibodies completely inhibit the growth of human tumor xenografts and measure the contribution of stromal VEGF"; The Journal of Biological Chemistry; vol. 281; No. 2; pp. 951-961 (Jan. 13, 2006).
Liu et al.; "Heteroantibody duplexes target cells for lysis by cytotoxic T lymphocytes"; Proc. Natl. Acad. Sci.; vol. 82; pp. 8648-8652 (Dec. 1985).
Lopez et al.; "Transdifferentiated retinal pigment epithelial cells are immunoreactive for vascular endothelial growth factor in surgically excised age-related macular degeneration-related choroidal neovascular membranes"; Investigative Ophthalmology & Visual Science; vol. 37; No. 5; pp. 855-868 (Apr. 1996).
Macchiarini et al.; "Relation of neovascularization to metastasis of non-small-cell lung cancer"; Short Report; The Lancet; vol. 340; pp. 145-146 (Jul. 18, 1992).
Mattern et al.; "Associatin of vascular endothelial growth factor expression with intratumoral microvessel density land tumour cell proliferation in human epidermoid lung carcinoma"; British Journal of Cancer; vol. 73; pp. 931-934 (1996).

(56) References Cited

OTHER PUBLICATIONS

Matthews et al.; "A receptor tyrosine kinase cDNA isolated from a populatipn of enriched primitive hematopoietic cells and exhibiting close genetic linkage to c-kit"; Proc. natl. Acad. Sci.; vol. 88; pp. 9026-9030 (Oct. 1991).
McKnown et al.; Lack of efficacy of oral bovine type II collagen added to existing therapy in rheumatoid arthritis; Arthritis & Rheumatism; vol. 32; pp. 1204-1208 (Jun. 6, 1999).
Melnyk et al.; "Vascular endothelial growth factor promotes tumor dissemination by a mechanism distinct form its effect on primary tumor growth"; Cancer Research; vol. 56; pp. 921-924 (Feb. 15, 1996).
Myers and Miller; "Optimal alignments in linear space"; Cabios; vol. 4; No. 1; pp. 11-17 (1988).
Michie et al.; "Tumour necrosis factor and bacterial sepsis"; Br. J. Surg.; vol. 76; pp. 670-671 (Jul. 1989).
Milenic et al; "Construction, binding properties, metabolism, and tumor targeting of a single-chain Fv derived form the pancarcinoma monoclonal antibody CC49"; Cancer Research; vol. 51; pp. 6363-6371 (Dec. 1, 1991).
Needleman and Wunsch; "A general method applicable to the search for similarities in the amino acid sequence of two proteins"; J. Mol. Biol.; vol. 48; pp. 443-453 (1970).
Ottiger et al.; "Efficient intraocular penetration of topical anti-TNF-alpha single-chain antibody (ESBA105) to anterior and posterior segment without penetration enhancer"; Investigative Ophthalmology and Visual Science; vol. 50; No. 2; pp. 779-786 (Feb. 1, 2009).
Panorchan et al.; Single-molecule analysis of cadherin-mediated cell-cell adhesion; Journal of Cell Science; vol. 119; pp. 66-74; (2006).
Pantolano et al; "Conformational stability, folding, and ligand-binding affinity of single-chain Fv immunoglobulin fragments expressed in *Esericha coli*"; Biochemistry; vol. 30; pp. 10117-10125 (1991).
Pastan and Kreitman; "Overview: Immunotoxins in cancer therapy"; Current Opinion Investig. Drugs; vol. 3; pp. 1089-1091 (2002).
Paulus; "Preparation and biomedical applications for bispecific antibodies", Behring Inst. Mitt.; No. 78; pp. 118-132 (1985).
Payne; "Progess in immunoconjugate cancer therapeutics"; Cancer Cell; vol. 3; pp. 207-212 (Mar. 2003).
Popkov et al.; "Rabbit immune repertoires as sources for therapeutic monoclonal antibodies: the impact of kappa allotype-correlated variation in cysteine content on antibody libraries selected by phage display"; Journal of Molecular Biology; vol. 325; No. 2; pp. 325-335 (Jan. 10, 2003).
Queen et al; "Cell-type specific regulation of a k immunoglobulin gene by promoter and enhancer elements"; Immunological Reviews; pp. 49-68 (1986).
Queen et al.; "A humanized antibody that binds to the interleukin 2 receptor"; Proc. Natl. Acad. Sci.; vol. 86; pp. 10029-10033 (Dec. 1989).
Rader et al.; "The rabbit antibody repertoire as a novel source for the generation of therapeutic human antibodies"; The Journal of Biological Chemistry; vol. 275; No. 18; pp. 13668-13676 (2000).
Ran et al.; "Generation of new rabbit monoclonal antibody RAM-1 against human VEGF-C"; Proceedings of the annual meetings of the American Association for Cancer; Tumor Biology; vol. 46; p. 911 (2005).
Revhaug et al.; "Inhibition of cyclo-oxygenase attenuates the metabolic response to endotoxin in humans"; Arch. Surg.; vol. 123; pp. 162-170 (Feb. 1988).
Riechmann et al.; "Reshaping human antibodies for therapy"; Nature; vol. 332; pp. 323-327 (Mar. 1998).
Rocha et al.; "Rabbit monoclonal antibodies show higher sensitivity than mouse monoclonals for estrogen and progesterone receptor evaluation in breast cancer by immunohistochemistry"; Pathology Research and Practice; vol. 204; No. 9; pp. 655-662 (Sep. 2008).
Roguska et al.; "A comparison of two murine monoclonal antibodies humanized by CDR-grafting and variable domain resurfacing"; Protein Engineering; vol. 9; No. 10; pp. 895-904 (1006).

Roovers and Van der Linden; "In vitro characterization of a monovalent and bivalent form of a fully human anti-Ep-CAM phage antibody"; Cancer Immunol. Immunother; vol. 50; pp. 51-59 (2001).
Rose et al.; "Hydrophobicity of amino acid residues in globular proteins"; Science; vol. 229; pp. 834-838 (1985).
Saijo et al.; "Comparison of reactivity of monoclonal antibody (3F2) to trimeric tumor necrosis factor (TNF-alpha) with that to monomeric TNF-alpha 1"; J. Biochem.; vol. 118; pp. 28-32 (1995).
Saito, et al.; "Drug delivery strategy utilizing conjugation via reversible disulfide linkages: role and site of cellular reducing activities"; Advanced Drug Delivery Reviews; vol. 55; pp. 119-215 (2003).
Senter and Springer; "Selective activation of anticancer prodrugs by monoclonal antibody-enzyme conjugates"; Advanced Drug Delivery Reviews; vol. 53; pp. 247-264 (2001).
Shawler et al; "Human immune response to multiple injections of murine monoclonal IgG1"; The Journal of Immunology; vol. 135; No. 2; pp. 1530-1535 (Aug. 1985).
Shibuya et al.; "Nucleotide sequence and expression of a novel human receptor-type tyrosine kinase gene (flt) closely related to the fms family"; Oncogene; vol. 5; pp. 519-524 (1990).
Simpson and Casey; "Role of tumor necrosis factor in sepsis and acute lung injury"; Septic Shock; Critical Care Clinics; vol. 5; No. 1; pp. 27-47 (Jan. 1989).
Skerra and Pluckthun; "Assembly of a functional immunoglobulin Fv fragment in *escherichia coli*"; Science; vol. 240; pp. 1038-1041 (May 20, 1988).
Smith and Baglioni; "The active form of tumor necrosis factor is a trimer"; Communication; The Journal of Biological Chemistry; vol. 262; No. 15; pp. 6951-6954 (May 25, 1987).
Spieker-Polet et al; "Rabbit monoclonal antibodies: generating a fusion partner to produce rabbit-rabbit hybidomas"; Proc. Natl. Acad. Sci.; vol. 92; pp. 9348-9352 (Sep. 1995).
Takkinen et al; "An active single-chain antibody containing a cellulase linker domain is secreted by *Escherichia coli*"; Protein Engineering; vol. 4; No. 7; pp. 837-841 (1991).
Taub et al.; "A monoclonal antibody against the platelet fibrinogen receptor contains a sequence that mimics a receptor recognition domain in fibrinogen"; The Journal of Biological Chemistry; vol. 264; No. 1; pp. 259-265 (Jan. 5, 1989).
Terman et al.; "Identification of a new endothelial cell growth factor receptor tyrosine kinase"; Oncogene; vol. 6; pp. 1677-1683 (1991).
Terman et al.; "Identification of the KDR tyrosine kinase as a receptor for vascular endothelial cell growth factor"; Biochemical and Biophysical Research Communications vol. 187; No. 3; pp. 1579-1586 (Sep. 30, 1992).
Thorpe and Ross; "The preparation and cytotoxic properties of antibody-toxinconjugates"; Immunological Review; vol. 62; pp. 119-158 (1982).
Tisdale; "Cancer cachexia"; Langenbecks Arch. Surg.; vol. 389; pp. 299-305 (2004).
Trail et al.; "Monoclonal antibody drug immunoconjugates for targeted treatment of cancer"; Cancer Immunol Immunother; vol. 52; pp. 328-337 (2003).
Vallette et al; "Construction of; mutant and chimeric genes using the polymerase chain reaction"; Nucleic Acids Research; vol. 17; No. 2; pp. 723-733 (1989).
Waage et al.; "Association between tumour necrosis factorin serum and fatal outcome in patients with meningococcal disease"; The Lancet; vol. 1; pp. 355-357 (Feb. 14, 1987).
Old; Tumor necrosis factor (TNF); Science; vol. 230; pp. 630-632; (1986).
Ward et al; "Binding activities of a repertoire of single immunoglobulin variable domains secreted form *Escherichia coli*"; Letters to Nature; vol. 341; pp. 544-546 (Oct. 12, 1989).
Warren et al.; "Regulation by vascular endothelial growth factor of human colon cancer tumorigenesis in a mouse model of experimental liver metastasis"; J. Clin. Invest.; vol. 95; pp. 1789-1797 (1995).
Weidner et al; "Tumor angiogenesis and metastasis—correlation in invasive breast carcinoma"; The New England Journal of Medicine; vol. 324; No. 1; pp. 1-6 (Jan. 3, 1991).

(56) References Cited

OTHER PUBLICATIONS

Wells et al; "Cassette mutagenesis: an efficient method for generation of multiple mutations at defined sites"; Gene; vol. 34; pp. 315-323 (1985).
Worn and Pluckthun; "Stability engineering of antibody single-chain Fv fragments"; J. Mol. Biol.; vol. 305; pp. 989-1010 (2001).
Zhang et al.; Antibody and Antibody Targets; Proceedings of the annual meeting of the American Assoc. for Cancer Research; vol. 50; pp. 296 (Apr. 22, 2009).
Zubler et al.; "Mutant EL-4 thymoma cells polyclonally activate murine and human B ells via direct cell interaction"; The Journal of Immunology; vol. 134; No. 6: pp. 3662-3668 (Jun. 1985).
Search Report and Written Opinion for corresponding PCT application No. CH2009000219 dated Mar. 9, 2010.
Keffer, et al.; "Transgenic mice expressing human tumour necrosis factor: a predictive genetic model of arthritis"; The EMBO Journal; vol. 10; No. 13; pp. 4025-4031 (1991).

* cited by examiner

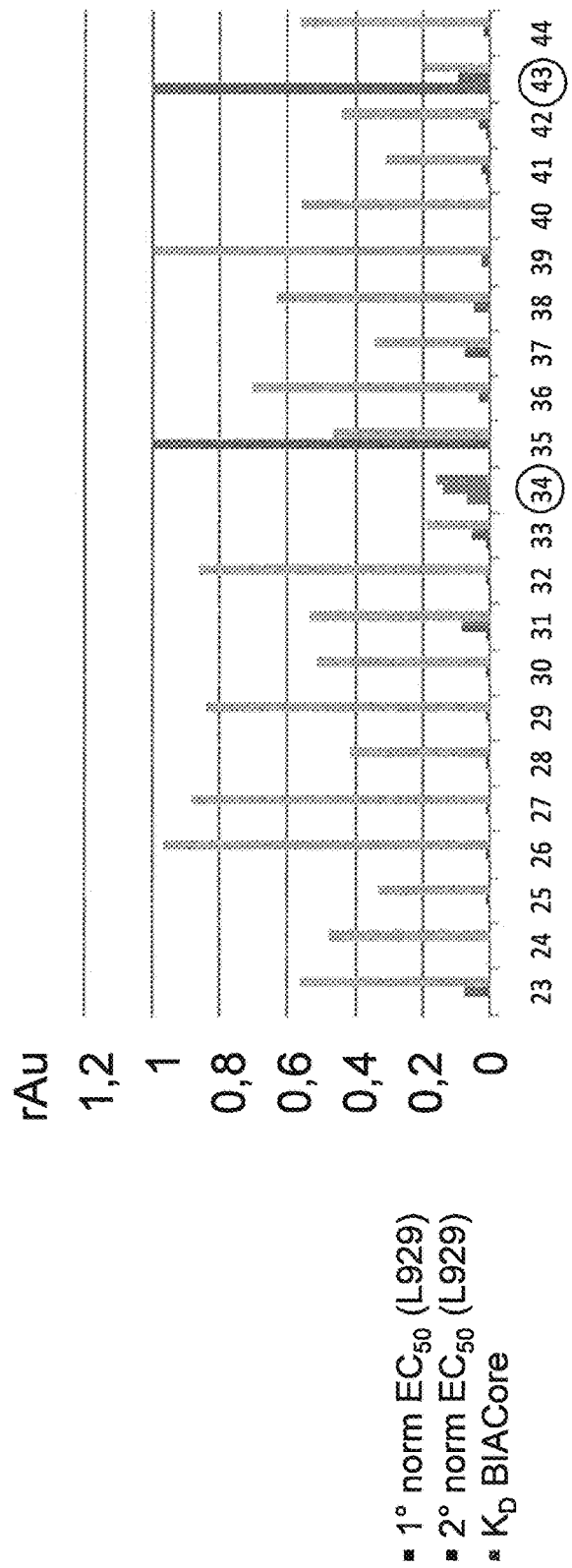

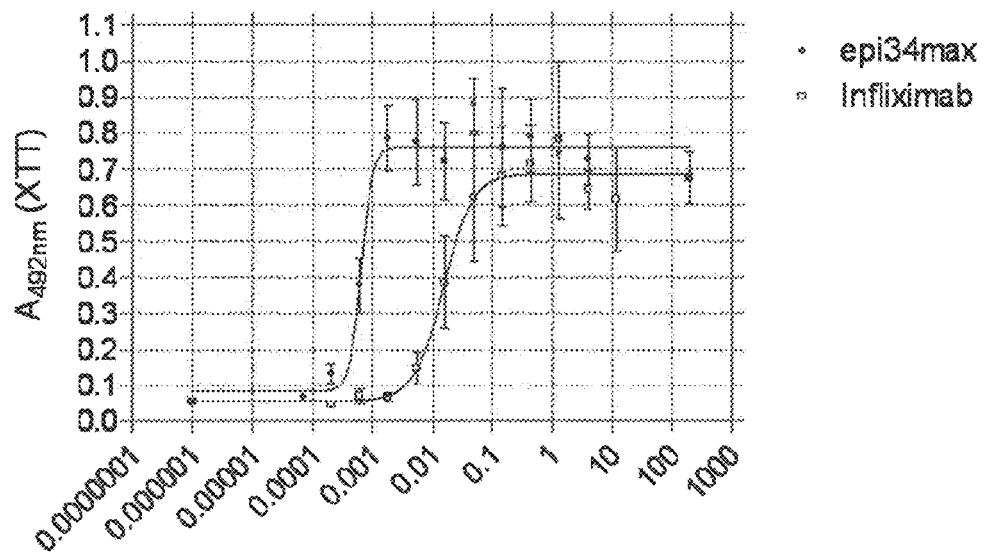
Fig. 10A ug/mL
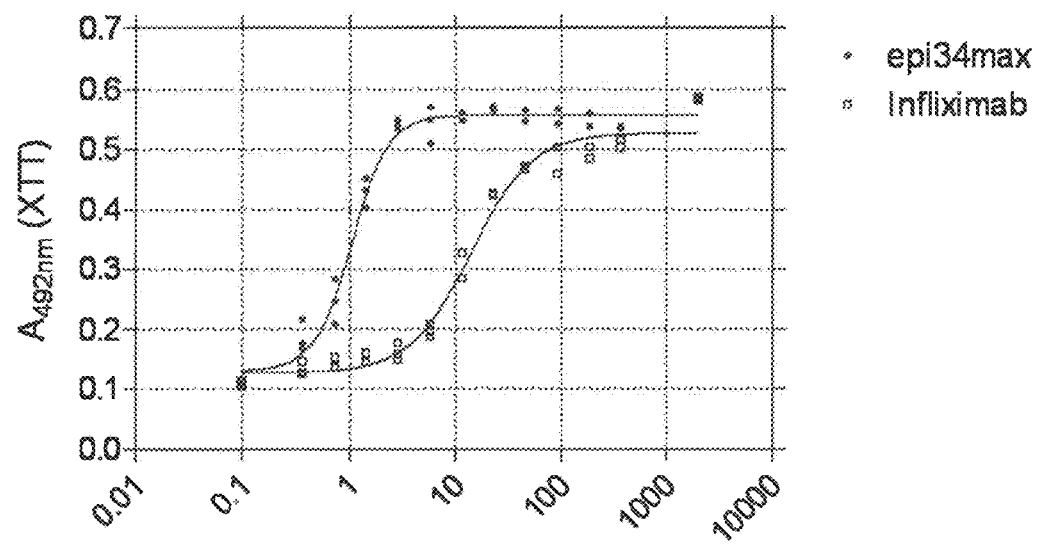
Fig. 10B ng/mL

SEQUENCE LISTING

<160> NUMBER OF SEQ ID NOS: 122

<210> SEQ ID NO 1
<211> LENGTH: 230
<212> TYPE: PRT
<213> ORGANISM: Homo sapiens
<220> FEATURE:
<221> NAME/KEY: MISC_FEATURE
<222> LOCATION: (24)..(73)
<223> OTHER INFORMATION: CDR1; at least 3 and up to 50 amino acids can
      be present or absent; Xaa can be any naturally occuring amino acid
<220> FEATURE:
<221> NAME/KEY: MISC_FEATURE
<222> LOCATION: (89)..(138)
<223> OTHER INFORMATION: CDR2; at least 3 and up to 50 amino acids can
      be present or absent; Xaa can be any naturally occuring amino acid
<220> FEATURE:
<221> NAME/KEY: MISC_FEATURE
<222> LOCATION: (170)..(219)
<223> OTHER INFORMATION: CDR3; at least 3 and up to 50 amino acids can
      be present or absent; Xaa can be any naturally occuring amino acid

<400> SEQUENCE: 1

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Val Pro Ser Arg Phe Ser
    130                 135                 140

Gly Ser Gly Ser Gly Ala Glu Phe Thr Leu Thr Ile Ser Ser Leu Gln
145                 150                 155                 160

Pro Asp Asp Phe Ala Thr Tyr Tyr Cys Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Phe Gly Gln Gly Thr
    210                 215                 220

Lys Leu Thr Val Leu Gly
225                 230

<210> SEQ ID NO 2
<211> LENGTH: 232
<212> TYPE: PRT
<213> ORGANISM: Homo sapiens
<220> FEATURE:
<221> NAME/KEY: CDP
<222> LOCATION: (26)..(75)
<223> OTHER INFORMATION: CDR1; at least 3 and up to 50 amino acids can

```
      be present or absent; Xaa can be any naturally occuring amino acid
<220> FEATURE:
<221> NAME/KEY: CDP
<222> LOCATION: (90)..(139)
<223> OTHER INFORMATION: CDR2; at least 3 and up to 50 amino acids can
      be present or absent; Xaa can be any naturally occuring amino acid
<220> FEATURE:
<221> NAME/KEY: CDP
<222> LOCATION: (172)..(221)
<223> OTHER INFORMATION: CDR3; at least 3 and up to 50 amino acids can
      be present or absent; Xaa can be any naturally occuring amino acid

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
            50                  55                  60

Xaa Xaa Xaa Xaa Xaa Xaa Xaa Xaa Xaa Xaa Trp Val Arg Gln Ala
65                  70                  75                  80

Pro Gly Lys Gly Leu Glu Trp Val Ser Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Arg Phe Thr Ile Ser
            130                 135                 140

Arg Asp Asn Ser Lys Asn Thr Leu Tyr Leu Gln Met Asn Ser Leu Arg
145                 150                 155                 160

Ala Glu Asp Thr Ala Val Tyr Tyr Cys Ala Lys Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Xaa Xaa Xaa Trp Gly Gln
            210                 215                 220

Gly Thr Leu Val Thr Val Ser Ser
225                 230

<210> SEQ ID NO 3
<211> LENGTH: 10
<212> TYPE: PRT
<213> ORGANISM: Artificial Sequence
<220> FEATURE:
<223> OTHER INFORMATION: EP43 CDR-H1

<400> SEQUENCE: 3

Gly Phe Ser Leu Ser Ser Gly Ala Met Ser
1               5                   10

<210> SEQ ID NO 4
<211> LENGTH: 16
<212> TYPE: PRT
<213> ORGANISM: Artificial Sequence
<220> FEATURE:
<223> OTHER INFORMATION: EP43 CDR-H2
```

```
<400> SEQUENCE: 4

Val Ile Ile Ser Ser Gly Ala Thr Tyr Tyr Ala Ser Trp Ala Lys Gly
1               5                   10                  15

<210> SEQ ID NO 5
<211> LENGTH: 14
<212> TYPE: PRT
<213> ORGANISM: Artificial Sequence
<220> FEATURE:
<223> OTHER INFORMATION: EP-43 CDR-H3

<400> SEQUENCE: 5

Gly Gly Pro Asp Asp Ser Asn Ser Met Gly Thr Phe Asp Pro
1               5                   10

<210> SEQ ID NO 6
<211> LENGTH: 11
<212> TYPE: PRT
<213> ORGANISM: Artificial Sequence
<220> FEATURE:
<223> OTHER INFORMATION: EP43 CDR-L1

<400> SEQUENCE: 6

Gln Ala Ser Gln Ser Ile Ser Asp Trp Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: EP43 CDR-L2

<400> SEQUENCE: 7

Gly Ala Ser Arg Leu Ala Ser
1               5

<210> SEQ ID NO 8
<211> LENGTH: 12
<212> TYPE: PRT
<213> ORGANISM: Artificial Sequence
<220> FEATURE:
<223> OTHER INFORMATION: EP43 CDR-L3

<400> SEQUENCE: 8

Gln Gln Gly Trp Ser Asp Ser Tyr Val Asp Asn Leu
1               5                   10

<210> SEQ ID NO 9
<211> LENGTH: 10
<212> TYPE: PRT
<213> ORGANISM: Artificial Sequence
<220> FEATURE:
<223> OTHER INFORMATION: EP1 CDR-H1

<400> SEQUENCE: 9

Gly Ile Asp Leu Ser Asn Asp Ala Ile Ser
1               5                   10

<210> SEQ ID NO 10
<211> LENGTH: 16
<212> TYPE: PRT
<213> ORGANISM: Artificial Sequence
<220> FEATURE:
<223> OTHER INFORMATION: EP1 CDR-H2
```

```
<400> SEQUENCE: 10

Tyr Ile Ser Asp Trp Ser Ile Arg Tyr Tyr Ala Asn Trp Ala Gln Gly
1               5                   10                  15

<210> SEQ ID NO 11
<211> LENGTH: 10
<212> TYPE: PRT
<213> ORGANISM: Artificial Sequence
<220> FEATURE:
<223> OTHER INFORMATION: EP1 CDR-H3

<400> SEQUENCE: 11

Gly Ala Pro Gly Ala Gly Asp Asn Gly Ile
1               5                   10

<210> SEQ ID NO 12
<211> LENGTH: 13
<212> TYPE: PRT
<213> ORGANISM: Artificial Sequence
<220> FEATURE:
<223> OTHER INFORMATION: EP1 CDR-L1

<400> SEQUENCE: 12

Gln Ser Thr Glu Ser Val Tyr Lys Asn Asn Tyr Leu Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: EP1 CDR-L2

<400> SEQUENCE: 13

Asp Ala Ser Thr Leu Ala Ser
1               5

<210> SEQ ID NO 14
<211> LENGTH: 14
<212> TYPE: PRT
<213> ORGANISM: Artificial Sequence
<220> FEATURE:
<223> OTHER INFORMATION: EP1 CDR-L3

<400> SEQUENCE: 14

Ala Gly Tyr Tyr Arg Ser Gly Ser Gly Thr Ala Asn Gly Ser
1               5                   10

<210> SEQ ID NO 15
<211> LENGTH: 10
<212> TYPE: PRT
<213> ORGANISM: Artificial Sequence
<220> FEATURE:
<223> OTHER INFORMATION: EP6 CDR-H1

<400> SEQUENCE: 15

Gly Phe Ser Leu Ser Arg Tyr Gly Val Ser
1               5                   10

<210> SEQ ID NO 16
<211> LENGTH: 16
<212> TYPE: PRT
<213> ORGANISM: Artificial Sequence
<220> FEATURE:
<223> OTHER INFORMATION: EP6 CDR-H2

<400> SEQUENCE: 16
```

```
Thr Ile Gly Glu Ala Gly Arg Ala Tyr Tyr Ala Asn Trp Ala Arg Ser
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: EP6 CDR-H3

<400> SEQUENCE: 17

Gly Glu Val Phe Asn Asn Gly Trp Gly Ala Phe Asn Ile
1               5                   10

<210> SEQ ID NO 18
<211> LENGTH: 11
<212> TYPE: PRT
<213> ORGANISM: Artificial Sequence
<220> FEATURE:
<223> OTHER INFORMATION: EP6 CDR-L1

<400> SEQUENCE: 18

Gln Ala Ser Glu Ser Ile Tyr Ser Gly Leu Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: EP6 CDR-L2

<400> SEQUENCE: 19

Gln Ala Ser Thr Leu Ala Ser
1               5

<210> SEQ ID NO 20
<211> LENGTH: 12
<212> TYPE: PRT
<213> ORGANISM: Artificial Sequence
<220> FEATURE:
<223> OTHER INFORMATION: EP6 CDR-L3

<400> SEQUENCE: 20

Gln Gln Gly Phe Gly Thr Ser Asn Val Glu Asn Pro
1               5                   10

<210> SEQ ID NO 21
<211> LENGTH: 10
<212> TYPE: PRT
<213> ORGANISM: Artificial Sequence
<220> FEATURE:
<223> OTHER INFORMATION: EP15 CDR-H1

<400> SEQUENCE: 21

Gly Phe Ser Leu Ser Arg Tyr Gly Val Ser
1               5                   10

<210> SEQ ID NO 22
<211> LENGTH: 16
<212> TYPE: PRT
<213> ORGANISM: Artificial Sequence
<220> FEATURE:
<223> OTHER INFORMATION: EP15 CDR-H2

<400> SEQUENCE: 22
```

```
Ala Ile Gly Glu Thr Gly Arg Ala Tyr Tyr Ala Asn Trp Ala Lys Ser
1               5                   10                  15

<210> SEQ ID NO 23
<211> LENGTH: 13
<212> TYPE: PRT
<213> ORGANISM: Artificial Sequence
<220> FEATURE:
<223> OTHER INFORMATION: EP15 CDR-H3

<400> SEQUENCE: 23

Gly Glu Glu Phe Asn Asn Gly Trp Gly Ala Phe Asn Ile
1               5                   10

<210> SEQ ID NO 24
<211> LENGTH: 11
<212> TYPE: PRT
<213> ORGANISM: Artificial Sequence
<220> FEATURE:
<223> OTHER INFORMATION: EP15 CDR-L1

<400> SEQUENCE: 24

Gln Ala Ser Glu Asn Ile Tyr Thr Ser Leu Ala
1               5                   10

<210> SEQ ID NO 25
<211> LENGTH: 7
<212> TYPE: PRT
<213> ORGANISM: Artificial Sequence
<220> FEATURE:
<223> OTHER INFORMATION: EP15 CDR-L2

<400> SEQUENCE: 25

Ser Ala Ser Thr Leu Ala Ser
1               5

<210> SEQ ID NO 26
<211> LENGTH: 12
<212> TYPE: PRT
<213> ORGANISM: Artificial Sequence
<220> FEATURE:
<223> OTHER INFORMATION: EP15 CDR-L3

<400> SEQUENCE: 26

Gln Gln Gly Phe Ala Thr Ser Asn Val Glu Asn Pro
1               5                   10

<210> SEQ ID NO 27
<211> LENGTH: 10
<212> TYPE: PRT
<213> ORGANISM: Artificial Sequence
<220> FEATURE:
<223> OTHER INFORMATION: EP19 CDR-H1

<400> SEQUENCE: 27

Gly Phe Ser Leu Asn Ser Asn Glu Ile Ser
1               5                   10

<210> SEQ ID NO 28
<211> LENGTH: 16
<212> TYPE: PRT
<213> ORGANISM: Artificial Sequence
<220> FEATURE:
<223> OTHER INFORMATION: EP19 CDR-H2

<400> SEQUENCE: 28

Tyr Ile Gly Asn Gly Gly Met Thr His Tyr Ala Ser Trp Ala Lys Gly
```

```
1               5                   10                  15

<210> SEQ ID NO 29
<211> LENGTH: 12
<212> TYPE: PRT
<213> ORGANISM: Artificial Sequence
<220> FEATURE:
<223> OTHER INFORMATION: EP19 CDR-H3

<400> SEQUENCE: 29

Ser Val Glu Tyr Thr Asp Leu Tyr Tyr Leu Asn Ile
1               5                   10

<210> SEQ ID NO 30
<211> LENGTH: 11
<212> TYPE: PRT
<213> ORGANISM: Artificial Sequence
<220> FEATURE:
<223> OTHER INFORMATION: EP19 CDR-L1

<400> SEQUENCE: 30

Gln Ala Ser Asp Asn Ile Tyr Arg Gly Leu Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: EP19 CDR-L2

<400> SEQUENCE: 31

Asp Ala Ser Thr Leu Gln Ser
1               5

<210> SEQ ID NO 32
<211> LENGTH: 13
<212> TYPE: PRT
<213> ORGANISM: Artificial Sequence
<220> FEATURE:
<223> OTHER INFORMATION: EP19 CDR-L3

<400> SEQUENCE: 32

Leu Gly Val Tyr Gly Tyr Ser Ser Asp Asp Gly Ala Ala
1               5                   10

<210> SEQ ID NO 33
<211> LENGTH: 11
<212> TYPE: PRT
<213> ORGANISM: Artificial Sequence
<220> FEATURE:
<223> OTHER INFORMATION: EP34 CDR-H1

<400> SEQUENCE: 33

Gly Phe Thr Ile Ser Arg Ser Tyr Trp Ile Cys
1               5                   10

<210> SEQ ID NO 34
<211> LENGTH: 18
<212> TYPE: PRT
<213> ORGANISM: Artificial Sequence
<220> FEATURE:
<223> OTHER INFORMATION: EP34 CDR-H2

<400> SEQUENCE: 34

Cys Ile Tyr Gly Asp Asn Asp Ile Thr Pro Leu Tyr Ala Asn Trp Ala
1               5                   10                  15
```

Lys Gly

<210> SEQ ID NO 35
<211> LENGTH: 10
<212> TYPE: PRT
<213> ORGANISM: Artificial Sequence
<220> FEATURE:
<223> OTHER INFORMATION: EP34 CDR-H3

<400> SEQUENCE: 35

Leu Gly Tyr Ala Asp Tyr Ala Tyr Asp Leu
1               5                   10

<210> SEQ ID NO 36
<211> LENGTH: 13
<212> TYPE: PRT
<213> ORGANISM: Artificial Sequence
<220> FEATURE:
<223> OTHER INFORMATION: EP34 CDR-L1

<400> SEQUENCE: 36

Gln Ser Ser Gln Ser Val Tyr Gly Asn Ile Trp Met Ala
1               5                   10

<210> SEQ ID NO 37
<211> LENGTH: 7
<212> TYPE: PRT
<213> ORGANISM: Artificial Sequence
<220> FEATURE:
<223> OTHER INFORMATION: EP34 CDR-L2

<400> SEQUENCE: 37

Gln Ala Ser Lys Leu Ala Ser
1               5

<210> SEQ ID NO 38
<211> LENGTH: 11
<212> TYPE: PRT
<213> ORGANISM: Artificial Sequence
<220> FEATURE:
<223> OTHER INFORMATION: EP34 CDR-L3

<400> SEQUENCE: 38

Gln Gly Asn Phe Asn Thr Gly Asp Arg Tyr Ala
1               5                   10

<210> SEQ ID NO 39
<211> LENGTH: 11
<212> TYPE: PRT
<213> ORGANISM: Artificial Sequence
<220> FEATURE:
<223> OTHER INFORMATION: EP35 CDR-H1

<400> SEQUENCE: 39

Gly Phe Ser Phe Ser Val Gly Tyr Trp Ile Cys
1               5                   10

<210> SEQ ID NO 40
<211> LENGTH: 18
<212> TYPE: PRT
<213> ORGANISM: Artificial Sequence
<220> FEATURE:
<223> OTHER INFORMATION: EP35 CDR-H2

<400> SEQUENCE: 40

Cys Ile Asp Ala Gly Thr Ser Gly Gly Thr Tyr Tyr Ala Thr Trp Ala

```
1               5                   10                  15
Lys Gly

<210> SEQ ID NO 41
<211> LENGTH: 11
<212> TYPE: PRT
<213> ORGANISM: Artificial Sequence
<220> FEATURE:
<223> OTHER INFORMATION: EP35 CDR-H3

<400> SEQUENCE: 41

Gly Val Ser Ser Asn Gly Tyr Tyr Phe Lys Leu
1               5                   10

<210> SEQ ID NO 42
<211> LENGTH: 11
<212> TYPE: PRT
<213> ORGANISM: Artificial Sequence
<220> FEATURE:
<223> OTHER INFORMATION: EP35 CDR-L1

<400> SEQUENCE: 42

Gln Ala Ser Gln Ser Ile Ser Asn Leu Leu Ala
1               5                   10

<210> SEQ ID NO 43
<211> LENGTH: 7
<212> TYPE: PRT
<213> ORGANISM: Artificial Sequence
<220> FEATURE:
<223> OTHER INFORMATION: EP35 CDR-L2

<400> SEQUENCE: 43

Ala Ala Ser Lys Leu Ala Ser
1               5

<210> SEQ ID NO 44
<211> LENGTH: 12
<212> TYPE: PRT
<213> ORGANISM: Artificial Sequence
<220> FEATURE:
<223> OTHER INFORMATION: EP35 CDR-L3

<400> SEQUENCE: 44

Gln Gln Gly Trp Ser His Thr Asn Val Asp Asn Thr
1               5                   10

<210> SEQ ID NO 45
<211> LENGTH: 10
<212> TYPE: PRT
<213> ORGANISM: Artificial Sequence
<220> FEATURE:
<223> OTHER INFORMATION: EP42 CDR-H1

<400> SEQUENCE: 45

Gly Ile Asp Leu Arg Asn Asp Ala Ile Ser
1               5                   10

<210> SEQ ID NO 46
<211> LENGTH: 16
<212> TYPE: PRT
<213> ORGANISM: Artificial Sequence
<220> FEATURE:
<223> OTHER INFORMATION: EP42 CDR-H2

<400> SEQUENCE: 46
```

```
Tyr Ile Ser Asp Trp Gly Ile Lys Tyr Tyr Ala Ser Trp Val Lys Gly
1               5                   10                  15

<210> SEQ ID NO 47
<211> LENGTH: 10
<212> TYPE: PRT
<213> ORGANISM: Artificial Sequence
<220> FEATURE:
<223> OTHER INFORMATION: EP42 CDR-H3

<400> SEQUENCE: 47

Gly Ala Pro Gly Ala Gly Asp Asn Gly Ile
1               5                   10

<210> SEQ ID NO 48
<211> LENGTH: 13
<212> TYPE: PRT
<213> ORGANISM: Artificial Sequence
<220> FEATURE:
<223> OTHER INFORMATION: EP42 CDR-L1

<400> SEQUENCE: 48

Gln Ser Thr Glu Ser Val Tyr Lys Asn Asn Tyr Leu Ala
1               5                   10

<210> SEQ ID NO 49
<211> LENGTH: 7
<212> TYPE: PRT
<213> ORGANISM: Artificial Sequence
<220> FEATURE:
<223> OTHER INFORMATION: EP42 CDR-L2

<400> SEQUENCE: 49

Asp Ala Ser Thr Leu Ala Ser
1               5

<210> SEQ ID NO 50
<211> LENGTH: 13
<212> TYPE: PRT
<213> ORGANISM: Artificial Sequence
<220> FEATURE:
<223> OTHER INFORMATION: EP42 CDR-L3

<400> SEQUENCE: 50

Ala Gly Tyr Tyr Arg Ser Gly Phe Gly Thr Ala Asn Gly
1               5                   10

<210> SEQ ID NO 51
<211> LENGTH: 122
<212> TYPE: PRT
<213> ORGANISM: Artificial Sequence
<220> FEATURE:
<223> OTHER INFORMATION: EP43min VH

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Gly
            20                  25                  30

Ala Met Ser Trp Val Arg Gln Ala Pro Gly Lys Gly Leu Glu Trp Val
        35                  40                  45

Ser Val Ile Ile Ser Ser Gly Ala Thr Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80
```

```
Gln Met Asn Ser Leu Arg Ala Glu Asp Thr Ala Val Tyr Tyr Cys Ala
                85                  90                  95

Lys Gly Gly Pro Asp Asp Ser Asn Ser Met Gly Thr Phe Asp Pro Trp
            100                 105                 110

Gly Gln Gly Thr Leu Val Thr Val Ser Ser
            115                 120
```

<210> SEQ ID NO 52
<211> LENGTH: 111
<212> TYPE: PRT
<213> ORGANISM: Artificial Sequence
<220> FEATURE:
<223> OTHER INFORMATION: EP43min VL

<400> SEQUENCE: 52

```
Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Gly Ala Ser Arg Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly
            100                 105                 110
```

<210> SEQ ID NO 53
<211> LENGTH: 122
<212> TYPE: PRT
<213> ORGANISM: Artificial Sequence
<220> FEATURE:
<223> OTHER INFORMATION: EP43max VH

<400> SEQUENCE: 53

```
Glu Val Gln Leu Val Glu Ser Gly Gly Leu Val Gln Pro Gly Gly
1               5                   10                  15

Ser Leu Arg Leu Ser Cys Thr Val Ser Gly Phe Ser Leu Ser Ser Gly
            20                  25                  30

Ala Met Ser Trp Val Arg Gln Ala Pro Gly Lys Gly Leu Glu Trp Val
        35                  40                  45

Gly Val Ile Ile Ser Ser Gly Ala Thr Tyr Tyr Ala Ser Trp Ala Lys
    50                  55                  60

Gly Arg Phe Thr Ile Ser Lys Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gly Gly Pro Asp Asp Ser Asn Ser Met Gly Thr Phe Asp Pro Trp
            100                 105                 110

Gly Gln Gly Thr Leu Val Thr Val Ser Ser
            115                 120
```

<210> SEQ ID NO 54
<211> LENGTH: 111
<212> TYPE: PRT

<213> ORGANISM: Artificial Sequence
<220> FEATURE:
<223> OTHER INFORMATION: EP43max VL

<400> SEQUENCE: 54

```
Glu Ile Val Met Thr Gln Ser Pro Ser Thr Leu Ser Ala Ser Val Gly
1               5                   10                  15

Asp Arg Val Ile Ile Lys Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Gly Ala Ser Arg Leu Ala Ser Gly Phe Pro Ser Arg Phe Ser Gly
50                  55                  60

Ser Gly Ser Gly Ala Glu Phe Thr Leu Thr Ile Ser Gly Leu Glu Pro
65                  70                  75                  80

Ala Asp Phe Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly
            100                 105                 110
```

<210> SEQ ID NO 55
<211> LENGTH: 122
<212> TYPE: PRT
<213> ORGANISM: Artificial Sequence
<220> FEATURE:
<223> OTHER INFORMATION: EP43maxDHP VH

<400> SEQUENCE: 55

```
Glu Val Gln Leu Val Glu Ser Gly Gly Gly Ser Val Gln Pro Gly Gly
1               5                   10                  15

Ser Leu Arg Leu Ser Cys Thr Val Ser Gly Phe Ser Leu Ser Ser Gly
            20                  25                  30

Ala Met Ser Trp Val Arg Gln Ala Pro Gly Lys Gly Leu Glu Trp Val
        35                  40                  45

Gly Val Ile Ile Ser Ser Gly Ala Thr Tyr Tyr Ala Ser Trp Ala Lys
50                  55                  60

Gly Arg Phe Thr Ile Ser Lys Asp Thr Ser Lys Asn Thr Val Tyr Leu
65                  70                  75                  80

Gln Met Asn Ser Leu Arg Ala Glu Asp Thr Ala Thr Tyr Tyr Cys Ala
                85                  90                  95

Arg Gly Gly Pro Asp Asp Ser Asn Ser Met Gly Thr Phe Asp Pro Trp
            100                 105                 110

Gly Gln Gly Thr Ser Val Thr Val Ser Ser
        115                 120
```

<210> SEQ ID NO 56
<211> LENGTH: 111
<212> TYPE: PRT
<213> ORGANISM: Artificial Sequence
<220> FEATURE:
<223> OTHER INFORMATION: EP43minmaxVL:T22K VL

<400> SEQUENCE: 56

```
Glu Ile Val Met Thr Gln Ser Pro Ser Thr Leu Ser Ala Ser Val Gly
1               5                   10                  15

Asp Arg Val Ile Ile Lys Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45
```

-continued

Tyr Gly Ala Ser Arg Leu Ala Ser Gly Val Pro Ser Arg Phe Ser Gly
            50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly
                100                 105                 110

<210> SEQ ID NO 57
<211> LENGTH: 111
<212> TYPE: PRT
<213> ORGANISM: Artificial Sequence
<220> FEATURE:
<223> OTHER INFORMATION: EP43minmaxVL:V58F VL

<400> SEQUENCE: 57

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Asp Trp
                20                  25                  30

Leu Ala Trp Tyr Gln Gln Lys Pro Gly Lys Ala Pro Lys Leu Leu Ile
            35                  40                  45

Tyr Gly Ala Ser Arg Leu Ala Ser Gly Phe Pro Ser Arg Phe Ser Gly
            50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly
                100                 105                 110

<210> SEQ ID NO 58
<211> LENGTH: 111
<212> TYPE: PRT
<213> ORGANISM: Artificial Sequence
<220> FEATURE:
<223> OTHER INFORMATION: EP43minmaxVL:Q79E VL

<400> SEQUENCE: 58

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Asp Trp
                20                  25                  30

Leu Ala Trp Tyr Gln Gln Lys Pro Gly Lys Ala Pro Lys Leu Leu Ile
            35                  40                  45

Tyr Gly Ala Ser Arg Leu Ala Ser Gly Val Pro Ser Arg Phe Ser Gly
            50                  55                  60

Ser Gly Ser Gly Ala Glu Phe Thr Leu Thr Ile Ser Ser Leu Glu Pro
65                  70                  75                  80

Asp Asp Phe Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly
                100                 105                 110

<210> SEQ ID NO 59
<211> LENGTH: 111
<212> TYPE: PRT

<213> ORGANISM: Artificial Sequence
<220> FEATURE:
<223> OTHER INFORMATION: EP43minmaxVL:D81A VL

<400> SEQUENCE: 59

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Gly Ala Ser Arg Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Ala Asp Phe Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly
            100                 105                 110

<210> SEQ ID NO 60
<211> LENGTH: 118
<212> TYPE: PRT
<213> ORGANISM: Artificial Sequence
<220> FEATURE:
<223> OTHER INFORMATION: EP1min VH

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Asp
            20                  25                  30

Ala Ile Ser Trp Val Arg Gln Ala Pro Gly Lys Gly Leu Glu Trp Val
        35                  40                  45

Ser Tyr Ile Ser Asp Trp Ser Ile Arg Tyr Tyr Ala Asn Trp Ala Gln
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Ala Pro Gly Ala Gly Asp Asn Gly Ile Trp Gly Gln Gly Thr
            100                 105                 110

Leu Val Thr Val Ser Ser
        115

<210> SEQ ID NO 61
<211> LENGTH: 115
<212> TYPE: PRT
<213> ORGANISM: Artificial Sequence
<220> FEATURE:
<223> OTHER INFORMATION: EP1min VL

<400> SEQUENCE: 61

Glu Ile Val Met Thr Gln Ser Pro Ser Thr Leu Ser Ala Ser Val Gly
1               5                   10                  15

Asp Arg Val Ile Ile Thr Cys Gln Ser Thr Glu Ser Val Tyr Lys Asn
            20                  25                  30

Asn Tyr Leu Ala Trp Tyr Gln Gln Lys Pro Gly Lys Ala Pro Lys Leu
        35                  40                  45

Leu Ile Tyr Asp Ala Ser Thr Leu Ala Ser Gly Val Pro Ser Arg Phe
            50                  55                  60

Ser Gly Ser Gly Ser Gly Ala Glu Phe Thr Leu Thr Ile Ser Ser Leu
 65                  70                  75                  80

Gln Pro Asp Asp Phe Ala Thr Tyr Tyr Cys Ala Gly Tyr Tyr Arg Ser
                85                  90                  95

Gly Ser Gly Thr Ala Asn Gly Ser Phe Gly Gln Gly Thr Lys Leu Thr
            100                 105                 110

Val Leu Gly
        115

<210> SEQ ID NO 62
<211> LENGTH: 118
<212> TYPE: PRT
<213> ORGANISM: Artificial Sequence
<220> FEATURE:
<223> OTHER INFORMATION: EP1max VH

<400> SEQUENCE: 62

Glu Val Gln Leu Val Glu Ser Gly Gly Gly Ser Val Gln Pro Gly Gly
 1               5                  10                  15

Ser Leu Arg Leu Ser Cys Thr Val Ser Gly Ile Asp Leu Ser Asn Asp
            20                  25                  30

Ala Ile Ser Trp Val Arg Gln Ala Pro Gly Lys Gly Leu Glu Trp Val
        35                  40                  45

Ala Tyr Ile Ser Asp Trp Ser Ile Arg Tyr Tyr Ala Asn Trp Ala Gln
    50                  55                  60

Gly Arg Phe Thr Ile Ser Lys Asp Thr Ser Lys Asn Thr Val Tyr Leu
 65                  70                  75                  80

Gln Met Asn Ser Leu Arg Ala Glu Asp Thr Ala Thr Tyr Tyr Cys Ala
                85                  90                  95

Arg Gly Ala Pro Gly Ala Gly Asp Asn Gly Ile Trp Gly Gln Gly Thr
            100                 105                 110

Thr Val Thr Val Ser Ser
        115

<210> SEQ ID NO 63
<211> LENGTH: 115
<212> TYPE: PRT
<213> ORGANISM: Artificial Sequence
<220> FEATURE:
<223> OTHER INFORMATION: EP1max VL

<400> SEQUENCE: 63

Glu Ile Val Met Thr Gln Ser Pro Ser Thr Leu Ser Ala Ser Val Gly
 1               5                  10                  15

Asp Arg Val Ile Ile Thr Cys Gln Ser Thr Glu Ser Val Tyr Lys Asn
            20                  25                  30

Asn Tyr Leu Ala Trp Tyr Gln Gln Lys Pro Gly Lys Ala Pro Lys Leu
        35                  40                  45

Leu Ile Tyr Asp Ala Ser Thr Leu Ala Ser Gly Val Pro Ser Arg Phe
    50                  55                  60

Ser Gly Ser Gly Ser Gly Thr Glu Phe Thr Leu Thr Ile Ser Ser Leu
 65                  70                  75                  80

Gln Pro Asp Asp Phe Ala Thr Tyr Tyr Cys Ala Gly Tyr Tyr Arg Ser
                85                  90                  95

Gly Ser Gly Thr Ala Asn Gly Ser Phe Gly Gln Gly Thr Lys Leu Thr

Val Leu Gly
        115

<210> SEQ ID NO 64
<211> LENGTH: 121
<212> TYPE: PRT
<213> ORGANISM: Artificial Sequence
<220> FEATURE:
<223> OTHER INFORMATION: EP6min VH

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Arg Tyr
            20                  25                  30

Gly Val Ser Trp Val Arg Gln Ala Pro Gly Lys Gly Leu Glu Trp Val
        35                  40                  45

Ser Thr Ile Gly Glu Ala Gly Arg Ala Tyr Tyr Ala Asn Trp Ala Arg
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Glu Val Phe Asn Asn Gly Trp Gly Ala Phe Asn Ile Trp Gly
            100                 105                 110

Gln Gly Thr Leu Val Thr Val Ser Ser
        115                 120

<210> SEQ ID NO 65
<211> LENGTH: 111
<212> TYPE: PRT
<213> ORGANISM: Artificial Sequence
<220> FEATURE:
<223> OTHER INFORMATION: EP6min VL

<400> SEQUENCE: 65

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ser Ile Tyr Ser Gly
            20                  25                  30

Leu Ala Trp Tyr Gln Gln Lys Pro Gly Lys Ala Pro Lys Leu Leu Ile
        35                  40                  45

Tyr Gln Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Gly Phe Gly Thr Ser Asn
                85                  90                  95

Val Glu Asn Pro Phe Gly Gln Gly Thr Lys Leu Thr Val Leu Gly
            100                 105                 110

<210> SEQ ID NO 66
<211> LENGTH: 121
<212> TYPE: PRT
<213> ORGANISM: Artificial Sequence
<220> FEATURE:
<223> OTHER INFORMATION: EP6max VH

<400> SEQUENCE: 66

-continued

Glu Val Gln Leu Val Glu Ser Gly Gly Gly Leu Val Gln Pro Gly Gly
1               5                   10                  15

Ser Leu Arg Leu Ser Cys Thr Val Ser Gly Phe Ser Leu Ser Arg Tyr
            20                  25                  30

Gly Val Ser Trp Val Arg Gln Ala Pro Gly Lys Gly Leu Glu Trp Val
            35                  40                  45

Gly Thr Ile Gly Glu Ala Gly Arg Ala Tyr Tyr Ala Asn Trp Ala Arg
50                      55                  60

Ser Arg Ser Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gly Glu Val Phe Asn Asn Gly Trp Gly Ala Phe Asn Ile Trp Gly
            100                 105                 110

Gln Gly Thr Leu Val Thr Val Ser Ser
            115                 120

<210> SEQ ID NO 67
<211> LENGTH: 111
<212> TYPE: PRT
<213> ORGANISM: Artificial Sequence
<220> FEATURE:
<223> OTHER INFORMATION: EP6max VL

<400> SEQUENCE: 67

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ser Ile Tyr Ser Gly
            20                  25                  30

Leu Ala Trp Tyr Gln Gln Lys Pro Gly Lys Ala Pro Lys Leu Leu Ile
            35                  40                  45

Tyr Gln Ala Ser Thr Leu Ala Ser Gly Val Pro Ser Arg Phe Ser Gly
50                  55                  60

Ser Gly Ser Gly Thr Asp Phe Thr Leu Ala Ile Ser Ser Leu Gln Pro
65                  70                  75                  80

Asp Asp Phe Ala Thr Tyr Tyr Cys Gln Gln Gly Phe Gly Thr Ser Asn
                85                  90                  95

Val Glu Asn Pro Phe Gly Gln Gly Thr Lys Leu Thr Val Leu Gly
            100                 105                 110

<210> SEQ ID NO 68
<211> LENGTH: 121
<212> TYPE: PRT
<213> ORGANISM: Artificial Sequence
<220> FEATURE:
<223> OTHER INFORMATION: EP15min VH

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Val Ser Trp Val Arg Gln Ala Pro Gly Lys Gly Leu Glu Trp Val
            35                  40                  45

Ser Ala Ile Gly Glu Thr Gly Arg Ala Tyr Tyr Ala Asn Trp Ala Lys
50                  55                  60

Ser Arg Phe Thr Ile Ser Arg Asp Asn Ser Lys Asn Thr Leu Tyr Leu 65                  70                  75                  80
Gln Met Asn Ser Leu Arg Ala Glu Asp Thr Ala Val Tyr Tyr Cys Ala
                 85                  90                  95

Lys Gly Glu Glu Phe Asn Asn Gly Trp Gly Ala Phe Asn Ile Trp Gly
            100                 105                 110

Gln Gly Thr Leu Val Thr Val Ser Ser
            115                 120

<210> SEQ ID NO 69
<211> LENGTH: 111
<212> TYPE: PRT
<213> ORGANISM: Artificial Sequence
<220> FEATURE:
<223> OTHER INFORMATION: EP15min VL

<400> SEQUENCE: 69

Glu Ile Val Met Thr Gln Ser Pro Ser Thr Leu Ser Ala Ser Val Gly
1               5                  10                  15

Asp Arg Val Ile Ile Thr Cys Gln Ala Ser Glu Asn Ile Tyr Thr Ser
            20                  25                  30

Leu Ala Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Gly Phe Ala Thr Ser Asn
                85                  90                  95

Val Glu Asn Pro Phe Gly Gln Gly Thr Lys Leu Thr Val Leu Gly
            100                 105                 110

<210> SEQ ID NO 70
<211> LENGTH: 121
<212> TYPE: PRT
<213> ORGANISM: Artificial Sequence
<220> FEATURE:
<223> OTHER INFORMATION: EP15max VH

<400> SEQUENCE: 70

Glu Val Gln Leu Val Glu Ser Gly Gly Gly Ser Val Gln Pro Gly Gly
1               5                  10                  15

Ser Leu Arg Leu Ser Cys Thr Val Ser Gly Phe Ser Leu Ser Arg Tyr
            20                  25                  30

Gly Val Ser Trp Val Arg Gln Ala Pro Gly Lys Gly Leu Glu Trp Val
        35                  40                  45

Gly Ala Ile Gly Glu Thr Gly Arg Ala Tyr Tyr Ala Asn Trp Ala Lys
    50                  55                  60

Ser Arg Ser Thr Ile Ser Arg Asp Thr Ser Lys Asn Thr Val Tyr Leu
65                  70                  75                  80

Gln Met Asn Ser Leu Arg Ala Glu Asp Thr Ala Thr Tyr Tyr Cys Ala
                85                  90                  95

Arg Gly Glu Glu Phe Asn Asn Gly Trp Gly Ala Phe Asn Ile Trp Gly
            100                 105                 110

Gln Gly Thr Thr Val Thr Val Ser Ser
            115                 120

<210> SEQ ID NO 71
<211> LENGTH: 111

<212> TYPE: PRT
<213> ORGANISM: Artificial Sequence
<220> FEATURE:
<223> OTHER INFORMATION: EP15max VL

<400> SEQUENCE: 71

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Asn Ile Tyr Thr Ser
            20                  25                  30

Leu Ala Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Phe Ala Thr Ser Asn
                85                  90                  95

Val Glu Asn Pro Phe Gly Gln Gly Thr Lys Leu Thr Val Leu Gly
            100                 105                 110

<210> SEQ ID NO 72
<211> LENGTH: 20
<212> TYPE: PRT
<213> ORGANISM: Artificial Sequence
<220> FEATURE:
<223> OTHER INFORMATION: glycin-serine linker

<400> SEQUENCE: 72

Gly Gly Gly Gly Ser Gly Gly Gly Ser Gly Gly Gly Gly Ser Gly
1               5                   10                  15

Gly Gly Gly Ser
            20

<210> SEQ ID NO 73
<211> LENGTH: 120
<212> TYPE: PRT
<213> ORGANISM: Artificial Sequence
<220> FEATURE:
<223> OTHER INFORMATION: EP19maxmod

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Thr Val Ser Gly Phe Ser Leu Asn Ser Asn
            20                  25                  30

Glu Ile Ser Trp Val Arg Gln Ala Pro Gly Lys Gly Leu Glu Trp Val
        35                  40                  45

Gly Tyr Ile Gly Asn Gly Gly Met Thr His Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Ser Ser Val Glu Tyr Thr Asp Leu Tyr Tyr Leu Asn Ile Trp Gly Gln
            100                 105                 110

Gly Thr Leu Val Thr Val Ser Ser
        115                 120

<210> SEQ ID NO 74
<211> LENGTH: 112
<212> TYPE: PRT
<213> ORGANISM: Artificial Sequence
<220> FEATURE:
<223> OTHER INFORMATION: EP19maxmod VL

<400> SEQUENCE: 74

```
Glu Ile Val Met Thr Gln Ser Pro Ser Thr Leu Ser Ala Ser Val Gly
1               5                   10                  15

Asp Arg Val Ile Ile Thr Cys Gln Ala Ser Asp Asn Ile Tyr Arg Gly
            20                  25                  30

Leu Ala Trp Tyr Gln Gln Lys Pro Gly Lys Ala Pro Lys Leu Leu Ile
        35                  40                  45

Tyr Asp Ala Ser Thr Leu Gln Ser Gly Val Pro Ser Arg Phe Ser Gly
50                  55                  60

Ser Gly Ser Gly Thr Gln Phe Thr Leu Thr Ile Ser Ser Leu Gln Pro
65                  70                  75                  80

Asp Asp Phe Ala Thr Tyr Tyr Cys Leu Gly Val Tyr Gly Tyr Ser Ser
                85                  90                  95

Asp Asp Gly Ala Ala Phe Gly Gln Gly Thr Lys Leu Thr Val Leu Gly
            100                 105                 110
```

<210> SEQ ID NO 75
<211> LENGTH: 120
<212> TYPE: PRT
<213> ORGANISM: Artificial Sequence
<220> FEATURE:
<223> OTHER INFORMATION: EP19minmod VH

<400> SEQUENCE: 75

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asn Ser Asn
            20                  25                  30

Glu Ile Ser Trp Val Arg Gln Ala Pro Gly Lys Gly Leu Glu Trp Val
        35                  40                  45

Ser Tyr Ile Gly Asn Gly Gly Met Thr His Tyr Ala Ser Trp Ala Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ser Val Glu Tyr Thr Asp Leu Tyr Tyr Leu Asn Ile Trp Gly Gln
            100                 105                 110

Gly Thr Leu Val Thr Val Ser Ser
        115                 120
```

<210> SEQ ID NO 76
<211> LENGTH: 112
<212> TYPE: PRT
<213> ORGANISM: Artificial Sequence
<220> FEATURE:
<223> OTHER INFORMATION: EP19minmod VL

<400> SEQUENCE: 76

```
Glu Ile Val Met Thr Gln Ser Pro Ser Thr Leu Ser Ala Ser Val Gly
1               5                   10                  15

Asp Arg Val Ile Ile Thr Cys Gln Ala Ser Asp Asn Ile Tyr Arg Gly
            20                  25                  30
```

Leu Ala Trp Tyr Gln Gln Lys Pro Gly Lys Ala Pro Lys Leu Leu Ile
            35                  40                  45

Tyr Asp Ala Ser Thr Leu Gln Ser Gly Val Pro Ser Arg Phe Ser Gly
        50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Leu Gly Val Tyr Gly Tyr Ser Ser
                85                  90                  95

Asp Asp Gly Ala Ala Phe Gly Gln Gly Thr Lys Leu Thr Val Leu Gly
            100                 105                 110

<210> SEQ ID NO 77
<211> LENGTH: 121
<212> TYPE: PRT
<213> ORGANISM: Artificial Sequence
<220> FEATURE:
<223> OTHER INFORMATION: EP34min VH

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Arg Ser
            20                  25                  30

Tyr Trp Ile Cys Trp Val Arg Gln Ala Pro Gly Lys Gly Leu Glu Trp
        35                  40                  45

Val Ser Cys Ile Tyr Gly Asp Asn Asp Ile Thr Pro Leu Tyr Ala Asn
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Leu Gly Tyr Ala Asp Tyr Ala Tyr Asp Leu Trp Gly
            100                 105                 110

Gln Gly Thr Leu Val Thr Val Ser Ser
        115                 120

<210> SEQ ID NO 78
<211> LENGTH: 112
<212> TYPE: PRT
<213> ORGANISM: Artificial Sequence
<220> FEATURE:
<223> OTHER INFORMATION: EP34min VL

<400> SEQUENCE: 78

Glu Ile Val Met Thr Gln Ser Pro Ser Thr Leu Ser Ala Ser Val Gly
1               5                   10                  15

Asp Arg Val Ile Ile Thr Cys Gln Ser Ser Gln Ser Val Tyr Gly Asn
            20                  25                  30

Ile Trp Met Ala Trp Tyr Gln Gln Lys Pro Gly Lys Ala Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Ala Glu Phe Thr Leu Thr Ile Ser Ser Leu
65                  70                  75                  80

Gln Pro Asp Asp Phe Ala Thr Tyr Tyr Cys Gln Gly Asn Phe Asn Thr
                85                  90                  95

Gly Asp Arg Tyr Ala Phe Gly Gln Gly Thr Lys Leu Thr Val Leu Gly

-continued

```
              100                 105                 110
```

<210> SEQ ID NO 79
<211> LENGTH: 121
<212> TYPE: PRT
<213> ORGANISM: Artificial Sequence
<220> FEATURE:
<223> OTHER INFORMATION: EP34max VH

<400> SEQUENCE: 79

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Ile Ser Arg Ser
            20                  25                  30

Tyr Trp Ile Cys Trp Val Arg Gln Ala Pro Gly Lys Gly Leu Glu Trp
        35                  40                  45

Val Ala Cys Ile Tyr Gly Asp Asn Asp Ile Thr Pro Leu Tyr Ala Asn
    50                  55                  60

Trp Ala Lys Gly Arg Phe Pro Val Ser Thr Asp Thr Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Leu Gly Tyr Ala Asp Tyr Ala Tyr Asp Leu Trp Gly
            100                 105                 110

Gln Gly Thr Leu Val Thr Val Ser Ser
        115                 120
```

<210> SEQ ID NO 80
<211> LENGTH: 112
<212> TYPE: PRT
<213> ORGANISM: Artificial Sequence
<220> FEATURE:
<223> OTHER INFORMATION: EP34max VL

<400> SEQUENCE: 80

```
Glu Ile Val Met Thr Gln Ser Pro Ser Thr Leu Ser Ala Ser Leu Gly
1               5                   10                  15

Asp Arg Val Ile Ile Thr Cys Gln Ser Ser Gln Ser Val Tyr Gly Asn
            20                  25                  30

Ile Trp Met Ala Trp Tyr Gln Gln Lys Ser Gly Lys Ala Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Ala Glu Phe Ser Leu Thr Ile Ser Ser Leu
65                  70                  75                  80

Gln Pro Asp Asp Phe Ala Thr Tyr Tyr Cys Gln Gly Asn Phe Asn Thr
                85                  90                  95

Gly Asp Arg Tyr Ala Phe Gly Gln Gly Thr Lys Leu Thr Val Leu Gly
            100                 105                 110
```

<210> SEQ ID NO 81
<211> LENGTH: 122
<212> TYPE: PRT
<213> ORGANISM: Artificial Sequence
<220> FEATURE:
<223> OTHER INFORMATION: EP35min VH

<400> SEQUENCE: 81

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Val Gly
            20                  25                  30

Tyr Trp Ile Cys Trp Val Arg Gln Ala Pro Gly Lys Gly Leu Glu Trp
        35                  40                  45

Val Ser Cys Ile Asp Ala Gly Thr Ser Gly Gly Thr Tyr Tyr Ala Thr
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Gly Val Ser Ser Asn Gly Tyr Tyr Phe Lys Leu Trp
            100                 105                 110

Gly Gln Gly Thr Leu Val Thr Val Ser Ser
            115                 120
```

<210> SEQ ID NO 82
<211> LENGTH: 111
<212> TYPE: PRT
<213> ORGANISM: Artificial Sequence
<220> FEATURE:
<223> OTHER INFORMATION: EP35min VL

<400> SEQUENCE: 82

```
Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Asn Leu
            20                  25                  30

Leu Ala Trp Tyr Gln Gln Lys Pro Gly Lys Ala Pro Lys Leu Leu Ile
        35                  40                  45

Tyr Ala Ala Ser Lys Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Gly Trp Ser His Thr Asn
                85                  90                  95

Val Asp Asn Thr Phe Gly Gln Gly Thr Lys Leu Thr Val Leu Gly
            100                 105                 110
```

<210> SEQ ID NO 83
<211> LENGTH: 122
<212> TYPE: PRT
<213> ORGANISM: Artificial Sequence
<220> FEATURE:
<223> OTHER INFORMATION: EP35max VH

<400> SEQUENCE: 83

```
Glu Val Gln Leu Val Glu Ser Gly Gly Gly Ser Val Gln Pro Gly Gly
1               5                   10                  15

Ser Leu Arg Leu Ser Cys Thr Ala Ser Gly Phe Ser Phe Ser Val Gly
            20                  25                  30

Tyr Trp Ile Cys Trp Val Arg Gln Ala Pro Gly Lys Gly Leu Glu Trp
        35                  40                  45

Val Ala Cys Ile Asp Ala Gly Thr Ser Gly Gly Thr Tyr Tyr Ala Thr
    50                  55                  60

Trp Ala Lys Gly Arg Phe Thr Ile Ser Lys Asp Thr Ser Lys Asn Thr
65                  70                  75                  80

Val Tyr Leu Gln Met Asn Ser Leu Arg Ala Glu Asp Thr Ala Thr Tyr
```

-continued

```
                85                  90                  95
Tyr Cys Ala Arg Gly Val Ser Ser Asn Gly Tyr Tyr Phe Lys Leu Trp
            100                 105                 110

Gly Gln Gly Thr Thr Val Thr Val Ser Ser
        115                 120

<210> SEQ ID NO 84
<211> LENGTH: 111
<212> TYPE: PRT
<213> ORGANISM: Artificial Sequence
<220> FEATURE:
<223> OTHER INFORMATION: EP35max VL

<400> SEQUENCE: 84

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Asn Leu
            20                  25                  30

Leu Ala Trp Tyr Gln Gln Lys Pro Gly Lys Ala Pro Lys Leu Leu Ile
        35                  40                  45

Val Ala Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Trp Ser His Thr Asn
                85                  90                  95

Val Asp Asn Thr Phe Gly Gln Gly Thr Lys Leu Thr Val Leu Gly
            100                 105                 110

<210> SEQ ID NO 85
<211> LENGTH: 118
<212> TYPE: PRT
<213> ORGANISM: Artificial Sequence
<220> FEATURE:
<223> OTHER INFORMATION: EP42min VH

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Asp
            20                  25                  30

Ala Ile Ser Trp Val Arg Gln Ala Pro Gly Lys Gly Leu Glu Trp Val
        35                  40                  45

Ser Tyr Ile Ser Asp Trp Gly Ile Lys Tyr Tyr Ala Ser Trp Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Ala Pro Gly Ala Gly Asp Asn Gly Ile Trp Gly Gln Gly Thr
            100                 105                 110

Leu Val Thr Val Ser Ser
        115

<210> SEQ ID NO 86
<211> LENGTH: 115
<212> TYPE: PRT
<213> ORGANISM: Artificial Sequence
<220> FEATURE:
```

<223> OTHER INFORMATION: EP42min VL

<400> SEQUENCE: 86

Glu Ile Val Met Thr Gln Ser Pro Ser Thr Leu Ser Ala Ser Val Gly
1               5                   10                  15

Asp Arg Val Ile Ile Thr Cys Gln Ser Thr Glu Ser Val Tyr Lys Asn
            20                  25                  30

Asn Tyr Leu Ala Trp Tyr Gln Gln Lys Pro Gly Lys Ala Pro Lys Leu
        35                  40                  45

Leu Ile Tyr Asp Ala Ser Thr Leu Ala Ser Gly Val Pro Ser Arg Phe
    50                  55                  60

Ser Gly Ser Gly Ser Gly Ala Glu Phe Thr Leu Thr Ile Ser Ser Leu
65                  70                  75                  80

Gln Pro Asp Asp Phe Ala Thr Tyr Tyr Cys Ala Gly Tyr Tyr Arg Ser
                85                  90                  95

Gly Phe Gly Thr Ala Asn Gly Ser Phe Gly Gln Gly Thr Lys Leu Thr
            100                 105                 110

Val Leu Gly
        115

<210> SEQ ID NO 87
<211> LENGTH: 118
<212> TYPE: PRT
<213> ORGANISM: Artificial Sequence
<220> FEATURE:
<223> OTHER INFORMATION: EP42max VH

<400> SEQUENCE: 87

Glu Val Gln Leu Val Glu Ser Gly Gly Gly Ser Val Gln Pro Gly Gly
1               5                   10                  15

Ser Leu Arg Leu Ser Cys Thr Val Ser Gly Ile Asp Leu Arg Asn Asp
            20                  25                  30

Ala Ile Ser Trp Val Arg Gln Ala Pro Gly Lys Gly Leu Glu Trp Val
        35                  40                  45

Ser Tyr Ile Ser Asp Trp Gly Ile Lys Tyr Tyr Ala Ser Trp Val Lys
    50                  55                  60

Gly Arg Phe Thr Ile Ser Lys Asp Thr Ser Lys Asn Thr Val Tyr Leu
65                  70                  75                  80

Gln Met Asn Ser Leu Arg Ala Glu Asp Thr Ala Thr Tyr Tyr Cys Ala
                85                  90                  95

Arg Gly Ala Pro Gly Ala Gly Asp Asn Gly Ile Trp Gly Gln Gly Thr
            100                 105                 110

Thr Val Thr Val Ser Ser
        115

<210> SEQ ID NO 88
<211> LENGTH: 115
<212> TYPE: PRT
<213> ORGANISM: Artificial Sequence
<220> FEATURE:
<223> OTHER INFORMATION: EP42max VL

<400> SEQUENCE: 88

Glu Ile Val Met Thr Gln Ser Pro Ser Thr Leu Ser Ala Ser Val Gly
1               5                   10                  15

Asp Arg Val Ile Ile Thr Cys Gln Ser Thr Glu Ser Val Tyr Lys Asn
            20                  25                  30

Asn Tyr Leu Ala Trp Tyr Gln Gln Lys Pro Gly Lys Ala Pro Lys Leu

```
                35                  40                  45
Leu Ile Tyr Asp Ala Ser Thr Leu Ala Ser Gly Val Pro Ser Arg Phe
 50                  55                  60

Ser Gly Ser Gly Ser Gly Thr Glu Phe Thr Leu Thr Ile Ser Ser Leu
 65                  70                  75                  80

Gln Pro Asp Asp Phe Ala Thr Tyr Tyr Cys Ala Gly Tyr Tyr Arg Ser
                 85                  90                  95

Gly Phe Gly Thr Ala Asn Gly Ser Phe Gly Gln Gly Thr Lys Leu Thr
                100                 105                 110

Val Leu Gly
        115

<210> SEQ ID NO 89
<211> LENGTH: 232
<212> TYPE: PRT
<213> ORGANISM: Artificial Sequence
<220> FEATURE:
<223> OTHER INFORMATION: variable heavy chain framework of rFW1.4
<220> FEATURE:
<221> NAME/KEY: MISC_FEATURE
<222> LOCATION: (26)..(75)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (90)..(139)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (172)..(221)
<223> OTHER INFORMATION: X can be any naturally occurring amino acid.
      at least three and up to 50 amino acids can be present

<400> SEQUENCE: 89

Glu Val Gln Leu Val Glu Ser Gly Gly Gly Leu Val Gln Pro Gly Gly
 1               5                  10                  15

Ser Leu Arg Leu Ser Cys Thr Ala Ser Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Trp Val Arg Gln Ala
 65                  70                  75                  80

Pro Gly Lys Gly Leu Glu Trp Val Gly Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Arg Phe Thr Ile Ser
        130                 135                 140

Arg Asp Thr Ser Lys Asn Thr Val Tyr Leu Gln Met Asn Ser Leu Arg
145                 150                 155                 160

Ala Glu Asp Thr Ala Val Tyr Tyr Cys Ala Arg Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa Xaa Xaa
```

```
                195                 200                 205
Xaa Xaa Xaa Xaa Xaa Xaa Xaa Xaa Xaa Xaa Xaa Xaa Trp Gly Gln
    210                 215                 220

Gly Thr Leu Val Thr Val Ser Ser
225                 230

<210> SEQ ID NO 90
<211> LENGTH: 232
<212> TYPE: PRT
<213> ORGANISM: Artificial Sequence
<220> FEATURE:
<223> OTHER INFORMATION: variable heavy chain framework of rFW1.4(V2)
<220> FEATURE:
<221> NAME/KEY: MISC_FEATURE
<222> LOCATION: (26)..(75)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (90)..(139)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (172)..(221)
<223> OTHER INFORMATION: X can be any naturally occurring amino acid.
      at least three and up to 50 amino acids can be present

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Thr Val Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Trp Val Arg Gln Ala
65                  70                  75                  80

Pro Gly Lys Gly Leu Glu Trp Val Gly Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Arg Phe Thr Ile Ser
    130                 135                 140

Lys Asp Thr Ser Lys Asn Thr Val Tyr Leu Gln Met Asn Ser Leu Arg
145                 150                 155                 160

Ala Glu Asp Thr Ala Val Tyr Tyr Cys Ala Arg Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Trp Gly Gln
    210                 215                 220

Gly Thr Leu Val Thr Val Ser Ser
225                 230
```

```
<210> SEQ ID NO 91
<211> LENGTH: 231
<212> TYPE: PRT
<213> ORGANISM: Artificial Sequence
<220> FEATURE:
<223> OTHER INFORMATION: substituted variable light chain framework of
      FW1.4
<220> FEATURE:
<221> NAME/KEY: MISC_FEATURE
<222> LOCATION: (24)..(73)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least three and up to 50 amino acids can be present

<400> SEQUENCE: 91

Glu Ile Val Met Thr Gln Ser Pro Ser Thr Leu Ser Ala Ser Val Gly
 1               5                  10                  15

Asp Arg Val Ile Ile Thr Cys Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Gly Val Pro Ser Arg Phe
    130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Phe Gly Gln Gly
    210                 215                 220

Thr Lys Leu Thr Val Leu Gly
225                 230

<210> SEQ ID NO 92
<211> LENGTH: 483
<212> TYPE: PRT
<213> ORGANISM: Artificial Sequence
<220> FEATURE:
<223> OTHER INFORMATION: rFW1.4
<220> FEATURE:
<221> NAME/KEY: misc_feature
```

```
<222> LOCATION: (24)..(73)
<223> OTHER INFORMATION: Xaa can be any naturally occurring amino acid
<220> FEATURE:
<221> NAME/KEY: misc_feature
<222> LOCATION: (89)..(138)
<223> OTHER INFORMATION: Xaa can be any naturally occurring amino acid
<220> FEATURE:
<221> NAME/KEY: misc_feature
<222> LOCATION: (171)..(220)
<223> OTHER INFORMATION: Xaa can be any naturally occurring amino acid
<220> FEATURE:
<221> NAME/KEY: misc_feature
<222> LOCATION: (277)..(326)
<223> OTHER INFORMATION: Xaa can be any naturally occurring amino acid
<220> FEATURE:
<221> NAME/KEY: misc_feature
<222> LOCATION: (341)..(390)
<223> OTHER INFORMATION: Xaa can be any naturally occurring amino acid
<220> FEATURE:
<221> NAME/KEY: misc_feature
<222> LOCATION: (423)..(472)
<223> OTHER INFORMATION: Xaa can be any naturally occurring amino acid

<400> SEQUENCE: 92

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Gly Val Pro Ser Arg Phe
    130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Phe Gly Gln Gly
    210                 215                 220

Thr Lys Leu Thr Val Leu Gly Gly Gly Gly Ser Gly Gly Gly Gly
225                 230                 235                 240

Ser Gly Gly Gly Gly Ser Gly Gly Gly Ser Glu Val Gln Leu Val
                245                 250                 255

Glu Ser Gly Gly Gly Leu Val Gln Pro Gly Gly Ser Leu Arg Leu Ser
                260                 265                 270

Cys Thr Ala Ser Xaa Xaa Xaa Xaa Xaa Xaa Xaa Xaa Xaa Xaa Xaa
            275                 280                 285
```

Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Trp Val Arg Gln Ala Pro Gly Lys Gly Leu
                325                 330                 335

Glu Trp Val Gly Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
370                 375                 380

Xaa Xaa Xaa Xaa Xaa Xaa Arg Phe Thr Ile Ser Arg Asp Thr Ser Lys
385                 390                 395                 400

Asn Thr Val Tyr Leu Gln Met Asn Ser Leu Arg Ala Glu Asp Thr Ala
                405                 410                 415

Val Tyr Tyr Cys Ala Arg Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
450                 455                 460

Xaa Xaa Xaa Xaa Xaa Xaa Xaa Trp Gly Gln Gly Thr Leu Val Thr
465                 470                 475                 480

Val Ser Ser

<210> SEQ ID NO 93
<211> LENGTH: 483
<212> TYPE: PRT
<213> ORGANISM: Artificial Sequence
<220> FEATURE:
<223> OTHER INFORMATION: framework of rFW1.4(V2)
<220> FEATURE:
<221> NAME/KEY: misc_feature
<222> LOCATION: (24)..(73)
<223> OTHER INFORMATION: Xaa can be any naturally occurring amino acid
<220> FEATURE:
<221> NAME/KEY: misc_feature
<222> LOCATION: (89)..(138)
<223> OTHER INFORMATION: Xaa can be any naturally occurring amino acid
<220> FEATURE:
<221> NAME/KEY: misc_feature
<222> LOCATION: (171)..(220)
<223> OTHER INFORMATION: Xaa can be any naturally occurring amino acid
<220> FEATURE:
<221> NAME/KEY: misc_feature
<222> LOCATION: (277)..(326)
<223> OTHER INFORMATION: Xaa can be any naturally occurring amino acid
<220> FEATURE:
<221> NAME/KEY: misc_feature
<222> LOCATION: (341)..(390)
<223> OTHER INFORMATION: Xaa can be any naturally occurring amino acid
<220> FEATURE:
<221> NAME/KEY: misc_feature
<222> LOCATION: (423)..(472)
<223> OTHER INFORMATION: Xaa can be any naturally occurring amino acid

<400> SEQUENCE: 93

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xa

```
            35                  40                  45
Xaa Xaa Xaa Xaa Xaa Xaa Xaa Xaa Xaa Xaa Xaa Xaa Xaa Xaa
        50                  55                  60
Xaa Xaa Xaa Xaa Xaa Xaa Xaa Xaa Trp Tyr Gln Gln Lys Pro Gly
65                  70                  75                  80
Lys Ala Pro Lys Leu Ile Tyr Xaa Xaa Xaa Xaa Xaa Xaa Xaa
                85                  90                  95
Xaa Xaa Xaa Xaa Xaa Xaa Xaa Xaa Xaa Xaa Xaa Xaa Xaa Xaa
            100                 105                 110
Xaa Xaa Xaa Xaa Xaa Xaa Xaa Xaa Xaa Xaa Xaa Xaa Xaa Xaa
            115                 120                 125
Xaa Xaa Xaa Xaa Xaa Xaa Xaa Xaa Xaa Gly Val Pro Ser Arg Phe
        130                 135                 140
Ser Gly Ser Gly Ser Gly Thr Glu Phe Thr Leu Thr Ile Ser Ser Leu
145                 150                 155                 160
Gln Pro Asp Asp Phe Ala Thr Tyr Tyr Cys Xaa Xaa Xaa Xaa Xaa
                165                 170                 175
Xaa Xaa Xaa Xaa Xaa Xaa Xaa Xaa Xaa Xaa Xaa Xaa Xaa Xaa
            180                 185                 190
Xaa Xaa Xaa Xaa Xaa Xaa Xaa Xaa Xaa Xaa Xaa Xaa Xaa Xaa
            195                 200                 205
Xaa Xaa Xaa Xaa Xaa Xaa Xaa Xaa Xaa Xaa Phe Gly Gln Gly
        210                 215                 220
Thr Lys Leu Thr Val Leu Gly Gly Gly Gly Ser Gly Gly Gly
225                 230                 235                 240
Ser Gly Gly Gly Gly Ser Gly Gly Gly Ser Glu Val Gln Leu Val
                245                 250                 255
Glu Ser Gly Gly Gly Leu Val Gln Pro Gly Gly Ser Leu Arg Leu Ser
                260                 265                 270
Cys Thr Val Ser Xaa Xaa Xaa Xaa Xaa Xaa Xaa Xaa Xaa Xaa
            275                 280                 285
Xaa Xaa Xaa Xaa Xaa Xaa Xaa Xaa Xaa Xaa Xaa Xaa Xaa Xaa
            290                 295                 300
Xaa Xaa Xaa Xaa Xaa Xaa Xaa Xaa Xaa Xaa Xaa Xaa Xaa Xaa
305                 310                 315                 320
Xaa Xaa Xaa Xaa Xaa Xaa Trp Val Arg Gln Ala Pro Gly Lys Gly Leu
                325                 330                 335
Glu Trp Val Gly Xaa Xaa Xaa Xaa Xaa Xaa Xaa Xaa Xaa Xaa
            340                 345                 350
Xaa Xaa Xaa Xaa Xaa Xaa Xaa Xaa Xaa Xaa Xaa Xaa Xaa Xaa
            355                 360                 365
Xaa Xaa Xaa Xaa Xaa Xaa Xaa Xaa Xaa Xaa Xaa Xaa Xaa Xaa
            370                 375                 380
Xaa Xaa Xaa Xaa Xaa Xaa Arg Phe Thr Ile Ser Lys Asp Thr Ser Lys
385                 390                 395                 400
Asn Thr Val Tyr Leu Gln Met Asn Ser Leu Arg Ala Glu Asp Thr Ala
                405                 410                 415
Val Tyr Tyr Cys Ala Arg Xaa Xaa Xaa Xaa Xaa Xaa Xaa Xaa Xaa
                420                 425                 430
Xaa Xaa Xaa Xaa Xaa Xaa Xaa Xaa Xaa Xaa Xaa Xaa Xaa Xaa
            435                 440                 445
Xaa Xaa Xaa Xaa Xaa Xaa Xaa Xaa Xaa Xaa Xaa Xaa Xaa Xaa
            450                 455                 460
```

Xaa Xaa Xaa Xaa Xaa Xaa Xaa Xaa Trp Gly Gln Gly Thr Leu Val Thr
465                 470                 475                 480

Val Ser Ser

<210> SEQ ID NO 94
<211> LENGTH: 253
<212> TYPE: PRT
<213> ORGANISM: Artificial Sequence
<220> FEATURE:
<223> OTHER INFORMATION: EP43min scFv

<400> SEQUENCE: 94

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Gly Ala Ser Arg Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly Gly
            100                 105                 110

Gly Gly Gly Ser Gly Gly Gly Ser Gly Gly Gly Ser Gly Gly
            115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Phe Ser Leu
145                 150                 155                 160

Ser Ser Gly Ala Met Ser Trp Val Arg Gln Ala Pro Gly Lys Gly Leu
                165                 170                 175

Glu Trp Val Ser Val Ile Ile Ser Ser Gly Ala Thr Tyr Tyr Ala Ser
            180                 185                 190

Trp Ala Lys Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
210                 215                 220

Tyr Cys Ala Lys Gly Gly Pro Asp Asp Ser Asn Ser Met Gly Thr Phe
225                 230                 235                 240

Asp Pro Trp Gly Gln Gly Thr Leu Val Thr Val Ser Ser
            245                 250

<210> SEQ ID NO 95
<211> LENGTH: 253
<212> TYPE: PRT
<213> ORGANISM: Artificial Sequence
<220> FEATURE:
<223> OTHER INFORMATION: EP43max scFv

<400> SEQUENCE: 95

Glu Ile Val Met Thr Gln Ser Pro Ser Thr Leu Ser Ala Ser Val Gly
1               5                   10                  15

Asp Arg Val Ile Ile Lys Cys Gln Ala Ser Gln Ser Ile Ser Asp Trp
            20                  25                  30

-continued

Leu Ala Trp Tyr Gln Gln Lys Pro Gly Lys Ala Pro Lys Leu Leu Ile
              35                  40                  45

Tyr Gly Ala Ser Arg Leu Ala Ser Gly Phe Pro Ser Arg Phe Ser Gly
         50                  55                  60

Ser Gly Ser Gly Ala Glu Phe Thr Leu Thr Ile Ser Gly Leu Glu Pro
 65                  70                  75                  80

Ala Asp Phe Ala Thr Tyr Tyr Cys Gln Gln Gly Trp Ser Asp Ser Tyr
                 85                  90                  95

Val Asp Asn Leu Phe Gly Gln Gly Thr Lys Leu Thr Val Leu Gly Gly
                100                 105                 110

Gly Gly Gly Ser Gly Gly Gly Gly Ser Gly Gly Gly Ser Gly Gly
                115                 120                 125

Gly Gly Ser Glu Val Gln Leu Val Glu Ser Gly Gly Gly Leu Val Gln
            130                 135                 140

Pro Gly Gly Ser Leu Arg Leu Ser Cys Thr Val Ser Gly Phe Ser Leu
145                 150                 155                 160

Ser Ser Gly Ala Met Ser Trp Val Arg Gln Ala Pro Gly Lys Gly Leu
                165                 170                 175

Glu Trp Val Gly Val Ile Ile Ser Ser Gly Ala Thr Tyr Tyr Ala Ser
            180                 185                 190

Trp Ala Lys Gly Arg Phe Thr Ile Ser Lys Asp Thr Ser Lys Asn Thr
            195                 200                 205

Val Tyr Leu Gln Met Asn Ser Leu Arg Ala Glu Asp Thr Ala Val Tyr
        210                 215                 220

Tyr Cys Ala Arg Gly Gly Pro Asp Asp Ser Asn Ser Met Gly Thr Phe
225                 230                 235                 240

Asp Pro Trp Gly Gln Gly Thr Leu Val Thr Val Ser Ser
                245                 250

<210> SEQ ID NO 96
<211> LENGTH: 253
<212> TYPE: PRT
<213> ORGANISM: Artificial Sequence
<220> FEATURE:
<223> OTHER INFORMATION: EP43minmax scFv

<400> SEQUENCE: 96

Glu Ile Val Met Thr Gln Ser Pro Ser Thr Leu Ser Ala Ser Val Gly
 1               5                  10                  15

Asp Arg Val Ile Ile Thr Cys Gln Ala Ser Gln Ser Ile Ser Asp Trp
             20                  25                  30

Leu Ala Trp Tyr Gln Gln Lys Pro Gly Lys Ala Pro Lys Leu Leu Ile
              35                  40                  45

Tyr Gly Ala Ser Arg Leu Ala Ser Gly Val Pro Ser Arg Phe Ser Gly
         50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Gln Gly Trp Ser Asp Ser Tyr
                 85                  90                  95

Val Asp Asn Leu Phe Gly Gln Gly Thr Lys Leu Thr Val Leu Gly Gly
                100                 105                 110

Gly Gly Gly Ser Gly Gly Gly Gly Ser Gly Gly Gly Ser Gly Gly
                115                 120                 125

Gly Gly Ser Glu Val Gln Leu Val Glu Ser Gly Gly Gly Leu Val Gln
            130                 135                 140

```
Pro Gly Gly Ser Leu Arg Leu Ser Cys Thr Val Ser Gly Phe Ser Leu
145                 150                 155                 160

Ser Ser Gly Ala Met Ser Trp Val Arg Gln Ala Pro Gly Lys Gly Leu
                165                 170                 175

Glu Trp Val Gly Val Ile Ile Ser Ser Gly Ala Thr Tyr Tyr Ala Ser
            180                 185                 190

Trp Ala Lys Gly Arg Phe Thr Ile Ser Lys Asp Thr Ser Lys Asn Thr
        195                 200                 205

Val Tyr Leu Gln Met Asn Ser Leu Arg Ala Glu Asp Thr Ala Val Tyr
    210                 215                 220

Tyr Cys Ala Arg Gly Gly Pro Asp Asp Ser Asn Ser Met Gly Thr Phe
225                 230                 235                 240

Asp Pro Trp Gly Gln Gly Thr Leu Val Thr Val Ser Ser
                245                 250
```

<210> SEQ ID NO 97
<211> LENGTH: 253
<212> TYPE: PRT
<213> ORGANISM: Artificial Sequence
<220> FEATURE:
<223> OTHER INFORMATION: EP43maxDHP scFv

<400> SEQUENCE: 97

```
Glu Ile Val Met Thr Gln Ser Pro Ser Thr Leu Ser Ala Ser Val Gly
1               5                   10                  15

Asp Arg Val Ile Ile Lys Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Gly Ala Ser Arg Leu Ala Ser Gly Phe Pro Ser Arg Phe Ser Gly
    50                  55                  60

Ser Gly Ser Gly Ala Glu Phe Thr Leu Thr Ile Ser Gly Leu Glu Pro
65              70                  75                  80

Ala Asp Phe Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Glu Val Gln Leu Val Glu Ser Gly Gly Gly Ser Val Gln
    130                 135                 140

Pro Gly Gly Ser Leu Arg Leu Ser Cys Thr Val Ser Gly Phe Ser Leu
145                 150                 155                 160

Ser Ser Gly Ala Met Ser Trp Val Arg Gln Ala Pro Gly Lys Gly Leu
                165                 170                 175

Glu Trp Val Gly Val Ile Ile Ser Ser Gly Ala Thr Tyr Tyr Ala Ser
            180                 185                 190

Trp Ala Lys Gly Arg Phe Thr Ile Ser Lys Asp Thr Ser Lys Asn Thr
        195                 200                 205

Val Tyr Leu Gln Met Asn Ser Leu Arg Ala Glu Asp Thr Ala Thr Tyr
    210                 215                 220

Tyr Cys Ala Arg Gly Gly Pro Asp Asp Ser Asn Ser Met Gly Thr Phe
225                 230                 235                 240

Asp Pro Trp Gly Gln Gly Thr Ser Val Thr Val Ser Ser
                245                 250
```

<210> SEQ ID NO 98
<211> LENGTH: 253
<212> TYPE: PRT
<213> ORGANISM: Artificial Sequence
<220> FEATURE:
<223> OTHER INFORMATION: EP43minmaxDHP scFv

<400> SEQUENCE: 98

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Gly Ala Ser Arg Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly Gly
            100                 105                 110

Gly Gly Gly Ser Gly Gly Gly Ser Gly Gly Gly Ser Gly Gly
        115                 120                 125

Gly Gly Ser Glu Val Gln Leu Val Glu Ser Gly Gly Ser Val Gln
130                 135                 140

Pro Gly Gly Ser Leu Arg Leu Ser Cys Thr Val Ser Gly Phe Ser Leu
145                 150                 155                 160

Ser Ser Gly Ala Met Ser Trp Val Arg Gln Ala Pro Lys Gly Leu
                165                 170                 175

Glu Trp Val Gly Val Ile Ile Ser Ser Gly Ala Thr Tyr Tyr Ala Ser
            180                 185                 190

Trp Ala Lys Gly Arg Phe Thr Ile Ser Lys Asp Thr Ser Lys Asn Thr
        195                 200                 205

Val Tyr Leu Gln Met Asn Ser Leu Arg Ala Glu Asp Thr Ala Thr Tyr
    210                 215                 220

Tyr Cys Ala Arg Gly Gly Pro Asp Asp Ser Asn Ser Met Gly Thr Phe
225                 230                 235                 240

Asp Pro Trp Gly Gln Gly Thr Ser Val Thr Val Ser Ser
                245                 250

<210> SEQ ID NO 99
<211> LENGTH: 253
<212> TYPE: PRT
<213> ORGANISM: Artificial Sequence
<220> FEATURE:
<223> OTHER INFORMATION: EP43minmax VL:T22K scFv

<400> SEQUENCE: 99

Glu Ile Val Met Thr Gln Ser Pro Ser Thr Leu Ser Ala Ser Val Gly
1               5                   10                  15

Asp Arg Val Ile Ile Lys Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Gly Ala Ser Arg Leu Ala Ser Gly Val Pro Ser Arg Phe Ser Gly

```
            50                  55                  60
Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Gln Gly Trp Ser Asp Ser Tyr
                     85                  90                  95

Val Asp Asn Leu Phe Gly Gln Gly Thr Lys Leu Thr Val Leu Gly Gly
                100                 105                 110

Gly Gly Gly Ser Gly Gly Gly Ser Gly Gly Gly Ser Gly Gly
            115                 120                 125

Gly Gly Ser Glu Val Gln Leu Val Glu Ser Gly Gly Leu Val Gln
        130                 135                 140

Pro Gly Gly Ser Leu Arg Leu Ser Cys Thr Val Ser Gly Phe Ser Leu
145                 150                 155                 160

Ser Ser Gly Ala Met Ser Trp Val Arg Gln Ala Pro Gly Lys Gly Leu
                165                 170                 175

Glu Trp Val Gly Val Ile Ile Ser Ser Gly Ala Thr Tyr Tyr Ala Ser
                180                 185                 190

Trp Ala Lys Gly Arg Phe Thr Ile Ser Lys Asp Thr Ser Lys Asn Thr
                195                 200                 205

Val Tyr Leu Gln Met Asn Ser Leu Arg Ala Glu Asp Thr Ala Val Tyr
                210                 215                 220

Tyr Cys Ala Arg Gly Gly Pro Asp Asp Ser Asn Ser Met Gly Thr Phe
225                 230                 235                 240

Asp Pro Trp Gly Gln Gly Thr Leu Val Thr Val Ser Ser
                245                 250

<210> SEQ ID NO 100
<211> LENGTH: 253
<212> TYPE: PRT
<213> ORGANISM: Artificial Sequence
<220> FEATURE:
<223> OTHER INFORMATION: EP43minmax: VL:V58F scFv

<400> SEQUENCE: 100

Glu Ile Val Met Thr Gln Ser Pro Ser Thr Leu Ser Ala Ser Val Gly
 1               5                  10                  15

Asp Arg Val Ile Ile Thr Cys Gln Ala Ser Gln Ser Ile Ser Asp Trp
                20                  25                  30

Leu Ala Trp Tyr Gln Gln Lys Pro Gly Lys Ala Pro Lys Leu Leu Ile
                35                  40                  45

Tyr Gly Ala Ser Arg Leu Ala Ser Gly Phe Pro Ser Arg Phe Ser Gly
        50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Gln Gly Trp Ser Asp Ser Tyr
                     85                  90                  95

Val Asp Asn Leu Phe Gly Gln Gly Thr Lys Leu Thr Val Leu Gly Gly
                100                 105                 110

Gly Gly Gly Ser Gly Gly Gly Ser Gly Gly Gly Ser Gly Gly
            115                 120                 125

Gly Gly Ser Glu Val Gln Leu Val Glu Ser Gly Gly Leu Val Gln
        130                 135                 140

Pro Gly Gly Ser Leu Arg Leu Ser Cys Thr Val Ser Gly Phe Ser Leu
145                 150                 155                 160

Ser Ser Gly Ala Met Ser Trp Val Arg Gln Ala Pro Gly Lys Gly Leu
```

165                 170                 175
Glu Trp Val Gly Val Ile Ile Ser Ser Gly Ala Thr Tyr Tyr Ala Ser
            180                 185                 190

Trp Ala Lys Gly Arg Phe Thr Ile Ser Lys Asp Thr Ser Lys Asn Thr
        195                 200                 205

Val Tyr Leu Gln Met Asn Ser Leu Arg Ala Glu Asp Thr Ala Val Tyr
    210                 215                 220

Tyr Cys Ala Arg Gly Gly Pro Asp Asp Ser Asn Ser Met Gly Thr Phe
225                 230                 235                 240

Asp Pro Trp Gly Gln Gly Thr Leu Val Thr Val Ser Ser
                245                 250

<210> SEQ ID NO 101
<211> LENGTH: 253
<212> TYPE: PRT
<213> ORGANISM: Artificial Sequence
<220> FEATURE:
<223> OTHER INFORMATION: EP43minmax VL:D81A scFv

<400> SEQUENCE: 101

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Gly Ala Ser Arg Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Ala Asp Phe Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly Gly
            100                 105                 110

Gly Gly Gly Ser Gly Gly Gly Gly Ser Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Thr Val Ser Gly Phe Ser Leu
145                 150                 155                 160

Ser Ser Gly Ala Met Ser Trp Val Arg Gln Ala Pro Gly Lys Gly Leu
                165                 170                 175

Glu Trp Val Gly Val Ile Ile Ser Ser Gly Ala Thr Tyr Tyr Ala Ser
            180                 185                 190

Trp Ala Lys Gly Arg Phe Thr Ile Ser Lys Asp Thr Ser Lys Asn Thr
        195                 200                 205

Val Tyr Leu Gln Met Asn Ser Leu Arg Ala Glu Asp Thr Ala Val Tyr
    210                 215                 220

Tyr Cys Ala Arg Gly Gly Pro Asp Asp Ser Asn Ser Met Gly Thr Phe
225                 230                 235                 240

Asp Pro Trp Gly Gln Gly Thr Leu Val Thr Val Ser Ser
                245                 250

<210> SEQ ID NO 102
<211> LENGTH: 253
<212> TYPE: PRT

<213> ORGANISM: Artificial Sequence
<220> FEATURE:
<223> OTHER INFORMATION: EP43minmax VL:Q79E scFv

<400> SEQUENCE: 102

| Glu | Ile | Val | Met | Thr | Gln | Ser | Pro | Ser | Thr | Leu | Ser | Ala | Ser | Val | Gly |
|---|---|---|---|---|---|---|---|---|---|---|---|---|---|---|---|
| 1 | | | | 5 | | | | | 10 | | | | | 15 | |

Asp Arg Val Ile Ile Thr Cys Gln Ala Ser Gln Ser Ile Ser Asp Trp
                20                  25                  30

Leu Ala Trp Tyr Gln Gln Lys Pro Gly Lys Ala Pro Lys Leu Leu Ile
            35                  40                  45

Tyr Gly Ala Ser Arg Leu Ala Ser Gly Val Pro Ser Arg Phe Ser Gly
    50                  55                  60

Ser Gly Ser Gly Ala Glu Phe Thr Leu Thr Ile Ser Ser Leu Glu Pro
65                  70                  75                  80

Asp Asp Phe Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly Gly
            100                 105                 110

Gly Gly Gly Ser Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Thr Val Ser Gly Phe Ser Leu
145                 150                 155                 160

Ser Ser Gly Ala Met Ser Trp Val Arg Gln Ala Pro Gly Lys Gly Leu
                165                 170                 175

Glu Trp Val Gly Val Ile Ile Ser Ser Gly Ala Thr Tyr Tyr Ala Ser
            180                 185                 190

Trp Ala Lys Gly Arg Phe Thr Ile Ser Lys Asp Thr Ser Lys Asn Thr
    195                 200                 205

Val Tyr Leu Gln Met Asn Ser Leu Arg Ala Glu Asp Thr Ala Val Tyr
    210                 215                 220

Tyr Cys Ala Arg Gly Gly Pro Asp Asp Ser Asn Ser Met Gly Thr Phe
225                 230                 235                 240

Asp Pro Trp Gly Gln Gly Thr Leu Val Thr Val Ser Ser
                245                 250

<210> SEQ ID NO 103
<211> LENGTH: 253
<212> TYPE: PRT
<213> ORGANISM: Artificial Sequence
<220> FEATURE:
<223> OTHER INFORMATION: EP1min scFv

<400> SEQUENCE: 103

Glu Ile Val Met Thr Gln Ser Pro Ser Thr Leu Ser Ala Ser Val Gly
1               5                   10                  15

Asp Arg Val Ile Ile Thr Cys Gln Ser Thr Glu Ser Val Tyr Lys Asn
                20                  25                  30

Asn Tyr Leu Ala Trp Tyr Gln Gln Lys Pro Gly Lys Ala Pro Lys Leu
            35                  40                  45

Leu Ile Tyr Asp Ala Ser Thr Leu Ala Ser Gly Val Pro Ser Arg Phe
    50                  55                  60

Ser Gly Ser Gly Ser Gly Ala Glu Phe Thr Leu Thr Ile Ser Ser Leu
65                  70                  75                  80

```
Gln Pro Asp Asp Phe Ala Thr Tyr Tyr Cys Ala Gly Tyr Tyr Arg Ser
                85                  90                  95

Gly Ser Gly Thr Ala Asn Gly Ser Phe Gly Gln Gly Thr Lys Leu Thr
            100                 105                 110

Val Leu Gly Gly Gly Gly Ser Gly Gly Gly Gly Ser Gly Gly Gly
            115                 120                 125

Gly Ser Gly Gly Gly Gly Ser Glu Val Gln Leu Val Glu Ser Gly Gly
            130                 135                 140

Gly Leu Val Gln Pro Gly Gly Ser Leu Arg Leu Ser Cys Ala Ala Ser
145                 150                 155                 160

Gly Phe Thr Phe Ser Asn Asp Ala Ile Ser Trp Val Arg Gln Ala Pro
                165                 170                 175

Gly Lys Gly Leu Glu Trp Val Ser Tyr Ile Ser Asp Trp Ser Ile Arg
            180                 185                 190

Tyr Tyr Ala Asn Trp Ala Gln Gly Arg Phe Thr Ile Ser Arg Asp Asn
            195                 200                 205

Ser Lys Asn Thr Leu Tyr Leu Gln Met Asn Ser Leu Arg Ala Glu Asp
            210                 215                 220

Thr Ala Val Tyr Tyr Cys Ala Lys Gly Ala Pro Gly Ala Gly Asp Asn
225                 230                 235                 240

Gly Ile Trp Gly Gln Gly Thr Leu Val Thr Val Ser Ser
                245                 250

<210> SEQ ID NO 104
<211> LENGTH: 253
<212> TYPE: PRT
<213> ORGANISM: Artificial Sequence
<220> FEATURE:
<223> OTHER INFORMATION: EP1max scFv

<400> SEQUENCE: 104

Glu Ile Val Met Thr Gln Ser Pro Ser Thr Leu Ser Ala Ser Val Gly
1               5                   10                  15

Asp Arg Val Ile Ile Thr Cys Gln Ser Thr Glu Ser Val Tyr Lys Asn
            20                  25                  30

Asn Tyr Leu Ala Trp Tyr Gln Gln Lys Pro Gly Lys Ala Pro Lys Leu
            35                  40                  45

Leu Ile Tyr Asp Ala Ser Thr Leu Ala Ser Gly Val Pro Ser Arg Phe
50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Ala Gly Tyr Tyr Arg Ser
                85                  90                  95

Gly Ser Gly Thr Ala Asn Gly Ser Phe Gly Gln Gly Thr Lys Leu Thr
            100                 105                 110

Val Leu Gly Gly Gly Gly Ser Gly Gly Gly Gly Ser Gly Gly Gly
            115                 120                 125

Gly Ser Gly Gly Gly Gly Ser Glu Val Gln Leu Val Glu Ser Gly Gly
            130                 135                 140

Gly Ser Val Gln Pro Gly Gly Ser Leu Arg Leu Ser Cys Thr Val Ser
145                 150                 155                 160

Gly Ile Asp Leu Ser Asn Asp Ala Ile Ser Trp Val Arg Gln Ala Pro
                165                 170                 175

Gly Lys Gly Leu Glu Trp Val Ala Tyr Ile Ser Asp Trp Ser Ile Arg
            180                 185                 190
```

```
Tyr Tyr Ala Asn Trp Ala Gln Gly Arg Phe Thr Ile Ser Lys Asp Thr
            195                 200                 205

Ser Lys Asn Thr Val Tyr Leu Gln Met Asn Ser Leu Arg Ala Glu Asp
    210                 215                 220

Thr Ala Thr Tyr Tyr Cys Ala Arg Gly Ala Pro Gly Ala Gly Asp Asn
225                 230                 235                 240

Gly Ile Trp Gly Gln Gly Thr Val Thr Val Ser Ser
                245                 250

<210> SEQ ID NO 105
<211> LENGTH: 253
<212> TYPE: PRT
<213> ORGANISM: Artificial Sequence
<220> FEATURE:
<223> OTHER INFORMATION: EP1minmax scFv

<400> SEQUENCE: 105

Glu Ile Val Met Thr Gln Ser Pro Ser Thr Leu Ser Ala Ser Val Gly
1               5                   10                  15

Asp Arg Val Ile Ile Thr Cys Gln Ser Thr Glu Ser Val Tyr Lys Asn
            20                  25                  30

Asn Tyr Leu Ala Trp Tyr Gln Gln Lys Pro Gly Lys Ala Pro Lys Leu
        35                  40                  45

Leu Ile Tyr Asp Ala Ser Thr Leu Ala Ser Gly Val Pro Ser Arg Phe
    50                  55                  60

Ser Gly Ser Gly Ser Gly Ala Glu Phe Thr Leu Thr Ile Ser Ser Leu
65                  70                  75                  80

Gln Pro Asp Asp Phe Ala Thr Tyr Tyr Cys Ala Gly Tyr Tyr Arg Ser
                85                  90                  95

Gly Ser Gly Thr Ala Asn Gly Ser Phe Gly Gln Gly Thr Lys Leu Thr
            100                 105                 110

Val Leu Gly Gly Gly Gly Ser Gly Gly Gly Ser Gly Gly Gly
            115                 120                 125

Gly Ser Gly Gly Gly Ser Glu Val Gln Leu Val Glu Ser Gly Gly
    130                 135                 140

Gly Ser Val Gln Pro Gly Gly Ser Leu Arg Leu Ser Cys Thr Val Ser
145                 150                 155                 160

Gly Ile Asp Leu Ser Asn Asp Ala Ile Ser Trp Val Arg Gln Ala Pro
                165                 170                 175

Gly Lys Gly Leu Glu Trp Val Ala Tyr Ile Ser Asp Trp Ser Ile Arg
            180                 185                 190

Tyr Tyr Ala Asn Trp Ala Gln Gly Arg Phe Thr Ile Ser Lys Asp Thr
        195                 200                 205

Ser Lys Asn Thr Val Tyr Leu Gln Met Asn Ser Leu Arg Ala Glu Asp
    210                 215                 220

Thr Ala Thr Tyr Tyr Cys Ala Arg Gly Ala Pro Gly Ala Gly Asp Asn
225                 230                 235                 240

Gly Ile Trp Gly Gln Gly Thr Val Thr Val Ser Ser
                245                 250

<210> SEQ ID NO 106
<211> LENGTH: 252
<212> TYPE: PRT
<213> ORGANISM: Artificial Sequence
<220> FEATURE:
<223> OTHER INFORMATION: EP6min scFv

<400> SEQUENCE: 106
```

```
Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ser Ile Tyr Ser Gly
            20                  25                  30

Leu Ala Trp Tyr Gln Gln Lys Pro Gly Lys Ala Pro Lys Leu Leu Ile
        35                  40                  45

Tyr Gln Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65              70                  75                  80

Asp Asp Phe Ala Thr Tyr Tyr Cys Gln Gln Gly Phe Gly Thr Ser Asn
                85                  90                  95

Val Glu Asn Pro Phe Gly Gln Gly Thr Lys Leu Thr Val Leu Gly Gly
            100                 105                 110

Gly Gly Gly Ser Gly Gly Gly Ser Gly Gly Gly Ser Gly Gly
            115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Phe Ser Leu
145             150                 155                 160

Ser Arg Tyr Gly Val Ser Trp Val Arg Gln Ala Pro Gly Lys Gly Leu
                165                 170                 175

Glu Trp Val Ser Thr Ile Gly Glu Ala Gly Arg Ala Tyr Tyr Ala Asn
            180                 185                 190

Trp Ala Arg Ser Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Lys Gly Glu Val Phe Asn Asn Gly Trp Gly Ala Phe Asn
225             230                 235                 240

Ile Trp Gly Gln Gly Thr Leu Val Thr Val Ser Ser
            245                 250

<210> SEQ ID NO 107
<211> LENGTH: 252
<212> TYPE: PRT
<213> ORGANISM: Artificial Sequence
<220> FEATURE:
<223> OTHER INFORMATION: EP6max scFv

<400> SEQUENCE: 107

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ser Ile Tyr Ser Gly
            20                  25                  30

Leu Ala Trp Tyr Gln Gln Lys Pro Gly Lys Ala Pro Lys Leu Leu Ile
        35                  40                  45

Tyr Gln Ala Ser Thr Leu Ala Ser Gly Val Pro Ser Arg Phe Ser Gly
    50                  55                  60

Ser Gly Ser Gly Thr Asp Phe Thr Leu Ala Ile Ser Ser Leu Gln Pro
65              70                  75                  80

Asp Asp Phe Ala Thr Tyr Tyr Cys Gln Gln Gly Phe Gly Thr Ser Asn
                85                  90                  95

Val Glu Asn Pro Phe Gly Gln Gly Thr Lys Leu Thr Val Leu Gly Gly
            100                 105                 110
```

```
Gly Gly Gly Ser Gly Gly Gly Ser Gly Gly Gly Ser Gly Gly
        115                 120                 125

Gly Gly Ser Glu Val Gln Leu Val Glu Ser Gly Gly Leu Val Gln
130                 135                 140

Pro Gly Ser Leu Arg Leu Ser Cys Thr Val Ser Gly Phe Ser Leu
145                 150                 155                 160

Ser Arg Tyr Gly Val Ser Trp Val Arg Gln Ala Pro Gly Lys Gly Leu
            165                 170                 175

Glu Trp Val Gly Thr Ile Gly Glu Ala Gly Arg Ala Tyr Tyr Ala Asn
            180                 185                 190

Trp Ala Arg Ser Arg Ser Thr Ile Ser Arg Asp Thr Ser Lys Asn Thr
            195                 200                 205

Val Tyr Leu Gln Met Asn Ser Leu Arg Ala Glu Asp Thr Ala Val Tyr
            210                 215                 220

Tyr Cys Ala Arg Gly Glu Val Phe Asn Asn Gly Trp Gly Ala Phe Asn
225                 230                 235                 240

Ile Trp Gly Gln Gly Thr Leu Val Thr Val Ser Ser
            245                 250

<210> SEQ ID NO 108
<211> LENGTH: 252
<212> TYPE: PRT
<213> ORGANISM: Artificial Sequence
<220> FEATURE:
<223> OTHER INFORMATION: EP6minmax scFv

<400> SEQUENCE: 108

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ser Ile Tyr Ser Gly
            20                  25                  30

Leu Ala Trp Tyr Gln Gln Lys Pro Gly Lys Ala Pro Lys Leu Leu Ile
            35                  40                  45

Tyr Gln Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Gly Phe Gly Thr Ser Asn
                85                  90                  95

Val Glu Asn Pro Phe Gly Gln Gly Thr Lys Leu Thr Val Leu Gly Gly
            100                 105                 110

Gly Gly Gly Ser Gly Gly Gly Gly Ser Gly Gly Gly Ser Gly Gly
        115                 120                 125

Gly Gly Ser Glu Val Gln Leu Val Glu Ser Gly Gly Leu Val Gln
130                 135                 140

Pro Gly Ser Leu Arg Leu Ser Cys Thr Val Ser Gly Phe Ser Leu
145                 150                 155                 160

Ser Arg Tyr Gly Val Ser Trp Val Arg Gln Ala Pro Gly Lys Gly Leu
            165                 170                 175

Glu Trp Val Gly Thr Ile Gly Glu Ala Gly Arg Ala Tyr Tyr Ala Asn
            180                 185                 190

Trp Ala Arg Ser Arg Ser Thr Ile Ser Arg Asp Thr Ser Lys Asn Thr
            195                 200                 205

Val Tyr Leu Gln Met Asn Ser Leu Arg Ala Glu Asp Thr Ala Val Tyr
            210                 215                 220
```

Tyr Cys Ala Arg Gly Glu Val Phe Asn Asn Gly Trp Gly Ala Phe Asn
225                 230                 235                 240

Ile Trp Gly Gln Gly Thr Leu Val Thr Val Ser Ser
                245                 250

<210> SEQ ID NO 109
<211> LENGTH: 252
<212> TYPE: PRT
<213> ORGANISM: Artificial Sequence
<220> FEATURE:
<223> OTHER INFORMATION: EP15min scFv

<400> SEQUENCE: 109

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Asn Ile Tyr Thr Ser
            20                  25                  30

Leu Ala Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Gly Phe Ala Thr Ser Asn
                85                  90                  95

Val Glu Asn Pro Phe Gly Gln Gly Thr Lys Leu Thr Val Leu Gly Gly
            100                 105                 110

Gly Gly Ser Gly Gly Gly Gly Ser Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Phe Thr Phe
145                 150                 155                 160

Ser Arg Tyr Gly Val Ser Trp Val Arg Gln Ala Pro Gly Lys Gly Leu
                165                 170                 175

Glu Trp Val Ser Ala Ile Gly Glu Thr Gly Arg Ala Tyr Tyr Ala Asn
            180                 185                 190

Trp Ala Lys Ser Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Lys Gly Glu Glu Phe Asn Asn Gly Trp Gly Ala Phe Asn
225                 230                 235                 240

Ile Trp Gly Gln Gly Thr Leu Val Thr Val Ser Ser
                245                 250

<210> SEQ ID NO 110
<211> LENGTH: 252
<212> TYPE: PRT
<213> ORGANISM: Artificial Sequence
<220> FEATURE:
<223> OTHER INFORMATION: EP15max scFv

<400> SEQUENCE: 110

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Asn Ile Tyr Thr Ser

```
            20                  25                  30
Leu Ala Trp Tyr Gln Gln Lys Pro Gly Lys Ala Pro Lys Leu Leu Ile
            35                  40                  45

Tyr Ser Ala Ser Thr Leu Ala Ser Gly Val Pro Ser Arg Phe Ser Gly
            50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Phe Ala Thr Ser Asn
                    85                  90                  95

Val Glu Asn Pro Phe Gly Gln Gly Thr Lys Leu Thr Val Leu Gly Gly
                100                 105                 110

Gly Gly Gly Ser Gly Gly Gly Ser Gly Gly Gly Ser Gly Gly
                115                 120                 125

Gly Gly Ser Glu Val Gln Leu Val Glu Ser Gly Gly Gly Ser Val Gln
                130                 135                 140

Pro Gly Gly Ser Leu Arg Leu Ser Cys Thr Val Ser Gly Phe Ser Leu
145                 150                 155                 160

Ser Arg Tyr Gly Val Ser Trp Val Arg Gln Ala Pro Gly Lys Gly Leu
                165                 170                 175

Glu Trp Val Gly Ala Ile Gly Glu Thr Gly Arg Ala Tyr Tyr Ala Asn
                180                 185                 190

Trp Ala Lys Ser Arg Ser Thr Ile Ser Arg Asp Thr Ser Lys Asn Thr
                195                 200                 205

Val Tyr Leu Gln Met Asn Ser Leu Arg Ala Glu Asp Thr Ala Thr Tyr
                210                 215                 220

Tyr Cys Ala Arg Gly Glu Glu Phe Asn Asn Gly Trp Gly Ala Phe Asn
225                 230                 235                 240

Ile Trp Gly Gln Gly Thr Thr Val Thr Val Ser Ser
                245                 250

<210> SEQ ID NO 111
<211> LENGTH: 252
<212> TYPE: PRT
<213> ORGANISM: Artificial Sequence
<220> FEATURE:
<223> OTHER INFORMATION: EP15max scFv

<400> SEQUENCE: 111

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Asn Ile Tyr Thr Ser
                20                  25                  30

Leu Ala Trp Tyr Gln Gln Lys Pro Gly Lys Ala Pro Lys Leu Leu Ile
            35                  40                  45

Tyr Ser Ala Ser Thr Leu Ala Ser Gly Val Pro Ser Arg Phe Ser Gly
            50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Gly Phe Ala Thr Ser Asn
                    85                  90                  95

Val Glu Asn Pro Phe Gly Gly Gly Thr Lys Leu Thr Val Leu Gly Gly
                100                 105                 110

Gly Gly Gly Ser Gly Gly Gly Ser Gly Gly Gly Ser Gly Gly
                115                 120                 125

Gly Gly Ser Glu Val Gln Leu Val Glu Ser Gly Gly Gly Ser Val Gln
```

```
            130                 135                 140
Pro Gly Gly Ser Leu Arg Leu Ser Cys Thr Val Ser Gly Phe Ser Leu
145                 150                 155                 160

Ser Arg Tyr Gly Val Ser Trp Val Arg Gln Ala Pro Gly Lys Gly Leu
                165                 170                 175

Glu Trp Val Gly Ala Ile Gly Glu Thr Gly Arg Ala Tyr Tyr Ala Asn
                180                 185                 190

Trp Ala Lys Ser Arg Ser Thr Ile Ser Arg Asp Thr Ser Lys Asn Thr
                195                 200                 205

Val Tyr Leu Gln Met Asn Ser Leu Arg Ala Glu Asp Thr Ala Thr Tyr
                210                 215                 220

Tyr Cys Ala Arg Gly Glu Glu Phe Asn Asn Gly Trp Gly Ala Phe Asn
225                 230                 235                 240

Ile Trp Gly Gln Gly Thr Thr Val Thr Val Ser Ser
                245                 250

<210> SEQ ID NO 112
<211> LENGTH: 252
<212> TYPE: PRT
<213> ORGANISM: Artificial Sequence
<220> FEATURE:
<223> OTHER INFORMATION: EP19minmod scFv

<400> SEQUENCE: 112

Glu Ile Val Met Thr Gln Ser Pro Ser Thr Leu Ser Ala Ser Val Gly
1               5                   10                  15

Asp Arg Val Ile Ile Thr Cys Gln Ala Ser Asp Asn Ile Tyr Arg Gly
                20                  25                  30

Leu Ala Trp Tyr Gln Gln Lys Pro Gly Lys Ala Pro Lys Leu Leu Ile
                35                  40                  45

Tyr Asp Ala Ser Thr Leu Gln Ser Gly Val Pro Ser Arg Phe Ser Gly
            50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Leu Gly Val Tyr Gly Tyr Ser Ser
                85                  90                  95

Asp Asp Gly Ala Ala Phe Gly Gln Gly Thr Lys Leu Thr Val Leu Gly
                100                 105                 110

Gly Gly Gly Gly Ser Gly Gly Gly Gly Ser Gly Gly Gly Gly Ser Gly
                115                 120                 125

Gly Gly Gly Ser Glu Val Gln Leu Val Glu Ser Gly Gly Gly Leu Val
            130                 135                 140

Gln Pro Gly Gly Ser Leu Arg Leu Ser Cys Ala Ala Ser Gly Phe Ser
145                 150                 155                 160

Leu Asn Ser Asn Glu Ile Ser Trp Val Arg Gln Ala Pro Gly Lys Gly
                165                 170                 175

Leu Glu Trp Val Ser Tyr Ile Gly Asn Gly Gly Met Thr His Tyr Ala
                180                 185                 190

Ser Trp Ala Lys Gly Arg Phe Thr Ile Ser Arg Asp Asn Ser Lys Asn
                195                 200                 205

Thr Leu Tyr Leu Gln Met Asn Ser Leu Arg Ala Glu Asp Thr Ala Val
                210                 215                 220

Tyr Tyr Cys Ala Lys Ser Val Glu Tyr Thr Asp Leu Tyr Tyr Leu Asn
225                 230                 235                 240

Ile Trp Gly Gln Gly Thr Leu Val Thr Val Ser Ser
```

<210> SEQ ID NO 113
<211> LENGTH: 252
<212> TYPE: PRT
<213> ORGANISM: Artificial Sequence
<220> FEATURE:
<223> OTHER INFORMATION: EP19maxmod scFv

<400> SEQUENCE: 113

Glu Ile Val Met Thr Gln Ser Pro Ser Thr Leu Ser Ala Ser Val Gly
1               5                   10                  15

Asp Arg Val Ile Ile Thr Cys Gln Ala Ser Asp Asn Ile Tyr Arg Gly
            20                  25                  30

Leu Ala Trp Tyr Gln Gln Lys Pro Gly Lys Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Gln Phe Thr Leu Thr Ile Ser Ser Leu Gln Pro
65                  70                  75                  80

Asp Asp Phe Ala Thr Tyr Tyr Cys Leu Gly Val Tyr Gly Tyr Ser Ser
                85                  90                  95

Asp Asp Gly Ala Ala Phe Gly Gln Gly Thr Lys Leu Thr Val Leu Gly
            100                 105                 110

Gly Gly Gly Gly Ser Gly Gly Gly Ser Gly Gly Gly Gly Ser Gly
        115                 120                 125

Gly Gly Gly Ser Glu Val Gln Leu Val Glu Ser Gly Gly Gly Leu Val
130                 135                 140

Gln Pro Gly Gly Ser Leu Arg Leu Ser Cys Thr Val Ser Gly Phe Ser
145                 150                 155                 160

Leu Asn Ser Asn Glu Ile Ser Trp Val Arg Gln Ala Pro Gly Lys Gly
                165                 170                 175

Leu Glu Trp Val Gly Tyr Ile Gly Asn Gly Gly Met Thr His Tyr Ala
            180                 185                 190

Ser Trp Ala Lys Gly Arg Phe Thr Ile Ser Arg Asp Thr Ser Lys Asn
        195                 200                 205

Thr Val Tyr Leu Gln Met Asn Ser Leu Arg Ala Glu Asp Thr Ala Val
    210                 215                 220

Tyr Tyr Cys Ala Ser Ser Val Glu Tyr Thr Asp Leu Tyr Tyr Leu Asn
225                 230                 235                 240

Ile Trp Gly Gln Gly Thr Leu Val Thr Val Ser Ser
                245                 250

<210> SEQ ID NO 114
<211> LENGTH: 253
<212> TYPE: PRT
<213> ORGANISM: Artificial Sequence
<220> FEATURE:
<223> OTHER INFORMATION: EP43min scFv

<400> SEQUENCE: 114

Glu Ile Val Met Thr Gln Ser Pro Ser Thr Leu Ser Ala Ser Val Gly
1               5                   10                  15

Asp Arg Val Ile Ile Thr Cys Gln Ser Ser Gln Ser Val Tyr Gly Asn
            20                  25                  30

Ile Trp Met Ala Trp Tyr Gln Gln Lys Pro Gly Lys Ala Pro Lys Leu
        35                  40                  45

```
Leu Ile Tyr Gln Ala Ser Lys Leu Ala Ser Gly Val Pro Ser Arg Phe
 50                  55                  60

Ser Gly Ser Gly Ser Gly Ala Glu Phe Thr Leu Thr Ile Ser Ser Leu
 65                  70                  75                  80

Gln Pro Asp Asp Phe Ala Thr Tyr Tyr Cys Gln Gly Asn Phe Asn Thr
                 85                  90                  95

Gly Asp Arg Tyr Ala Phe Gly Gln Gly Thr Lys Leu Thr Val Leu Gly
                100                 105                 110

Gly Gly Gly Gly Ser Gly Gly Gly Ser Gly Gly Gly Ser Gly
            115                 120                 125

Gly Gly Gly Ser Glu Val Gln Leu Val Glu Ser Gly Gly Gly Leu Val
            130                 135                 140

Gln Pro Gly Gly Ser Leu Arg Leu Ser Cys Ala Ala Ser Gly Phe Thr
145                 150                 155                 160

Ile Ser Arg Ser Tyr Trp Ile Cys Trp Val Arg Gln Ala Pro Gly Lys
                165                 170                 175

Gly Leu Glu Trp Val Ser Cys Ile Tyr Gly Asp Asn Asp Ile Thr Pro
                180                 185                 190

Leu Tyr Ala Asn Trp Ala Lys Gly Arg Phe Thr Ile Ser Arg Asp Asn
                195                 200                 205

Ser Lys Asn Thr Leu Tyr Leu Gln Met Asn Ser Leu Arg Ala Glu Asp
210                 215                 220

Thr Ala Val Tyr Tyr Cys Ala Lys Leu Gly Tyr Ala Asp Tyr Ala Tyr
225                 230                 235                 240

Asp Leu Trp Gly Gln Gly Thr Leu Val Thr Val Ser Ser
                245                 250
```

<210> SEQ ID NO 115
<211> LENGTH: 253
<212> TYPE: PRT
<213> ORGANISM: Artificial Sequence
<220> FEATURE:
<223> OTHER INFORMATION: EP34max scFv

<400> SEQUENCE: 115

```
Glu Ile Val Met Thr Gln Ser Pro Ser Thr Leu Ser Ala Ser Leu Gly
 1               5                  10                  15

Asp Arg Val Ile Ile Thr Cys Gln Ser Ser Gln Ser Val Tyr Gly Asn
                 20                  25                  30

Ile Trp Met Ala Trp Tyr Gln Gln Lys Ser Gly Lys Ala Pro Lys Leu
             35                  40                  45

Leu Ile Tyr Gln Ala Ser Lys Leu Ala Ser Gly Val Pro Ser Arg Phe
 50                  55                  60

Ser Gly Ser Gly Ser Gly Ala Glu Phe Thr Leu Thr Ile Ser Ser Leu
 65                  70                  75                  80

Gln Pro Asp Asp Phe Ala Thr Tyr Tyr Cys Gln Gly Asn Phe Asn Thr
                 85                  90                  95

Gly Asp Arg Tyr Ala Phe Gly Gln Gly Thr Lys Leu Thr Val Leu Gly
                100                 105                 110

Gly Gly Gly Gly Ser Gly Gly Gly Ser Gly Gly Gly Ser Gly
            115                 120                 125

Gly Gly Gly Ser Glu Val Gln Leu Val Glu Ser Gly Gly Gly Leu Val
            130                 135                 140

Gln Pro Gly Gly Ser Leu Arg Leu Ser Cys Thr Ala Ser Gly Phe Thr
145                 150                 155                 160
```

```
Ile Ser Arg Ser Tyr Trp Ile Cys Trp Val Arg Gln Ala Pro Gly Lys
            165                 170                 175

Gly Leu Glu Trp Val Ala Cys Ile Tyr Gly Asp Asn Asp Ile Thr Pro
            180                 185                 190

Leu Tyr Ala Asn Trp Ala Lys Gly Arg Phe Pro Val Ser Thr Asp Thr
            195                 200                 205

Ser Lys Asn Thr Val Tyr Leu Gln Met Asn Ser Leu Arg Ala Glu Asp
            210                 215                 220

Thr Ala Val Tyr Tyr Cys Ala Arg Leu Gly Tyr Ala Asp Tyr Ala Tyr
225                 230                 235                 240

Asp Leu Trp Gly Gln Gly Thr Leu Val Thr Val Ser Ser
            245                 250

<210> SEQ ID NO 116
<211> LENGTH: 253
<212> TYPE: PRT
<213> ORGANISM: Artificial Sequence
<220> FEATURE:
<223> OTHER INFORMATION: EP35min scFv

<400> SEQUENCE: 116

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Asn Leu
            20                  25                  30

Leu Ala Trp Tyr Gln Gln Lys Pro Gly Lys Ala Pro Lys Leu Leu Ile
            35                  40                  45

Tyr Ala Ala Ser Lys Leu Ala Ser Gly Val Pro Ser Arg Phe Ser Gly
        50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Gly Trp Ser His Thr Asn
            85                  90                  95

Val Asp Asn Thr Phe Gly Gln Gly Thr Lys Leu Thr Val Leu Gly Gly
            100                 105                 110

Gly Gly Gly Ser Gly Gly Gly Ser Gly Gly Gly Ser Gly Gly
            115                 120                 125

Gly Gly Ser Glu Val Gln Leu Val Glu Ser Gly Gly Gly Leu Val Gln
            130                 135                 140

Pro Gly Gly Ser Leu Arg Leu Ser Cys Ala Ala Ser Gly Phe Thr Phe
145                 150                 155                 160

Ser Val Gly Tyr Trp Ile Cys Trp Val Arg Gln Ala Pro Gly Lys Gly
            165                 170                 175

Leu Glu Trp Val Ser Cys Ile Asp Ala Gly Thr Ser Gly Gly Thr Tyr
            180                 185                 190

Tyr Ala Thr Trp Ala Lys Gly Arg Phe Thr Ile Ser Arg Asp Asn Ser
            195                 200                 205

Lys Asn Thr Leu Tyr Leu Gln Met Asn Ser Leu Arg Ala Glu Asp Thr
            210                 215                 220

Ala Val Tyr Tyr Cys Ala Lys Gly Val Ser Ser Asn Gly Tyr Tyr Phe
225                 230                 235                 240

Lys Leu Trp Gly Gln Gly Thr Leu Val Thr Val Ser Ser
            245                 250

<210> SEQ ID NO 117
<211> LENGTH: 253
```

<212> TYPE: PRT
<213> ORGANISM: Artificial Sequence
<220> FEATURE:
<223> OTHER INFORMATION: EP35max scFv

<400> SEQUENCE: 117

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Asn Leu
            20                  25                  30

Leu Ala Trp Tyr Gln Gln Lys Pro Gly Lys Ala Pro Lys Leu Leu Ile
        35                  40                  45

Val Ala Ala Ser Lys Leu Ala Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Trp Ser His Thr Asn
                85                  90                  95

Val Asp Asn Thr Phe Gly Gln Gly Thr Lys Leu Thr Val Leu Gly Gly
            100                 105                 110

Gly Gly Gly Ser Gly Gly Gly Ser Gly Gly Gly Ser Gly Gly
        115                 120                 125

Gly Gly Ser Glu Val Gln Leu Val Glu Ser Gly Gly Ser Val Gln
130                 135                 140

Pro Gly Gly Ser Leu Arg Leu Ser Cys Thr Ala Ser Gly Phe Ser Phe
145                 150                 155                 160

Ser Val Gly Tyr Trp Ile Cys Trp Val Arg Gln Ala Pro Gly Lys Gly
                165                 170                 175

Leu Glu Trp Val Ala Cys Ile Asp Ala Gly Thr Ser Gly Gly Thr Tyr
            180                 185                 190

Tyr Ala Thr Trp Ala Lys Gly Arg Phe Thr Ile Ser Lys Asp Thr Ser
        195                 200                 205

Lys Asn Thr Val Tyr Leu Gln Met Asn Ser Leu Arg Ala Glu Asp Thr
210                 215                 220

Ala Thr Tyr Tyr Cys Ala Arg Gly Val Ser Ser Asn Gly Tyr Tyr Phe
225                 230                 235                 240

Lys Leu Trp Gly Gln Gly Thr Thr Val Thr Val Ser Ser
                245                 250

<210> SEQ ID NO 118
<211> LENGTH: 253
<212> TYPE: PRT
<213> ORGANISM: Artificial Sequence
<220> FEATURE:
<223> OTHER INFORMATION: EP35minmax scFv

<400> SEQUENCE: 118

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Asn Leu
            20                  25                  30

Leu Ala Trp Tyr Gln Gln Lys Pro Gly Lys Ala Pro Lys Leu Leu Ile
        35                  40                  45

Tyr Ala Ala Ser Lys Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Gly Trp Ser His Thr Asn
                85                  90                  95

Val Asp Asn Thr Phe Gly Gln Gly Thr Lys Leu Thr Val Leu Gly Gly
            100                 105                 110

Gly Gly Gly Ser Gly Gly Gly Ser Gly Gly Gly Ser Gly Gly
        115                 120                 125

Gly Gly Ser Glu Val Gln Leu Val Glu Ser Gly Gly Ser Val Gln
    130                 135                 140

Pro Gly Gly Ser Leu Arg Leu Ser Cys Thr Ala Ser Gly Phe Ser Phe
145                 150                 155                 160

Ser Val Gly Tyr Trp Ile Cys Trp Val Arg Gln Ala Pro Gly Lys Gly
                165                 170                 175

Leu Glu Trp Val Ala Cys Ile Asp Ala Gly Thr Ser Gly Gly Thr Tyr
            180                 185                 190

Tyr Ala Thr Trp Ala Lys Gly Arg Phe Thr Ile Ser Lys Asp Thr Ser
        195                 200                 205

Lys Asn Thr Val Tyr Leu Gln Met Asn Ser Leu Arg Ala Glu Asp Thr
    210                 215                 220

Ala Thr Tyr Tyr Cys Ala Arg Gly Val Ser Ser Asn Gly Tyr Tyr Phe
225                 230                 235                 240

Lys Leu Trp Gly Gln Gly Thr Thr Val Thr Val Ser Ser
                245                 250

<210> SEQ ID NO 119
<211> LENGTH: 253
<212> TYPE: PRT
<213> ORGANISM: Artificial Sequence
<220> FEATURE:
<223> OTHER INFORMATION: EP42min scFv

<400> SEQUENCE: 119

Glu Ile Val Met Thr Gln Ser Pro Ser Thr Leu Ser Ala Ser Val Gly
1               5                   10                  15

Asp Arg Val Ile Ile Thr Cys Gln Ser Thr Glu Ser Val Tyr Lys Asn
            20                  25                  30

Asn Tyr Leu Ala Trp Tyr Gln Gln Lys Pro Gly Lys Ala Pro Lys Leu
        35                  40                  45

Leu Ile Tyr Asp Ala Ser Thr Leu Ala Ser Gly Val Pro Ser Arg Phe
    50                  55                  60

Ser Gly Ser Gly Ser Gly Ala Glu Phe Thr Leu Thr Ile Ser Ser Leu
65                  70                  75                  80

Gln Pro Asp Asp Phe Ala Thr Tyr Tyr Cys Ala Gly Tyr Tyr Arg Ser
                85                  90                  95

Gly Phe Gly Thr Ala Asn Gly Ser Phe Gly Gln Gly Thr Lys Leu Thr
            100                 105                 110

Val Leu Gly Gly Gly Gly Gly Ser Gly Gly Gly Gly Ser Gly Gly Gly
        115                 120                 125

Gly Ser Gly Gly Gly Gly Ser Glu Val Gln Leu Val Glu Ser Gly Gly
    130                 135                 140

Gly Leu Val Gln Pro Gly Gly Ser Leu Arg Leu Ser Cys Ala Ala Ser
145                 150                 155                 160

Gly Phe Thr Phe Arg Asn Asp Ala Ile Ser Trp Val Arg Gln Ala Pro
                165                 170                 175

Gly Lys Gly Leu Glu Trp Val Ser Tyr Ile Ser Asp Trp Gly Ile Lys
            180                 185                 190

```
Tyr Tyr Ala Ser Trp Val Lys Gly Arg Phe Thr Ile Ser Arg Asp Asn
            195                 200                 205

Ser Lys Asn Thr Leu Tyr Leu Gln Met Asn Ser Leu Arg Ala Glu Asp
        210                 215                 220

Thr Ala Val Tyr Tyr Cys Ala Lys Gly Ala Pro Gly Ala Gly Asp Asn
225                 230                 235                 240

Gly Ile Trp Gly Gln Gly Thr Leu Val Thr Val Ser Ser
                245                 250
```

<210> SEQ ID NO 120
<211> LENGTH: 253
<212> TYPE: PRT
<213> ORGANISM: Artificial Sequence
<220> FEATURE:
<223> OTHER INFORMATION: EP42max scFv

<400> SEQUENCE: 120

```
Glu Ile Val Met Thr Gln Ser Pro Ser Thr Leu Ser Ala Ser Val Gly
1               5                   10                  15

Asp Arg Val Ile Ile Thr Cys Gln Ser Thr Glu Ser Val Tyr Lys Asn
            20                  25                  30

Asn Tyr Leu Ala Trp Tyr Gln Gln Lys Pro Gly Lys Ala Pro Lys Leu
        35                  40                  45

Leu Ile Tyr Asp Ala Ser Thr Leu Ala Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Ala Gly Tyr Tyr Arg Ser
                85                  90                  95

Gly Phe Gly Thr Ala Asn Gly Ser Phe Gly Gln Gly Thr Lys Leu Thr
            100                 105                 110

Val Leu Gly Gly Gly Gly Ser Gly Gly Gly Ser Gly Gly Gly
        115                 120                 125

Gly Ser Gly Gly Gly Gly Ser Glu Val Gln Leu Val Glu Ser Gly Gly
        130                 135                 140

Gly Ser Val Gln Pro Gly Gly Ser Leu Arg Leu Ser Cys Thr Val Ser
145                 150                 155                 160

Gly Ile Asp Leu Arg Asn Asp Ala Ile Ser Trp Val Arg Gln Ala Pro
                165                 170                 175

Gly Lys Gly Leu Glu Trp Val Ser Tyr Ile Ser Asp Trp Gly Ile Lys
            180                 185                 190

Tyr Tyr Ala Ser Trp Val Lys Gly Arg Phe Thr Ile Ser Lys Asp Thr
        195                 200                 205

Ser Lys Asn Thr Val Tyr Leu Gln Met Asn Ser Leu Arg Ala Glu Asp
    210                 215                 220

Thr Ala Thr Tyr Tyr Cys Ala Arg Gly Ala Pro Gly Ala Gly Asp Asn
225                 230                 235                 240

Gly Ile Trp Gly Gln Gly Thr Val Thr Val Ser Ser
                245                 250
```

<210> SEQ ID NO 121
<211> LENGTH: 253
<212> TYPE: PRT
<213> ORGANISM: Artificial Sequence
<220> FEATURE:
<223> OTHER INFORMATION: EP42minmax scFv

```
<400> SEQUENCE: 121

Glu Ile Val Met Thr Gln Ser Pro Ser Thr Leu Ser Ala Ser Val Gly
1               5                   10                  15

Asp Arg Val Ile Ile Thr Cys Gln Ser Thr Glu Ser Val Tyr Lys Asn
            20                  25                  30

Asn Tyr Leu Ala Trp Tyr Gln Gln Lys Pro Gly Lys Ala Pro Lys Leu
        35                  40                  45

Leu Ile Tyr Asp Ala Ser Thr Leu Ala Ser Gly Val Pro Ser Arg Phe
    50                  55                  60

Ser Gly Ser Gly Ser Gly Ala Glu Phe Thr Leu Thr Ile Ser Ser Leu
65              70                  75                  80

Gln Pro Asp Asp Phe Ala Thr Tyr Tyr Cys Ala Gly Tyr Tyr Arg Ser
                85                  90                  95

Gly Phe Gly Thr Ala Asn Gly Ser Phe Gly Gln Gly Thr Lys Leu Thr
            100                 105                 110

Val Leu Gly Gly Gly Gly Gly Ser Gly Gly Gly Gly Ser Gly Gly Gly
        115                 120                 125

Gly Ser Gly Gly Gly Gly Ser Glu Val Gln Leu Val Glu Ser Gly Gly
    130                 135                 140

Gly Ser Val Gln Pro Gly Gly Ser Leu Arg Leu Ser Cys Thr Val Ser
145                 150                 155                 160

Gly Ile Asp Leu Arg Asn Asp Ala Ile Ser Trp Val Arg Gln Ala Pro
                165                 170                 175

Gly Lys Gly Leu Glu Trp Val Ser Tyr Ile Ser Asp Trp Gly Ile Lys
            180                 185                 190

Tyr Tyr Ala Ser Trp Val Lys Gly Arg Phe Thr Ile Ser Lys Asp Thr
        195                 200                 205

Ser Lys Asn Thr Val Tyr Leu Gln Met Asn Ser Leu Arg Ala Glu Asp
    210                 215                 220

Thr Ala Thr Tyr Tyr Cys Ala Arg Gly Ala Pro Gly Ala Gly Asp Asn
225                 230                 235                 240

Gly Ile Trp Gly Gln Gly Thr Thr Val Thr Val Ser Ser
                245                 250

<210> SEQ ID NO 122
<211> LENGTH: 5
<212> TYPE: PRT
<213> ORGANISM: Artificial Sequence
<220> FEATURE:
<223> OTHER INFORMATION: synthetic peptide

<400> SEQUENCE: 122

Gly Gly Gly Gly Ser
1               5
```

STABLE AND SOLUBLE ANTIBODIES INHIBITING TNF ALPHA

BACKGROUND OF THE INVENTION

Tumour necrosis factor alpha (TNFα, also known as cachectin), is a naturally occurring mammalian cytokine produced by numerous cell types, including monocytes and macrophages in response to endotoxin or other stimuli. TNFα is a major mediator of inflammatory, immunological, and pathophysiological reactions (Grell, M., et al. (1995) Cell, 83: 793-802).

Soluble TNFα is formed by the cleavage of a precursor transmembrane protein (Kriegler, et al. (1988) Cell 53: 45-53), and the secreted 17 kDa polypeptides assemble to soluble homotrimer complexes (Smith, et al. (1987), J. Biol. Chem. 262: 6951-6954; for reviews of TNFA, see Butler, et al. (1986), Nature 320:584; Old (1986), Science 230: 630). These complexes then bind to receptors found on a variety of cells. Binding produces an array of pro-inflammatory effects, including (i) release of other pro-inflammatory cytokines such as interleukin IL-6, IL-8, and IL-1, (ii) release of matrix metalloproteinases and (iii) up regulation of the expression of endothelial adhesion molecules, further amplifying the inflammatory and immune cascade by attracting leukocytes into extravascular tissues.

A large number of disorders are associated with elevated levels of TNFα, many of them of significant medical importance. TNFα has been shown to be up-regulated in a number of human diseases, including chronic diseases such as rheumatoid arthritis (RA), inflammatory bowel disorders including Crohn's disease and ulcerative colitis, sepsis, congestive heart failure, asthma bronchiale and multiple sclerosis. Mice transgenic for human TNFα produce high levels of TNFα constitutively and develop a spontaneous, destructive polyarthritis resembling RA (Keffer et al. 1991, EMBO J., 10,4025-4031). TNFα is therefore referred to as a pro-inflammatory cytokine.

TNFα is now well established as key in the pathogenesis of RA, which is a chronic, progressive and debilitating disease characterised by polyarticular joint inflammation and destruction, with systemic symptoms of fever and malaise and fatigue. RA also leads to chronic synovial inflammation, with frequent progression to articular cartilage and bone destruction. Increased levels of TNFα are found in both the synovial fluid and peripheral blood of patients suffering from RA. When TNFα blocking agents are administered to patients suffering from RA, they reduce inflammation, improve symptoms and retard joint damage (McKown et al. (1999), Arthritis Rheum. 42:1204-1208).

Physiologically, TNFα is also associated with protection from particular infections (Cerami. et al. (1988), Immunol. Today 9:28). TNFα is released by macrophages that have been activated by lipopolysaccharides of Gram-negative bacteria. As such, TNFα appears to be an endogenous mediator of central importance involved in the development and pathogenesis of endotoxic shock associated with bacterial sepsis (Michie, et al. (1989), Br. J. Surg. 76:670-671.; Debets. et al. (1989), Second Vienna Shock Forum, p. 463-466; Simpson, et al. (1989) Crit. Care Clin. 5: 27-47; Waage et al. (1987). Lancet 1: 355-357; Hammerle. et al. (1989) Second Vienna Shock Forum p. 715-718; Debets. et al. (1989), Crit. Care Med. 17:489-497; Calandra. et al. (1990), J. Infect. Dis. 161:982-987; Revhaug et al. (1988), Arch. Surg. 123:162-170).

As with other organ systems, TNFα has also been shown to play a key role in the central nervous system, in particular in inflammatory and autoimmune disorders of the nervous system, including multiple sclerosis, Guillain-Barre syndrome and myasthenia gravis, and in degenerative disorders of the nervous system, including Alzheimer's disease, Parkinson's disease and Huntington's disease. TNFα is also involved in disorders of related systems of the retina and of muscle, including optic neuritis, macular degeneration, diabetic retinopathy, dermatomyositis, amyotrophic lateral sclerosis, and muscular dystrophy, as well as in injuries to the nervous system, including traumatic brain injury, acute spinal cord injury, and stroke.

Hepatitis is another TNFα-related inflammatory disorder which among other triggers can be caused by viral infections, including Epstein-Barr, cytomegalovirus, and hepatitis A-E viruses. Hepatitis causes acute liver inflammation in the portal and lobular region, followed by fibrosis and tumor progression. TNFα can also mediate cachexia in cancer, which causes most cancer morbidity and mortality (Tisdale M. J. (2004), Langenbecks Arch Surg. 389:299-305).

The key role played by TNFα in inflammation, cellular immune responses and the pathology of many diseases has led to the search for antagonists of TNFα. One class of TNFα antagonists designed for the treatment of TNFα-mediated diseases are antibodies or antibody fragments that specifically bind TNFα and thereby block its function. The use of anti-TNFα antibodies has shown that a blockade of TNFα can reverse effects attributed to TNFα including decreases in IL-1, GM-CSF, IL-6, IL-8, adhesion molecules and tissue destruction (Feldmann et al. (1997), Adv. Immunol. 1997:283-350). Among the specific inhibitors of TNFα that have recently become commercially available include a monoclonal, chimeric mouse-human antibody directed against TNFα (infliximab, Remicade™; Centocor Corporation/Johnson & Johnson) has demonstrated clinical efficacy in the treatment of RA and Crohn's disease. All marketed inhibitors of TNFα are administered intravenously or subcutaneously in weekly or longer intervals as bolus injections, resulting in high starting concentrations that are steadily decreasing until the next injection. Their volume of distribution is limited.

Despite these advances, there remains a need for new and effective forms of antibodies or other immunobinders for the treatment for TNFα-associated disorders such as RA. In particular, there is an urgent need for immunobinders with optimal functional properties for the effective and continuous treatment of arthritis and other TNFα-mediated disorders which allow for more flexible administration and formulation and have an improved tissue penetration and thereby an increased volume of distribution.

SUMMARY OF THE INVENTION

Hence, it is a general object of the invention to provide a stable and soluble antibody or other immunobinder, which specifically binds TNFα in vitro and in vivo. In a preferred embodiment said immunobinder is an scFv antibody or Fab fragment.

The present invention provides stable and soluble scFv antibodies and Fab fragments specific for TNFα, which comprise specific light chain and heavy chain sequences that are optimized for stability, solubility, in vitro and in vivo binding of TNFα, and low immunogenicity. Said antibodies are designed for the diagnosis and/or treatment of TNFα-mediated disorders. The nucleic acids, vectors and host cells for expression of the recombinant antibodies of the invention, methods for isolating them and the use of said antibodies in medicine are also disclosed.

BRIEF DESCRIPTION OF THE DRAWINGS

FIG. 1A and FIG. 1B depict the relative ability of the supernatants from 44 anti-TNF RabMab hybridomas in binding TNFα (Biacore assay) and neutralising its activity (L929 assay).

FIG. 10A illustrates the potency of Epi34max and Infliximab to block cytotoxic activity of 1000 pg/ml recombinant human TNFalpha (murine L929 cells). The $IC_{50}$ for Ep34max and Infliximab was determined to be 1.04 ng/ml and 13.9 ng/m, respectively. FIG. 10B illustrates the potency of Infliximab and Ep34max (791) to block cytotoxic activity of 10 pg/ml recombinant human TNFalpha (human Kym-1 cells). The $IC_{50}$ for Infliximab and Ep34max was determined to be 14.8 ng/ml and 0.63 ng/ml respectively.

DETAILED DESCRIPTION OF THE INVENTION

It is a general object of the invention to provide stable and soluble immunobiner which specifically binds TNFα in vitro and in vivo. In a preferred embodiment said antibody derivative is a scFv antibody or Fab fragment. The immunobinders of the invention preferably comprise a light and/or heavy chain Definitions In order that the present invention may be more readily understood, certain terms will be defined as follows. Additional definitions are set forth throughout the detailed description.

The term "antibody" as used herein is a synonym for "immunoglobulin." Antibodies according to the present invention may be whole immunoglobulins or fragments thereof, comprising at least one variable domain of an immunoglobulin, such as single variable domains, Fv (Skerra A. and Pluckthun, A. (1988) *Science* 240:1038-41), scFv (Bird, R. E. et al. (1988) *Science* 242:423-26; Huston, J. S. et al. (1988) *Proc. Natl. Acad. Sci. USA* 85:5879-83), Fab, (Fab')2 or other fragments well known to a person skilled in the art.

Figure 8:
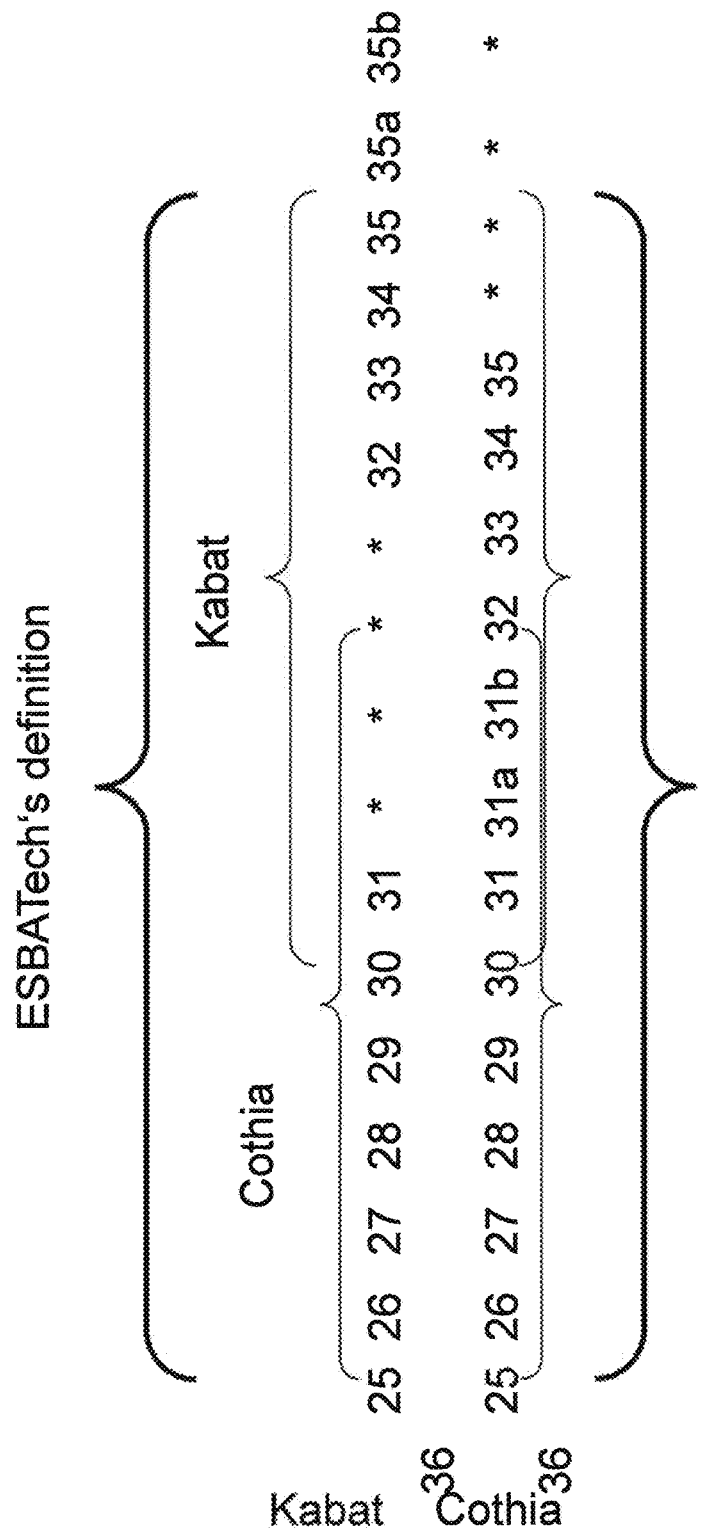
FIG. 8 depicts the CDR H1 definition used herein for grafting antigen binding sites from rabbit monoclonal antibodies into the highly soluble and stable human antibody frameworks.

The term "CDR" refers to one of the six hypervariable regions within the variable domains of an antibody that mainly contribute to antigen binding. One of the most commonly used definitions for the six CDRs was provided by Kabat E. A. et al., (1991) Sequences of proteins of immunological interest. NIH Publication 91-3242). As used herein, Kabat's definition of CDRs only apply for CDR1, CDR2 and CDR3 of the light chain variable domain (CDR L1, CDR L2, CDR L3, or L1, L2, L3), as well as for CDR2 and CDR3 of the heavy chain variable domain (CDR H2, CDR H3, or H2, H3). CDR1 of the heavy chain variable domain (CDR H1 or H1), however, as used herein is defined by the following residues (Kabat numbering): It starts with position 26 and ends prior to position 36. This is basically a fusion of CDR H1 as differently defined by Kabat and Chotia (see also FIG. 8 for illustration).

The term "antibody framework" as used herein refers to the part of the variable domain, either VL or VH, which serves as a scaffold for the antigen binding loops (CDRs) of this variable domain. In essence it is the variable domain without the CDRs.

The term "single chain antibody", "single chain Fv" or "scFv" is intended to refer to a molecule comprising an antibody heavy chain variable domain (or region; $V_H$) and an antibody light chain variable domain (or region; $V_L$) connected by a linker. Such scFv molecules can have the general structures: $NH_2$-$V_L$-linker-$V_H$-COOH or $NH_2$-$V_H$-linker-$V_L$-COOH.

The term "immunobinder" refers to a molecule that contains all or a part of the antigen binding site of an antibody, e.g., all or part of the heavy and/or light chain variable domain, such that the immunobinder specifically recognizes a target antigen. Non-limiting examples of immunobinders include full-length immunoglobulin molecules and scFvs, as well as antibody fragments, including but not limited to (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fab' fragment; (iv) a Fd fragment consisting of the $V_H$ and $C_H1$ domains; (v) a Fv fragment consisting of the $V_L$ and $V_H$ domains of a single arm of an antibody, (vi) a single domain antibody such as a Dab fragment which consists of a $V_H$ or $V_L$ domain, a Camelid, or a Shark antibody (e.g., shark Ig-NARs Nanobodies®); and (vii) a nanobody, a heavy chain region containing the variable domain and two constant domains.

The numbering systems as used herein to identify amino acid residue positions in antibody heavy and light chain variable regions corresponds to the one as defined by A. Honegger, J. Mol. Biol. 309 (2001) 657-670 (the AHo system). Conversion tables between the AHo system and the most commonly used system as defined by Kabat et al. (Kabat, E. A., et al. (1991) Sequences of Proteins of Immunological Interest, Fifth Edition, U.S. Department of Health and Human Services, NIH Publication No. 91-3242) are provided in A. Honegger, J. Mol. Biol. 309 (2001) 657-670.

The term "epitope" or "antigenic determinant" refers to a site on an antigen to which an immunoglobulin or antibody specifically binds (e.g., TNF). An epitope typically includes at least 3, 4, 5, 6, 7, 8, 9, 10, 11, 12, 13, 14 or 15 amino acids in a unique spatial conformation. See, e.g., *Epitope Mapping Protocols in Methods in Molecular Biology*, Vol. 66, G. E. Morris, Ed. (1996).

The terms "specific binding," "selective binding," "selectively binds," and "specifically binds," refer to antibody binding to an epitope on a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower.

The term "$K_D$," refers to the dissociation equilibrium constant of a particular antibody-antigen interaction. Typically, the antibodies of the invention bind to TNF with a dissociation equilibrium constant ($K_D$) of less than approximately $10^{-7}$ M, such as less than approximately $10^{-8}$ M, $10^{-9}$ M or $10^{-10}$ M or even lower, for example, as determined using surface plasmon resonance (SPR) technology in a BIACORE instrument.

As used herein, "identity" refers to the sequence matching between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are identical at that position. The "percentage identity" between two sequences is a function of the number of matching positions shared by the two sequences divided by the number of positions compared× 100. For instance, if 6 of 10 of the positions in two sequences are matched, then the two sequences have 60% identity. By way of example, the DNA sequences CTGACT and CAGGTT share 50% identity (3 of the 6 total positions are matched). Generally, a comparison is made when two sequences are aligned to give maximum identity. Such alignment can be provided using, for instance, the method of Needleman et al. (1970) *J. Mol. Biol.* 48: 443-453, implemented conveniently by computer programs such as the Align program (DNAstar, Inc.). The percent identity between two amino acid sequences can also be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (Accelrys, Inc., San Diego, Calif.), using either a Blossum 62 matrix or a PAM250 matrix, and a gap weight of 16, 14, 12, 10, 8, 6, or 4 and a length weight of 1, 2, 3, 4, 5, or 6.

"Similar" sequences are those which, when aligned, share identical and similar amino acid residues, where similar residues are conservative substitutions for corresponding amino acid residues in an aligned reference sequence. In this regard, a "conservative substitution" of a residue in a reference sequence is a substitution by a residue that is physically or functionally similar to the corresponding reference residue, e.g., that has a similar size, shape, electric charge, chemical properties, including the ability to form covalent or hydrogen bonds, or the like. Thus, a "conservative substitution modified" sequence is one that differs from a reference sequence or a wild-type sequence in that one or more conservative substitutions are present. The "percentage similarity" between two sequences is a function of the number of positions that contain matching residues or conservative substitutions shared by the two sequences divided by the number of positions compared×100. For instance, if 6 of 10 of the positions in two sequences are matched and 2 of 10 positions contain conservative substitutions, then the two sequences have 80% positive similarity.

As used herein, the term "conservative sequence modifications" is intended to refer to amino acid modifications that do not negatively affect or alter the binding characteristics of the antibody containing the amino acid sequence. Such conservative sequence modifications include nucleotide and amino acid substitutions, additions and deletions. For example, modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-VEGF antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997))

"Amino acid consensus sequence" as used herein refers to an amino acid sequence that can be generated using a matrix of at least two, and preferably more, aligned amino acid sequences, and allowing for gaps in the alignment, such that it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids.

The amino acid sequence of a protein can be analyzed at various levels. For example, conservation or variability can be exhibited at the single residue level, multiple residue level, multiple residue with gaps etc. Residues can exhibit conservation of the identical residue or can be conserved at the class level. Examples of amino acid classes include polar but uncharged R groups (Serine, Threonine, Asparagine and Glutamine); positively charged R groups (Lysine, Arginine, and Histidine); negatively charged R groups (Glutamic acid and Aspartic acid); hydrophobic R groups (Alanine, Isoleucine, Leucine, Methionine, Phenylalanine, Tryptophan, Valine and Tyrosine); and special amino acids (Cysteine, Glycine and Proline). Other classes are known to one of skill in the art and may be defined using structural determinations or other data to assess substitutability. In that sense, a substitutable amino acid can refer to any amino acid which can be substituted and maintain functional conservation at that position.

It will be recognized, however, that amino acids of the same class may vary in degree by their biophysical properties. For example, it will be recognized that certain hydrophobic R groups (e.g., Alanine, Serine, or Threonine) are more hydrophilic (i.e., of higher hydrophilicity or lower hydrophobicity) than other hydrophobic R groups (e.g., Valine or Leucine). Relative hydrophilicity or hydrophobicity can be determined using art-recognized methods (see, e.g., Rose et al., *Science*, 229: 834-838 (1985) and Cornette et al., *J. Mol. Biol.*, 195: 659-685 (1987)).

As used herein, when one amino acid sequence (e.g., a first $V_H$ or $V_L$ sequence) is aligned with one or more additional amino acid sequences (e.g., one or more VH or VL sequences in a database), an amino acid position in one sequence (e.g., the first $V_H$ or $V_L$ sequence) can be compared to a "corresponding position" in the one or more additional amino acid sequences. As used herein, the "corresponding position" represents the equivalent position in the sequence(s) being compared when the sequences are optimally aligned, i.e., when the sequences are aligned to achieve the highest percent identity or percent similarity.

"Chimeric" immunobinders as used herein have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies. Humanized antibody as used herein is a subset of chimeric antibodies.

"Humanized antibodies" as used herein are immunobinders that have been synthesized using recombinant DNA technology to circumvent immune response to foreign antigens. Humanization is a well-established technique for reducing the immunogenicity of monoclonal antibodies of xenogenic sources. A humanized antibody consists of humanized heavy chain variable region, a humanized light chain variable region and fully human constant domains. The humanization of a variable region involves the choice of an acceptor framework, typically a human acceptor framework, the extent of the CDRs from the donor immunobinder to be inserted into the variable domain acceptor framework and the substitution of residues from the donor framework into the acceptor framework. A general method for grafting CDRs into human acceptor frameworks has been disclosed by Winter in U.S. Pat. No. 5,225,539, which is hereby incorporated by reference in its entirety. U.S. Pat. No. 6,407,213 the teachings of which are incorporated by reference in its entirety, discloses a number of amino acid positions of the framework where a substitution from the donor immunobinder is preferred.

As used herein, the term "functional property" is a property of a polypeptide (e.g., an immunobinder) for which an improvement (e.g., relative to a conventional polypeptide) is desirable and/or advantageous to one of skill in the art, e.g., in order to improve the manufacturing properties or therapeutic efficacy of the polypeptide. In one embodiment, the functional property is improved stability (e.g., thermal stability). In another embodiment, the functional property is improved solubility (e.g., under cellular conditions). In yet another embodiment, the functional property is non-aggregation. In still another embodiment, the functional property is an improvement in expression (e.g., in a prokaryotic cell). In yet another embodiment the functional property is an improvement in refolding yield following an inclusion body purification process. In certain embodiments, the functional property is not an improvement in antigen binding affinity.

The term "nucleic acid molecule," refers to DNA molecules and RNA molecules. A nucleic acid molecule may be single-stranded or double-stranded, but preferably is double-stranded DNA. A nucleic acid is "operably linked" when it is placed into a functional relationship with another nucleic acid sequence. For instance, a promoter or enhancer is operably linked to a coding sequence if it affects the transcription of the sequence.

The term "vector," refers to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

The term "host cell" refers to a cell into which and expression vector has been introduced. Host cells can include bacterial, microbial, plant or animal cells. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. Suitable microbes include *Saccharomyces cerevisiae* and *Pichia pastoris*. Suitable animal host cell lines include CHO (Chinese Hamster Ovary lines) and NS0 cells.

The terms "treat," "treating," and "treatment," refer to therapeutic or preventative measures described herein. The methods of "treatment" employ administration to a subject, in need of such treatment, an antibody of the present invention, for example, a subject having a TNFα-mediated disorder or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

The term "TNF-mediated disorder" or "TNF-mediated disease" refers to any disorder, the onset, progression or the persistence of the symptoms or disease states of which requires the participation of TNF. Exemplary TNF-mediated disorders include, but are not limited to, chronic and/or autoimmune states of inflammation in general, immune mediated inflammatory disorders in general, inflammatory CNS disease, inflammatory diseases affecting the eye, joint, skin, mucuous membranes, central nervous system, gastrointestinal tract, urinary tract or lung, states of uveitis in general, retinitis, HLA-B27+ uveitis, Behcet's disease, dry eye syndrome, glaucoma, Sjögren syndrome, diabetes mellitus (incl. diabetic neuropathy), insulin resistance, states of arthritis in general, rheumatoid arthritis, osteoarthritis, reactive arthritis and Reiter's syndrome, juvenile arthritis, ankylosing spondylitis, multiple sclerosis, Guillain-Barre syndrome, myasthenia gravis, amyotrophic lateral sclerosis, sarcoidosis, glomerulonephritis, chronic kidney disease, cystitis, psoriasis (incl. psoriatic arthritis), hidradenitis suppurativa, panniculitis, pyoderma gangrenosum, SAPHO syndrome (synovitis, acne, pustulosis, hyperostosis and osteitis), acne, Sweet's sydrome, pemphigus, Crohn's disease (incl. extraintestinal manifestastations), ulcerative colitis, asthma bronchiale, hypersensitivity pneumonitis, general allergies, allergic rhinitis, allergic sinusitis, chronic obstructive pulmonary disease (COPD), lung fibrosis, Wegener's granulomatosis, Kawasaki syndrome, Giant cell arteritis, Churg-Strauss vasculitis, polyarteritis nodosa, burns, graft versus host disease, host versus graft reactions, rejection episodes following organ or bone marrow transplantation, sytemic and local states of vasculitis in general, systemic and discoid lupus erythematodes, polymyositis and dermatomyositis, sclerodermia, pre-eclampsia, acute and chronic pancreatitis, viral hepatitis, alcoholic hepatitis, post-surgical inflammation such as after eye surgery (e.g. cataract (eye lens replacement) or glaucoma surgery), joint surgery (incl. arthroscopic surgery), surgery at joint-related structures (e.g. ligaments), oral and/or dental surgery, minimally invasive cardiovascular procedures (e.g. PTCA, atherectomy, stent placement), laparoscopic and/or endoscopic intra-abdominal and gynecological procedures, endoscopic urological procedures (e.g. prostate surgery, ureteroscopy, cystoscopy, interstitial cystitis), or perioperative inflammation (prevention) in general, Alzheimer disease, Parkinson's disease, Huntington's disease, Bell' palsy, Creutzfeld-Jakob disease. Cancer-related osteolysis, cancer-related inflammation, cancer-related pain, cancer-related cachexia, bone metastases, acute and chronic forms of pain, irrespective whether these are caused by central or peripheral effects of TNFα and whether they are classified as inflammatory, nociceptive or neuropathic forms of pain, sciatica, low back pain, carpal tunnel syndrome, complex regional pain syndrome (CRPS), gout, postherpetic neuralgia, fibromyalgia, local pain states, chronic pain syndroms due to metastatic tumor, dismenorrhea. Bacterial, viral or fungal sepsis, tuberculosis, AIDS, atherosclerosis, coronary artery disease, hypertension, dyslipidemia, heart insufficiency and chronic heart failure. The term "effective dose" or "effective dosage" refers to an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

The term "subject" refers to any human or non-human animal. For example, the methods and compositions of the present invention can be used to treat a subject with a TNF-mediated disorder.

The term "lagomorphs" refers to members of the taxonomic order Lagomorpha, comprising the families Leporidae (e.g. hares and rabbits), and the Ochotonidae (pikas). In a most preferred embodiment, the lagomorphs is a rabbit. The term "rabbit" as used herein refers to an animal belonging to the family of the leporidae.

Different nomenclatures were used for the generated immunobinders. These are typically identified by a number (e.g. #34). In those cases where a prefix such as EP or Epi was used (e.g. EP 34 which is identical to Epi 34 or to #34), the same immunobinder is thereby indicated.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Various aspects of the invention are described in further detail in the following subsections. It is understood that the various embodiments, preferences and ranges may be combined at will. Further, depending of the specific embodiment, selected definitions, embodiments or ranges may not apply.

Anti-TNFα Antibodies

In one aspect, the present invention provides immunobinders that bind TNFα and thus are suitable to block the function of TNFα in vivo. The CDRs of these immunobinders are derived from rabbit anti-TNFα monoclonal antibodies as disclosed in U.S. Pat. No. 7,431,927. Rabbit antibodies are known to have particularly high affinities. Moreover, the CDR sequences disclosed herein are natural sequences, which means that no affinity maturation of the resulting immunobinders needs to be performed. In a preferred embodiment, the immunobinder neutralizes TNFα in vivo.

In certain embodiments, the invention provides an immunobinder, which specifically binds TNFα, comprising at least one of a CDRH1, a CDRH2, a CDRH3, a CDRL1, a CDRL2, or a CDRL3 amino acid sequence. Exemplary CDR amino acid sequences for use in the immunobinders of the invention are set forth in SEQ ID Nos: 3-50 (Table 1). The CDRs set forth in SEQ ID Nos: 3-50 can be grafted onto any suitable binding scaffold using any art recognized methods (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.). The CDRs from different parent antibodies may be combined into one antibody to generate additional antibody species. However, it is preferred that the immunobinders disclosed herein are humanized, thus being suitable for therapeutic applications.

Thus, in one embodiment, the invention provides an immunobinder which specifically binds human TNFα, the immunobinder comprising:
  (i) a humanized heavy chain variable region (VH), the heavy chain variable region comprising a human heavy chain variable framework sequence and CDR H1, CDR H2 and CDR H3 sequences stemming from a rabbit immunobinder; and/or
  (ii) a humanized light chain variable region (VL), the light chain variable region comprising a human light chain variable framework sequence and CDR L1, CDR L2 and CDR L3 sequences stemming from a rabbit immunobinder.

As known in the art, many rabbit VH chains have extra paired cysteines relative to the murine and human counterparts. In addition to the conserved disulfide bridge formed between cys22 and cys92, there is also a cys21-cys79 bridge as well as an interCDR S-S bridge formed between the last residue of CDRH1 and the first residue of CDR H2 in some rabbit chains. Besides, pairs of cysteine residues are often found in the CDR-L3. Besides, many rabbit antibody CDRs do not belong to any previously known canonical structure. In particular the CDR-L3 is often much longer than the CDR-L3 of a human or murine counterpart.

Further to rabbits, the invention may be used for grafting CDRs of any lagomorph.

In the case of antibodies, the rabbit CDRs set forth in SEQ ID Nos: 3-50 may be grafted into the framework regions of any antibody from any species. However, it has previously been discovered that antibodies or antibody derivatives comprising the frameworks identified in the so called "quality control" screen (WO0148017) are characterised by a generally high stability and/or solubility and thus may also be useful in the context of extracellular applications such as neutralizing human TNFα. Moreover, it has further been discovered that one particular combination of these VL (variable light chain) and VH (variable heavy chain) soluble and stable frameworks is particularly suited to accommodating rabbit CDRs. It was surprisingly found that upon grafting into said framework or its derivatives, loop conformation of a large variety of rabbit CDRs could be fully maintained, largely independent of the sequence of the donor framework. Moreover, said framework or its derivatves containing different rabbit CDRs are well expressed and good produced contrary to the rabbit wild type single chains and still almost fully retain the affinity of the original donor rabbit antibodies. Accordingly, in one embodiment, the CDRs set forth in SEQ ID Nos: 3-50 are grafted into the human antibody frameworks derived by "quality control" screening disclosed in EP1479694. The amino acid sequences of exemplary frameworks for use in the invention are set forth in SEQ ID Nos: 1 and 2 below.

```
Variable light chain of FW1.4
                                    SEQ ID No 1
EIVMTQSPSTLSASVGDRVIITC(X)_{n=3-50}WYQQKPGKAPKLLIY
(X)_{n=3-50}VPSRFSGSGSGAEFTLTISSLQPDDFATYYC(X)_{n=3-50}
FGQGTKLTVLG Variable heavy chain of FW1.4
                                    SEQ ID No 2
EVQLVESGGGLVQPGGSLRLSCAAS(X)_{n=3-50}WVRQAPGKGLEWVS
(X)_{n=3-50}RFTISRDNSKNTLYLQMNSLRAEDTAVYYCAK(X)_{n=3-50}
WGQGTLVTVSS
```

X can be any naturally occurring amino acid. At least three and up to 50 amino acids can be present. The CDRs are typically inserted into the sites where X is present.

In other embodiments, the invention provides an immunobinder, which specifically binds TNFα, comprising at least one of a VH or a VL amino acid sequence.

Exemplary VH or VL amino acid sequences for use in the immunobinders of the invention are set forth in SEQ ID Nos: 51-111.

In certain embodiments, the invention further provides an immunobinder, which specifically binds TNFα, comprising an amino acid sequence with substantial similarity to an amino acid sequence set forth in SEQ ID Nos: 51-111, and wherein the immunobinder retains or improves the desired functional properties of the anti-TNFα immunobinder of the invention. Exemplary percentage similarities include, but are not limited to, about 50%, 60%, 70%, 75%, 80%, 85%, 90% or 95% identity.

In certain embodiments, the invention further provides an immunobinder, which specifically binds TNFα, comprising an amino acid sequence with substantial identity to an amino acid sequence set forth in SEQ ID Nos: 51-111, and wherein the immunobinder retains or improves the desired functional properties of the anti-TNFα immunobinder of the invention.

Exemplary percentage identities include, but are not limited to, about 50%, 60%, 70%, 75%, 80%, 85%, 90% or 95% identity.

In certain embodiments, the invention further provides an immunobinder, which specifically binds TNFα, comprising an amino acid sequence with conservative substitutions relative to an amino acid sequence set forth in SEQ ID Nos: 51-111, and wherein the immunobinder retains or improves the desired functional properties of the anti-TNFα immunobinder of the invention.

In a most preferred embodiment, the immunobinder of the invention comprises at least one CDR sequence being at least 80%, more preferably at least 85%, 90%, 95% or 100% identical to anyone of the SEQ ID Nos: 3-50.

In a preferred embodiment of the invention, an immunobinder is provided comprising at least one, preferably two, three, four, five or most preferably six CDRs of the group consisting of SEQ ID Nos 3-8.

In another preferred embodiment of the invention, an immunobinder is provided comprising at least one, preferably two, three, four, five or most preferably six CDRs of the group consisting of SEQ ID Nos 9-14.

In another preferred embodiment of the invention, an immunobinder is provided comprising at least one, preferably two, three, four, five or most preferably six CDRs of the group consisting of SEQ ID Nos: 15-20.

In another preferred embodiment of the invention, an immunobinder is provided comprising at least one, preferably two, three, four, five or most preferably six CDRs of the group consisting of SEQ ID Nos: 21-26.

In another preferred embodiment of the invention, an immunobinder is provided comprising at least one, preferably two, three, four, five or most preferably six CDRs of the group consisting of SEQ ID Nos: 27-32.

In another preferred embodiment of the invention, an immunobinder is provided comprising at least one, preferably two, three, four, five or most preferably six CDRs of the group consisting of SEQ ID Nos: 33-38.

In another preferred embodiment of the invention, an immunobinder is provided comprising at least one, preferably, two, three, four, five or most preferably six CDRs of the group consisting of SEQ ID Nos: 39-44.

In another preferred embodiment of the invention, an immunobinder is provided comprising at least one, preferably two, three, four, five or most preferably six CDRs of the group consisting of SEQ ID Nos: 45-50.

The CDR sequences provided herein in SEQ ID Nos: 3-50 may further comprise substitutions. Preferably, the sequences have 3, more preferably 2, and most preferably only one substitution(s). Said substitutions are preferably such that the selective binding capacity of the immunobinder is not impaired but the affinity of the immunobinder is altered, preferably enhanced.

TABLE 1

Rabmab Donor CDRs

| Rabmab Clone | CDR | Amino Acid Sequence | SEQ ID NO: |
|---|---|---|---|
| EP-43 | CDR-H1 | GFSLSSGAMS | 3 |
|  | CDR-H2 | VIISSGATYYASWAKG | 4 |
|  | CDR-H3 | GGPDDSNSMGTFDP | 5 |
|  | CDR-L1 | QASQSISDWLA | 6 |
|  | CDR-L2 | GASRLAS | 7 |
|  | CDR-L3 | QQGWSDSYVDNL | 8 |

TABLE 1-continued

Rabmab Donor CDRs

| Rabmab Clone | CDR | Amino Acid Sequence | SEQ ID NO: |
|---|---|---|---|
| EP-1 | CDR-H1 | GIDLSNDAIS | 9 |
| | CDR-H2 | YISDWSIRYYANWAQG | 10 |
| | CDR-H3 | GAPGAGDNGI | 11 |
| | CDR-L1 | QSTESVYKNNYLA | 12 |
| | CDR-L2 | DASTLAS | 13 |
| | CDR-L3 | AGYYRSGSGTANGS | 14 |
| EP-6 | CDR-H1 | GFSLSRYGVS | 15 |
| | CDR-H2 | TIGEAGRAYYANWARS | 16 |
| | CDR-H3 | GEVFNNGWGAFNI | 17 |
| | CDR-L1 | QASESIYSGLA | 18 |
| | CDR-L2 | QASTLAS | 19 |
| | CDR-L3 | QQGFGTSNVENP | 20 |
| EP-15 | CDR-H1 | GFSLSRYGVS | 21 |
| | CDR-H2 | AIGETGRAYYANWAKS | 22 |
| | CDR-H3 | GEEFNNGWGAFNI | 23 |
| | CDR-L1 | QASENIYTSLA | 24 |
| | CDR-L2 | SASTLAS | 25 |
| | CDR-L3 | QQGFGTSNVENP | 26 |
| EP-19 | CDR-H1 | GFSLNSNEIS | 27 |
| | CDR-H2 | YIGNGGMTHYASWAKG | 28 |
| | CDR-H3 | SVEYTDLYYLNI | 29 |
| | CDR-L1 | QASDNIYRGLA | 30 |
| | CDR-L2 | DASTLQS | 31 |
| | CDR-L3 | LGVYGYSSDDGAA | 32 |
| EP-34 | CDR-H1 | GFTISRSYWIC | 33 |
| | CDR-H2 | CIYGDNDITPLYANWAKG | 34 |
| | CDR-H3 | LGYADYAYDL | 35 |
| | CDR-L1 | QSSQSVYGNIWMA | 36 |
| | CDR-L2 | QASKLAS | 37 |
| | CDR-L3 | QGNFNTGDRYA | 38 |
| EP-35 | CDR-H1 | GFSFSVGYWIC | 39 |
| | CDR-H2 | CIDAGTSGGTYYATWAKG | 40 |
| | CDR-H3 | GVSSNGYYFKL | 41 |
| | CDR-L1 | QASQSISNLLA | 42 |
| | CDR-L2 | AASKLAS | 43 |
| | CDR-L3 | QQGWSHTNVDNT | 44 |
| EP-42 | CDR-H1 | GIDLRNDAIS | 45 |
| | CDR-H2 | YISDWGIKYYASWVKG | 46 |
| | CDR-H3 | GAPGAGDNGI | 47 |
| | CDR-L1 | QSTESVYKNNYLA | 48 |
| | CDR-L2 | DASTLAS | 49 |
| | CDR-L3 | AGYYRSGFGTANG | 50 |

In another embodiment, the invention provides antibodies that bind to an epitope on human TNFα as is recognized by a monoclonal antibody containing a set of CDRs (H1-H3, L1-L3; belonging to one Rabmab clone) as set forth in Table 1. Such antibodies can be identified based on their ability to cross-compete with an antibody of Table 1 in a standard TNF binding assay. The ability of a test antibody to inhibit the binding of an antibody of Table 1 to human TNFα demonstrates that the test antibody can compete with the antibody of Table 1 for binding to human TNFα and thus involves the same epitope on human TNFα as the antibody of Table 1. In a preferred embodiment, the antibody that binds to the same epitope on human TNFα as the antibodies set forth in Table 1 is a human monoclonal antibody. Such human monoclonal antibodies can be prepared and isolated as described herein.

In one embodiment, antibodies and antibody fragments of the present invention are single-chain antibodies (scFv) or Fab fragments. In the case of scFv antibodies, a selected VL domain can be linked to a selected VH domain in either orientation by a flexible linker. A suitable state of the art linker consists of repeated GGGGS (SEQ ID NO: 122) amino acid sequences or variants thereof. In a preferred embodiment of the present invention a (GGGGS)$_4$ linker (SEQ ID No: 72) or its derivative is used, but variants of 1-3 repeats are also possible (Holliger et al. (1993), Proc. Natl. Acad. Sci. USA 90:6444-6448). Other linkers that can be used for the present invention are described by Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol. Immunother. 50:51-59. The arrangement can be either NH$_2$-VL-linker-VH-COOH or NH$_2$-VH-linker-VL-COOH, with the former orientation being the preferred one. In the case of Fab fragments, selected light chain variable domains VL are fused to the constant region of a human Ig kappa chain, while the suitable heavy chain variable domains VH are fused to the first (N-terminal) constant domain CH1 of a human IgG. At the C-terminus, an inter-chain disulfide bridge is formed between the two constant domains.

The antibodies or antibody derivatives of the present invention can have affinities to human TNF with dissociation constants $K_d$ in a range of 1 fM-10 μM. In a preferred embodiment of the present invention the $K_d$ is ≤1 nM. The affinity of an antibody for an antigen can be determined experimentally using a suitable method (Berzofsky et al. "Antibody-Antigen Interactions", in *Fundamental Immunology*, Paul, W. E., Ed, Raven Press: New York, N.Y. (1992); Kuby, *J. Immunology*, W.H. Freeman and Company: New York, N.Y.) and methods described therein.

Preferred antibodies include antibodies having a variable heavy (VH) and/or variable light (VL) chain region from among the following VH and VL sequences (CDR sequences underlined):

EP43min VH
SEQ ID NO: 51
EVQLVESGGGLVQPGGSLRLSCAASGFSLSSGAMSWVRQAPGKGLEWVSV
IISSGATYYASWAKGRFTISRDNSKNTLYLQMNSLRAEDTAVYYCAKGGP
DDSNSMGTFDPWGQGTLVTVSS EP43min VL
SEQ ID NO: 52
EIVMTQSPSTLSASVGDRVIITCQASQSISDWLAWYQQKPGKAPKLLIYG
ASRLASGVPSRFSGSGSGAEFTLTISSLQPDDFATYYCQQGWSDSYVDNL
FGQGTKLTVLG EP43max VH
SEQ ID NO: 53
EVQLVESGGGLVQPGGSLRLSCTVSGFSLSSGAMSWVRQAPGKGLEWVGV
IISSGATYYASWAKGRFTISKDTSKNTVYLQMNSLRAEDTAVYYCARGGP
DDSNSMGTFDPWGQGTLVTVSS EP43max VL
SEQ ID NO: 54
EIVMTQSPSTLSASVGDRVIIKCQASQSISDWLAWYQQKPGKAPKLLIYG
ASRLASGFPSRFSGSGSGAEFTLTISGLEPADFATYYCQQGWSDSYVDNL
FGQGTKLTVLG EP43maxDHP VH
SEQ ID NO: 55
EVQLVESGGGSVQPGGSLRLSCTVSGFSLSSGAMSWVRQAPGKGLEWVGV
IISSGATYYASWAKGRFTISKDTSKNTVYLQMNSLRAEDTATYYCARGGP
DDSNSMGTFDPWGQGTSVTVSS EP43minmaxVL:T22K VL
SEQ ID NO: 56
EIVMTQSPSTLSASVGDRVIIKCQASQSISDWLAWYQQKPGKAPKLLIYG
ASRLASGVPSRFSGSGSGAEFTLTISSLQPDDFATYYCQQGWSDSYVDNL
FGQGTKLTVLG -continued EP43minmaxVL:V58F VL

SEQ ID NO: 57

EIVMTQSPSTLSASVGDRVIITCQASQSISDWLAWYQQKPGKAPKLLIY**G
ASRLASGFPSRFSGSGSGAEFTLTISSLQPDDFATYYCQQGWSDSYVDNL**
FGQGTKLTVLG

EP43minmaxVL:Q79E VL

SEQ ID NO: 58

EIVMTQSPSTLSASVGDRVIITCQASQSISDWLAWYQQKPGKAPKLLIY**G
ASRLASGVPSRFSGSGSGAEFTLTISSLEPDDFATYYCQQGWSDSYVDNL**
FGQGTKLTVLG

EP43minmaxVL:D81A VL

SEQ ID NO: 59

EIVMTQSPSTLSASVGDRVIITCQASQSISDWLAWYQQKPGKAPKLLIY**G
ASRLASGVPSRFSGSGSGAEFTLTISSLQPADFATYYCQQGWSDSYVDNL**
FGQGTKLTVLG

EP1min VH

SEQ ID NO: 60

EVQLVESGGGLVQPGGSLRLSCAASGFTFSNDAISWVRQAPGKGLEWVS**Y
ISDWSIRYYANWAQGRFTISRDNSKNTLYLQMNSLRAEDTAVYYCAKGAP
GAGDNGI**WGQGTLVTVSS

NOTE:
EP1min CDR-H1 does not match that of EP1max

EP1min VL

SEQ ID NO: 61

EIVMTQSPSTLSASVGDRVIITCQSTESVYKNNYLAWYQQKPGKAPKLLI
YDASTLASGVPSRFSGSGSGAEFTLTISSLQPDDFATYYC**AGYYRSGSGT
ANGS**FGQGTKLTVLG

EP1max VH

SEQ ID NO: 62

EVQLVESGGGSVQPGGSLRLSCTVSGIDLSNDAISWVRQAPGKGLEWVA**Y
ISDWSIRYYANWAQGRFTISKDTSKNTVYLQMNSLRAEDTATYYCARGAP
GAGDNGI**WGQGTTVIVSS

EP1max VL

SEQ ID NO: 63

EIVMTQSPSTLSASVGDRVIITCQSTESVYKNNYLAWYQQKPGKAPKLLI
YDASTLASGVPSRFSGSGSGTEFTLTISSLQPDDFATYYC**AGYYRSGSGT
ANGS**FGQGTKLTVLG

SEQ ID NO: 64

EP6min VH
EVQLVESGGGLVQPGGSLRLSCAASGFSLSRYGVSWVRQAPGKGLEWVS**T
IGEAGRAYYANWARSRFTISRDNSKNTLYLQMNSLRAEDTAVYYCAKGEV
FNNGWGAFNI**WGQGTLVTVSS EP6min VL

SEQ ID NO: 65

EIVMTQSPSTLSASVGDRVIITCQASESIYSGLAWYQQKPGKAPKLLIY**Q
ASTLASGVPSRFSGSGSGAEFTLTISSLQPDDFATYYCQQGFGTSNVENP**
FGQGTKLTVLG

EP6max VH

SEQ ID NO: 66

EVQLVESGGGLVQPGGSLRLSCTVSGFSLSRYGVSWVRQAPGKGLEWVG**T
IGEAGRAYYANWARSRSTISRDTSKNTVYLQMNSLRAEDTAVYYCARGEV
FNNGWGAFNI**WGQGTLVTVSS

EP6max VL

SEQ ID NO: 67

EIVMTQSPSTLSASVGDRVIITCQASESIYSGLAWYQQKPGKAPKLLIY**Q
ASTLASGVPSRFSGSGSGTDFTLAISSLQPDDFATYYCQQGFGTSNVENP**
FGQGTKLTVLG

EP15min VH

SEQ ID NO: 68

EVQLVESGGGLVQPGGSLRLSCAASGFTFSRYGVSWVRQAPGKGLEWVS**A
IGETGRAYYANWAKSRFTISRDNSKNTLYLQMNSLRAEDTAVYYCAKGEE
FNNGWGAFNI**WGQGTLVTVSS

EP15min VL

SEQ ID NO: 69

EIVMTQSPSTLSASVGDRVIITCQASENIYTSLAWYQQKPGKAPKLLIY**S
ASTLASGVPSRFSGSGSGAEFTLTISSLQPDDFATYYCQQGFATSNVENP**
FGQGTKLTVLG

EP15max VH

SEQ ID NO: 70

EVQLVESGGGSVQPGGSLRLSCTVSGFSLSRYGVSWVRQAPGKGLEWVGA
IGETGRAYYANWAKSRSTISRDTSKNTVYLQMNSLRAEDTATYYCARGEE
FNNGWGAFNI**WGQGTTVTVSS

EP15max VL

SEQ ID NO: 71

EIVMTQSPSTLSASVGDRVIITCQASENIYTSLAWYQQKPGKAPKLLIY**S
ASTLASGVPSRFSGSGSGTEFTLTISSLQPDDFATYYCQQGFATSNVENP**
FGQGTKLTVLG

SEQ ID NO: 72 glycine-serine linker
GGGGSGGGGSGGGGSGGGGS

EP19maxmod VH

SEQ ID NO: 73

EVQLVESGGGLVQPGGSLRLSCTVSGFSLNSNEISWVRQAPGKGLEWVG**Y
IGNGGMTHYASWAKGRFTISRDTSKNTVYLQMNSLRAEDTAVYYCASSVE
YTDLYYLNI**WGQGTLVTVSS

EP19maxmod VL

SEQ ID NO: 74

EIVMTQSPSTLSASVGDRVIITCQASDNIYRGLAWYQQKPGKAPKLLIY**D
ASTLQSGVPSRFSGSGSGTQFTLTISSLQPDDFATYYCLGVYGYSSDDGA
A**FGQGTKLTVLG

EP19minmod VH

SEQ ID NO: 75

EVQLVESGGGLVQPGGSLRLSCAASGFSLNSNEISWVRQAPGKGLEWVS**Y
IGNGGMTHYASWAKGRFTISRDNSKNTLYLQMNSLRAEDTAVYYCAKSVE
YTDLYYLNI**WGQGTLVTVSS

EP19minmod VL

SEQ ID NO: 76

EIVMTQSPSTLSASVGDRVIITCQASDNIYRGLAWYQQKPGKAPKLLIY**D
ASTLQSGVPSRFSGSGSGAEFTLTISSLQPDDFATYYCLGVYGYSSDDGA
A**FGQGTKLTVLG

EP34min VH

SEQ ID NO: 77

EVQLVESGGGLVQPGGSLRLSCAASGFTISRSYWICWVRQAPGKGLEWVS
CIYGDNDITPLYANWAKGRFTISRDNSKNTLYLQMNSLRAEDTAVYYCAK
LGYADYAYDLWGQGTLVTVSS

EP34min VL

SEQ ID NO: 78

EIVMTQSPSTLSASVGDRVIITCQSSQSVYGNIWMAWYQQKPGKAPKLLI
YQASKLASGVPSRFSGSGSGAEFTLTISSLQPDDFATYYC**QGNFNTGDRY
A**FGQGTKLTVLG

EP34max VH

SEQ ID NO: 79

EVQLVESGGGLVQPGGSLRLSCTASGFTISRSYWICWVRQAPGKGLEWVA
CIYGDNDITPLYANWAKGRFPVSTDISKNTVYLQMNSLRAEDTAVYYCAR
LGYADYAYDLWGQGTLVTVSS

EP34max VL

SEQ ID NO: 80

EIVMTQSPSTLSASLGDRVIITCQSSQSVYGNIWMAWYQQKSGKAPKLLI
YQASKLASGVPSRFSGSGSGAEFSLTISSLQPDDFATYYC**QGNFNTGDRY
A**FGQGTKLTVLG

EP35min VH

SEQ ID NO: 81

EVQLVESGGGLVQPGGSLRLSCAASGFTFSVGYWICWVRQAPGKGLEWVS
CIDAGTSGGTYYATWAKGRFTISRDNSKNTLYLQMNSLRAEDTAVYYCAK
GVSSNGYYFKLWGQGTLVTVSS

EP35min VL

SEQ ID NO: 82

EIVMTQSPSTLSASVGDRVIITCQASQSISNLLAWYQQKPGKAPKLLIY**A
ASKLASGVPSRFSGSGSGAEFTLTISSLQPDDFATYYCQQGWSHTNVDNT**
FGQGTKLTVLG

EP35max VH

SEQ ID NO: 83

EVQLVESGGGSVQPGGSLRLSCTASGFSFSVGYWICWVRQAPGKGLEWVA
CIDAGTSGGTYYATWAKGRFTISKDTSKNTVYLQMNSLRAEDTATYYCAR
GVSSNGYYFKLWGQGTTVTVSS

-continued

EP35max VL

SEQ ID NO: 84

EIVMTQSPSTLSASVGDRVIITCQASQSISNLLAWYQQKPGKAPKLLIV**A
ASKLASGVPSRFSGSGSGTEFTLTISSLQPDDFATYYCQQGWSHTNVDNT**
FGQGTKLTVLG

EP42min VH

SEQ ID NO: 85

EVQLVESGGGLVQPGGSLRLSCAASGFTFRNDAISWVRQAPGKGLEWVS**Y
ISDWGIKYYASWVKGRFTISRDNSKNTLYLQMNSLRAEDTAVYYCAKGAP
GAGDNGI**WGQGTLVTVSS
NOTE:
EP42min CDR-H1 does not match that of EP42max EP42min VL

SEQ ID NO: 86

EIVMTQSPSTLSASVGDRVIITCQSTESVYKNNYLAWYQQKPGKAPKLLI
YDASTLASGVPSRFSGSGSGAEFTLTISSLQPDDFATYYC**AGYYRSGFGT
ANG**SFGQGTKLTVLG

EP42max VH

SEQ ID NO: 87

EVQLVESGGGSVQPGGSLRLSCTVSGIDLRNDAISWVRQAPGKGLEWVS**Y
ISDWGIKYYASWVKGRFTISKDTSKNTVYLQMNSLRAEDTATYYCARGAP
GAGDNGI**WGQGTTVIVSS

EP42max VL

SEQ ID NO: 88

EIVMTQSP
STLSASVGDRVIITCQSTESVYKNNYLAWYQQKPGKAPKLLIYDASTLAS
GVPSRFSGSGSGTEFTLTISSLQPDDFATYYCAGYYRSGFGTANGSFGQG
TKLTVLG

Production of Anti-TNF Antibodies

The present invention is based, at least in part, on the discovery that the highly soluble and stable human antibody frameworks identified by a Quality Control (QC) assay are particularly suitable frameworks for accommodating CDRs from other non-human animal species, for example, rabbit CDRs. In particular, the invention is based on the discovery that the light and heavy chain variable regions of particular human antibody (the so called, "FW 1.4" antibody) are particularly suitable as acceptors for CDRs from a variety of rabbit antibodies of different binding specificities. Although ESBATech's human single-chain framework FW1.4 clearly underperformed in the Quality Control assay and when expressed in HeLa cells when used together with its original CDRs (as disclosed in WO03097697), it was surprisingly found that, when combined with other CDRs, such as rabbit CDRs, it gives rise to very stable, soluble and well producible single-chain antibodies. Furthermore, humanized immunobinders generated by the grafting of rabbit CDRs into these highly compatible light and heavy frameworks consistently and reliably retain the binding properties of the rabbit antibodies from which the donor CDRs are derived. Moreover, immunobinders generated by the methods of the invention reliably exhibit superior functional properties such as solubility and stability. Accordingly, it is a general object of the invention to provide methods for grafting rabbit and other non-human CDRs, into the soluble and stable light chain and/or heavy chain human antibody frameworks of SEQ ID NO:1 (K127) and SEQ ID NO:2 (a43), respectively, thereby generating humanized antibodies with superior biophysical properties.

In a preferred embodiment, the framework comprises one or more substitutions in the heavy chain framework (VH) at a position from the group consisting of positions H24, H25, H56, H82, H84, H89 and H108 (AHo numbering system). Additionally or alternatively, the framework may comprise a substitution in the light chain framework (VH) at position L87 according to the AHo numbering system. The presence of said substitutions have shown to provide an acceptor framework which almost fully retains the affinity of the original donor antibodies. In a more preferred embodiment, the one or more of substitutions selected from the group consisting of: threonine (T) at position H24, valine (V) at position H25, glycine (G) or alanine (A) at position H56, lysine (K) at position H82, threonine (T) at position H84, valine (V) at position H89 and arginine (R) at position H108 and threonine (T) at position L87 according to the AHo numbering system are present in the framework sequence.

Thus, in an even more preferred embodiment, the acceptor framework is

SEQ ID NO. 89: variable heavy chain framework of rFW1.4
EVQLVESGGGLVQPGGSLRLSCTAS(X)$_{n=3-50}$ WVRQAPGKGLEWVG (X)$_{n=3-50}$RFTISRDTSKNTVYLQMNSLRAEDTAVYYCAR$_{n=3-50}$

WGQGTLVTVSS

SEQ ID NO. 90: variable heavy chain framework of rFW1.4(V2)
EVQLVESGGGLVQPGGSLRLSCTVS(X)$_{n=3-50}$ WVRQAPGKGLEWVG (X)$_{n=3-50}$RFTISKDTSKNTVYLQMNSLRAEDTAVYYCAR$_{n=3-50}$

WGQGTLVTVSS

SEQ ID NO. 91: substituted variable light chain framework of FW1.4
EIVNITQSPSTLSASVGDRVIITC(X)$_{n=3-50}$ WYQQKPGKAPKLLIY $_{n=3-50}$GVPSRFSGSGSGTEFTLTISSLQPDDFATYYC (X)$_{n=3-50}$FGQGTKLTVLG SEQ ID NO. 92: framework of rFW1.4
EIVMTQSPSTLSASVGDRVIITC(X)$_{n=3-50}$ WYOQKPGKAPKLLIY (X)$_{n=3-50}$GVPSRFSGSGSGTEFTLTISSLQPDDFATYYC(X)$_{n=3-50}$

FGQGTKLTVLGGGGSGGGGSGGGGSGGGGSEVQLVESGGGLVQPGGSLR

LSCTAS(X)$_{n=3-50}$ WVRQAPGKGLEWVG(X)$_{n=3-50}$

RFTISRDTSKNTVYLQMNSLRAEDTAVYYCAR(X)$_{n=3-50}$

WGQGTLVTVSS

SEQ ID NO. 93: framework of rFW1.4(V2)
EIVMTQSPSTLSASVGDRVIITC(X)$_{n=3-50}$ WYOQKPGKAPKLLIY (X)$_{n=3-50}$GVPSRFSGSGSGTEFTLTISSLQPDDFATYYC (X)$_{n=3-50}$FGQGTKLTVLGGGGSGGGGSGGGGSGGGGSEVQLVESGGGL VQPGGSLRLSCTVS(X)$_{n=3-50}$WVRQAPGKGLEWVG (X)$_{n=3-50}$RFTISKDTSKNTVYLQMNSLR AEDTAVYYCAR(X)$_{n=3-50}$ WGQGTLVTVSS X can be any naturally occurring amino acid; at least three and up to 50 amino acids can be present. The CDRs are typically inserted into the sites where X is present.

The antibodies or antibody derivatives of the present invention may be generated using routine techniques in the field of recombinant genetics. Knowing the sequences of the polypeptides, the cDNAs encoding them can be generated by gene synthesis by methods well known in the art. These cDNAs can be cloned into suitable vector plasmids. Once the DNA encoding a VL and/or a VH domain are obtained, site directed mutagenesis, for example by PCR using mutagenic primers, can be performed to obtain various derivatives. The best "starting" sequence can be chosen depending on the number of alterations desired in the VL and/or VH sequences. A preferred sequence is the TB-A sequences and its derivatives, e.g. scFv sequences or Fab fusion peptide sequences, may be chosen as templates for PCR driven mutagenesis and/or cloning.

Methods for incorporating or grafting CDRs into framework regions include those set forth in, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al, as well as those disclosed in U.S. Provisional Application Ser. Nos. 61/075,697 and 61/155,041, entitled "Humanization of Rabbit Antibodies Using Universal Antibody Frameworks," filed on Jun. 25, 2008 and on Feb. 4, 2009, respectively.

Standard cloning and mutagenesis techniques well known to the person skilled in the art can be used to attach linkers, shuffle domains or construct fusions for the production of Fab fragments. Basic protocols disclosing the general methods of this invention are described in *Molecular Cloning, A Laboratory Manual* (Sambrook & Russell, $3^{rd}$ ed. 2001) and in *Current Protocols in Molecular Biology* (Ausubel et al., 1999).

The DNA sequence harboring a gene encoding a scFv polypeptide, or in the case of Fab fragments, encoding either two separate genes or a bi-cistronic operon comprising the two genes for the VL-Cκ and the VH-CH1 fusions are cloned in a suitable expression vector, preferably one with an inducible promoter. Care must be taken that in front of each gene an appropriate ribosome binding site is present that ensures translation. It is to be understood that the antibodies of the present invention comprise the disclosed sequences rather than they consist of them. For example, cloning strategies may require that a construct is made from which an antibody with one or a few additional residues at the N-terminal end are present. Specifically, the methionine derived from the start codon may be present in the final protein in cases where it has not been cleaved posttranslationally. Most of the constructs for scFv antibodies give rise to an additional alanine at the N-terminal end. In a preferred embodiment of the present invention, an expression vector for periplasmic expression in *E. coli* is chosen (Krebber, 1997). Said vector comprises a promoter in front of a cleavable signal sequence. The coding sequence for the antibody peptide is then fused in frame to the cleavable signal sequence. This allows the targeting of the expressed polypeptide to the bacterial periplasm where the signal sequence is cleaved. The antibody is then folded. In the case of the Fab fragments, both the VL-Cκ and the VH-CH1 fusions peptides must be linked to an export signal. The covalent S-S bond is formed at the C-terminal cysteines after the peptides have reached the periplasm. If cytoplasmic expression of antibodies is preferred, said antibodies usually can be obtained at high yields from inclusion bodies, which can be easily separated from other cellular fragments and protein. In this case the inclusion bodies are solubilized in a denaturing agent such as e.g. guaridine hydrochloride (GndHCl) and then refolded by renaturation procedures well known to those skilled in the art.

Plasmids expressing the scFv or Fab polypeptides are introduced into a suitable host, preferably a bacterial, yeast or mammalian cell, most preferably a suitable *E. coli* strain as for example JM83 for periplasmic expression or BL21 for expression in inclusion bodies. The polypeptide can be harvested either from the periplasm or form inclusion bodies and purified using standard techniques such as ion exchange chromatography, reversed phase chromatography, affinity chromatography and/or gel filtration known to the person skilled in the art.

The antibodies or antibody derivatives of the present invention can be characterized with respect to yield, solubility and stability in vitro. Binding capacities towards TNF, preferably towards human TNFα, can be tested in vitro by ELISA or surface plasmon resonance (BIACore), using recombinant human TNF as described in WO9729131, the latter method also allowing to determine the $k_{off}$ rate constant, which should preferably be less than $10^{-3}$ $s^{-1}$. $K_d$ values of ≤10 nM are preferred.

Aside from antibodies with strong binding affinity for human TNF, it is also desirable to generate anti-TNF antibodies which have beneficial properties from a therapeutic perspective. For example, the antibody may be one which shows neutralizing activity in a L929 TNFalpha-mediated cytotoxicity assay. In this assay toxicity of mouse L929 fibroblast cells treated with Actinomycin was induced with recombinant human TNF (hTNF). 90% of maximal hTNF-induced cytotoxicity was determined to be at a TNF concentration of 1000 pg/ml.

All L929 cells were cultured in RPMI 1640 with phenolred, with L-Glutamine medium supplemented with fetal calf serum (10% v/v). The neutralizing activity of anti-TNFa binders was assessed in RPMI 1640 without phenolred and 5% fetal calf serum. Different concentrations (0-374 ng/mL) of anti-TNF binders are added to L929 cells in presence of 1000 pg/ml hTNF in order to determine the concentration at which the antagonistic effect reaches half-maximal inhibition (EC50%) The dose response curve was fitted with nonlinear sigmoidal regression with variable slope and the EC50 was calculated.

Optimized Variants

The antibodies of the invention may be further optimized for enhanced functional properties, e.g., for enhanced solubility and/or stability.

In certain embodiments, the antibodies of the invention are optimized according to the "functional consensus" methodology disclosed in PCT Application Serial No. PCT/EP2008/001958, entitled "Sequence Based Engineering and Optimization of Single Chain Antibodies", filed on Mar. 12, 2008, which is incorporated herein by reference.

For example, the TNFα immunobinders of the invention can be compared with a database of functionally-selected scFvs to identify amino acid residue positions that are either more or less tolerant of variability than the corresponding position(s) in the VEGF immunobinder, thereby indicating that such identified residue position(s) may be suitable for engineering to improve functionality such as stability and/or solubility.

Exemplary framework positions for substitution are described in PCT Application No. PCT/CH2008/000285, entitled "Methods of Modifying Antibodies, and Modified Antibodies with Improved Functional Properties", filed on Jun. 25, 2008, and PCT Application No. PCT/CH2008/000284, entitled "Sequence Based Engineering and Optimization of Single Chain Antibodies", filed on Jun. 25, 2008. For example, one or more of the following substitutions may be introduced at an amino acid position (AHo numbering is referenced for each of the amino acid position listed below) in the heavy chain variable region of an immunobinder of the invention:

(a) Q or E at amino acid position 1;
 (b) Q or E at amino acid position 6;
 (c) T, S or A at amino acid position 7, more preferably T or A, even more preferably T;

(d) A, T, P, V or D, more preferably T, P, V or D, at amino acid position 10,
(e) L or V, more preferably L, at amino acid position 12,
(f) V, R, Q, M or K, more preferably V, R, Q or M at amino acid position 13;
(g) R, M, E, Q or K, more preferably R, M, E or Q, even more preferably R or E, at amino acid position 14;
(h) L or V, more preferably L, at amino acid position 19;
(i) R, T, K or N, more preferably R, T or N, even more preferably N, at amino acid position 20;
(j) I, F, L or V, more preferably I, F or L, even more preferably I or L, at amino acid position 21;
(k) R or K, more preferably K, at amino acid position 45;
(l) T, P, V, A or R, more preferably T, P, V or R, even more preferably R, at amino acid position 47;
(m) K, Q, H or E, more preferably K, H or E, even more preferably K, at amino acid position 50;
(n) M or I, more preferably I, at amino acid position 55;
(o) K or R, more preferably K, at amino acid position 77;
(p) A, V, L or I, more preferably A, L or I, even more preferably A, at amino acid position 78;
(q) E, R, T or A, more preferably E, T or A, even more preferably E, at amino acid position 82;
(r) T, S, I or L, more preferably T, S or L, even more preferably T, at amino acid position 86;
(s) D, S, N or G, more preferably D, N or G, even more preferably N, at amino acid position 87;
(t) A, V, L or F, more preferably A, V or F, even more preferably V, at amino acid position 89;
(u) F, S, H, D or Y, more preferably F, S, H or D, at amino acid position 90;
(v) D, Q or E, more preferably D or Q, even more preferably D, at amino acid position 92;
(w) G, N, T or S, more preferably G, N or T, even more preferably G, at amino acid position 95;
(x) T, A, P, F or S, more preferably T, A, P or F, even more preferably F, at amino acid position 98;
(y) R, Q, V, I, M, F, or L, more preferably R, Q, I, M, F or L, even more preferably Y, even more preferably L, at amino acid position 103; and
(z) N, S or A, more preferably N or S, even more preferably N, at amino acid position 107.

Additionally or alternatively, one or more of the following substitutions can be introduced into the light chain variable region of an immunobinder of the invention:
(aa) Q, D, L, E, S, or I, more preferably L, E, S or I, even more preferably L or E, at amino acid position 1;
(bb) S, A, Y, I, P or T, more preferably A, Y, I, P or T, even more preferably P or T at amino acid position 2;
(cc) Q, V, T or I, more preferably V, T or I, even more preferably V or T, at amino acid position 3;
(dd) V, L, I or M, more preferably V or L, at amino acid position 4;
(ee) S, E or P, more preferably S or E, even more preferably S, at amino acid position 7;
(ff) T or I, more preferably I, at amino acid position 10;
(gg) A or V, more preferably A, at amino acid position 11;
(hh) S or Y, more preferably Y, at amino acid position 12;
(ii) T, S or A, more preferably T or S, even more preferably T, at amino acid position 14;
(jj) S or R, more preferably S, at amino acid position 18;
(kk) T or R, more preferably R, at amino acid position 20;
(ll) R or Q, more preferably Q, at amino acid position 24;
(mm) H or Q, more preferably H, at amino acid position 46;
(nn) K, R or I, more preferably R or I, even more preferably R, at amino acid position 47;
(oo) R, Q, K, E, T, or M, more preferably Q, K, E, T or M, at amino acid position 50;
(pp) K, T, S, N, Q or P, more preferably T, S, N, Q or P, at amino acid position 53;
(qq) I or M, more preferably M, at amino acid position 56;
(rr) H, S, F or Y, more preferably H, S or F, at amino acid position 57;
(ss) I, V or T, more preferably V or T, R, even more preferably T, at amino acid position 74;
(tt) R, Q or K, more preferably R or Q, even more preferably R, at amino acid position 82;
(uu) L or F, more preferably F, at amino acid position 91;
(vv) G, D, T or A, more preferably G, D or T, even more preferably T, at amino acid position 92;
(xx) S or N, more preferably N, at amino acid position 94;
(yy) F, Y or S, more preferably Y or S, even more preferably S, at amino acid position 101; and
(zz) D, F, H, E, L, A, T, V, S, G or I, more preferably H, E, L, A, T, V, S, G or I, even more preferably A or V, at amino acid position 103.

In other embodiments, the immunobinders of the invention comprise one or more of the solubility and/or stability enhancing mutations described in U.S. Provisional Application Ser. No. 61/075,692, entitled "Solubility Optimization of Immunobinders," filed on Jun. 25, 2008. In certain preferred embodiments, the immunobinder comprises a solubility enhancing mutation at an amino acid position selected from the group of heavy chain amino acid positions consisting of 12, 103 and 144 (AHo Numbering convention). In one preferred embodiment, the immunobinder comprises one or more substitutions selected from the group consisting of: (a) Serine (S) at heavy chain amino acid position 12; (b) Serine (S) or Threonine (T) at heavy chain amino acid position 103; and (c) Serine (S) or Threonine (T) at heavy chain amino acid position 144. In another embodiment, the immunobinder comprises the following substitutions: (a) Serine (S) at heavy chain amino acid position 12; (b) Serine (S) or Threonine (T) at heavy chain amino acid position 103; and (c) Serine (S) or Threonine (T) at heavy chain amino acid position 144.

As mentioned above, combinations of the VL and VH sequences, in particular of those having the same or essentially the same set of CDR sequences but different framework sequences e.g. due to the presence of the substitutions mentioned above, can be shuffled and combined by a linker sequence. Exemplary combinations, without being limited to, include:

EP43 min
SEQ ID NO: 94
EIVMTQSPSTLSASVGDRVIITCQASQSISDWLAWYQQKPGKAPKLLIYG

ASRLASGVPSRFSGSGSGAEFTLTISSLQPDDFATYYCQQGWSDSYVDNL

FGQGTKLTVLGGGGSGGGGSGGGGSGGGGSEVQLVESGGGLVQPGGSLR

LSCAASGFSLSSGAMSWVRQAPGKGLEWVSVIISSGATYYASWAKGRFTI

SRDNSKNTLYLQMNSLRAEDTAVYYCAKGGPDDSNSMGTFDPWGQGTLVT

VSS

EP43max
SEQ ID NO: 95
EIVMTQSPSTLSASVGDRVIIKCQASQSISDWLAWYQQKPGKAPKLLIYG

ASRLASGFPSRFSGSGSGAEFTLTISGLEPADFATYYCQQGWSDSYVDNL

FGQGTKLTVLGGGGSGGGGSGGGGSGGGGSEVQLVESGGGLVQPGGSLR

LSCTVSGFSLSSGAMSWVRQAPGKGLEWVGVIISSGATYYASWAKGRFTI
SKDTSKNTVYLQMNSLRAEDTAVYYCARGGPDDSNSMGTFDPWGQGTLVT
VSS

EP43minmax
SEQ ID NO: 96
EIVMTQSPSTLSASVGDRVIITCQASQSISDWLAWYQQKPGKAPKLLIYG
ASRLASGVPSRFSGSGSGAEFTLTISSLQPDDFATYYCQQGWSDSYVDNL
FGQGTKLTVLGGGGSGGGGSGGGGSGGGGSEVQLVESGGGLVQPGGSLR
LSCTVSGFSLSSGAMSWVRQAPGKGLEWVGVIISSGATYYASWAKGRFTI
SKDTSKNTVYLQMNSLRAEDTAVYYCARGGPDDSNSMGTFDPWGQGTLVT
VSS EP43max DHP
SEQ ID NO: 97
EIVMTQSPSTLSASVGDRVIIKCQASQSISDWLAWYQQKPGKAPKLLIYG
ASRLASGFPSRFSGSGSGAEFTLTISGLEPADFATYYCQQGWSDSYVDNL
FGQGTKLTVLGGGGSGGGGSGGGGSGGGGSEVQLVESGGGSVQPGGSLR
LSCTVSGFSLSSGAMSWVRQAPGKGLEWVGVIISSGATYYASWAKGRFTI
SKDTSKNTVYLQMNSLRAEDTATYYCARGGPDDSNSMGTFDPWGQGTSVT
VSS EP43minmaxDHP
SEQ ID NO: 98
EIVMTQSPSTLSASVGDRVIITCQASQSISDWLAWYQQKPGKAPKLLIYG
ASRLASGVPSRFSGSGSGAEFTLTISSLQPDDFATYYCQQGWSDSYVDNL
FGQGTKLTVLGGGGSGGGGSGGGGSGGGGSEVQLVESGGGSVQPGGSLR
LSCTVSGFSLSSGAMSWVRQAPGKGLEWVGVIISSGATYYASWAKGRFTI
SKDTSKNTVYLQMNSLRAEDTATYYCARGGPDDSNSMGTFDPWGQGTSVT
VSS EP43minmax VL: T22K
SEQ ID NO: 99
EIVIVITQSPSTLSASVGDRVIIKCQASQSISDWLAWYQQKPGKAPKLLI
YGASRLASGVPSRFSGSGSGAEFTLTISSLQPDDFATYYCQQGWSDSYVD
NLFGQGTKLTVLGGGGSGGGGSGGGGSGGGGSEVQLVESGGGLVQPGGS
LRLSCTVSGFSLSSGAMSWVRQAPGKGLEWVGVIISSGATYYASWAKGRF
TISKDTSKNTVYLQMNSLRAEDTAVYYCARGGPDDSNSMGTFDPWGQGTL
VTVSS EP43minmax: VL: V58F
SEQ ID NO: 100
EIVMTQSPSTLSASVGDRVIITCQASQSISDWLAWYQQKPGKAPKLLIYG
ASRLASGFPSRFSGSGSGAEFTLTISSLQPDDFATYYCQQGWSDSYVDNL
FGQGTKLTVLGGGGSGGGGSGGGGSGGGGSEVQLVESGGGLVQPGGSLR
LSCTVSGFSLSSGAMSWVRQAPGKGLEWVGVIISSGATYYASWAKGRFTI
SKDTSKNTVYLQMNSLRAEDTAVYYCARGGPDDSNSMGTFDPWGQGTLVT
VSS EP43minmax VL: D81A
SEQ ID NO: 101
EIVMTQSPSTLSASVGDRVIITCQASQSISDWLAWYQQKPGKAPKLLIYG
ASRLASGVPSRFSGSGSGAEFTLTISSLQPADFATYYCQQGWSDSYVDNL
FGQGTKLTVLGGGGSGGGGSGGGGSGGGGSEVQLVESGGGLVQPGGSLR
LSCTVSGFSLSSGAMSWVRQAPGKGLEWVGVIISSGATYYASWAKGRFTI
SKDTSKNTVYLQMNSLRAEDTAVYYCARGGPDDSNSMGTFDPWGQGTLVT
VSS EP43minmax VL: Q79E
SEQ ID NO: 102
EIVMTQSPSTLSASVGDRVIITCQASQSISDWLAWYQQKPGKAPKLLIYG
ASRLASGVPSRFSGSGSGAEFTLTISSLEPDDFATYYCQQGWSDSYVDNL
FGQGTKLTVLGGGGSGGGGSGGGGSGGGGSEVQLVESGGGLVQPGGSLR
LSCTVSGFSLSSGAMSWVRQAPGKGLEWVGVIISSGATYYASWAKGRFTI
SKDTSKNTVYLQMNSLRAEDTAVYYCARGGPDDSNSMGTFDPWGQGTLVT
VSS EP1min
SEQ ID NO: 103
EIVIVITQSPSTLSASVGDRVIITCQSTESVYKNNYLAWYQQKPGKAPKL
LIYDASTLASGVPSRFSGSGSGAEFTLTISSLQPDDFATYYCAGYYRSGS
GTANGSFGQGTKLTVLGGGGSGGGGSGGGGSGGGGSEVQLVESGGGLVQ
PGGSLRLSCAASGFTFSNDAISWVRQAPGKGLEWVSYISDWSIRYYANWA
QGRFTISRDNSKNTLYLQMNSLRAEDTAVYYCAKGAPGAGDNGIWGQGTL
VTVSS EP1max
SEQ ID NO: 104
EIVIVITQSPSTLSASVGDRVIITCQSTESVYKNNYLAWYQQKPGKAPKL
LIYDASTLASGVPSRFSGSGSGTEFTLTISSLQPDDFATYYCAGYYRSGS
GTANGSFGQGTKLTVLGGGGSGGGGSGGGGSGGGGSEVQLVESGGGSVQ
PGGSLRLSCTVSGIDLSNDAISWVRQAPGKGLEWVAYISDWSIRYYANWA
QGRFTISKDTSKNTVYLQMNSLRAEDTATYYCARGAPGAGDNGIWGQGTT
VTVSS EP1minmax
SEQ ID NO: 105
EIVIVITQSPSTLSASVGDRVIITCQSTESVYKNNYLAWYQQKPGKAPKL
LIYDASTLASGVPSRFSGSGSGAEFTLTISSLQPDDFATYYCAGYYRSGS
GTANGSFGQGTKLTVLGGGGSGGGGSGGGGSGGGGSEVQLVESGGGSVQ
PGGSLRLSCTVSGIDLSNDAISWVRQAPGKGLEWVAYISDWSIRYYANWA
QGRFTISKDTSKNTVYLQMNSLRAEDTATYYCARGAPGAGDNGIWGQGTT
VTVSS EP6min
SEQ ID NO: 106
EIVMTQSPSTLSASVGDRVIITCQASESIYSGLAWYQQKPGKAPKLLIYQ
ASTLASGVPSRFSGSGSGAEFTLTISSLQPDDFATYYCQQGFGTSNVENP
FGQGTKLTVLGGGGSGGGGSGGGGSGGGGSEVQLVESGGGLVQPGGSLR
LSCAASGFSLSRYGVSWVRQAPGKGLEWVSTIGEAGRAYYANWARSRFTI -continued
SRDNSKNTLYLQMNSLRAEDTAVYYCAKGEVFNNGWGAFNIWGQGTLVTV
SS EP6max
SEQ ID NO: 107
EIVMTQSPSTLSASVGDRVIITCQASESIYSGLAWYQQKPGKAPKLLIYQ
ASTLASGVPSRFSGSGSGTDFTLAISSLQPDDFATYYCQQGFGTSNVENP
FGQGTKLTVLGGGGSGGGGSGGGGSGGGGS
EVQLVESGGGLVQPGGSLRLSCTVSGFSLSRYGVSWVRQAPGKGLEWVGT
IGEAGRAYYANWARSRSTISRDTSKNTVYLQMNSLRAEDTAVYYCARGEV
FNNGWGAFNIWGQGTLVTVSS EP6minmax
SEQ ID NO: 108
EIVMTQSPSTLSASVGDRVIITCQASESIYSGLAWYQQKPGKAPKLLIYQ
ASTLASGVPSRFSGSGSGAEFTLTISSLQPDDFATYYCQQGFGTSNVENP
FGQGTKLTVLGGGGSGGGGSGGGGSGGGGSEVQLVESGGGLVQPGGSLR
LSCTVSGFSLSRYGVSWVRQAPGKGLEWVGTIGEAGRAYYANWARSRSTI
SRDTSKNTVYLQMNSLRAEDTAVYYCARGEVFNNGWGAFNIWGQGTLVTV
SS EP15min
SEQ ID NO: 109
EIVMTQSPSTLSASVGDRVIITCQASENIYTSLAWYQQKPGKAPKLLIYS
ASTLASGVPSRFSGSGSGAEFTLTISSLQPDDFATYYCQQGFATSNVENP
FGQGTKLTVLGGGGSGGGGSGGGGSGGGGSEVQLVESGGGLVQPGGSLR
LSCAASGFTFSRYGVSWVRQAPGKGLEWVSAIGETGRAYYANWAKSRFTI
SRDNSKNTLYLQMNSLRAEDTAVYYCAKGEEFNNGWGAFNIWGQGTLVTV
SS EP15max
SEQ ID NO: 110
EIVMTQSPSTLSASVGDRVIITCQASENIYTSLAWYQQKPGKAPKLLIYS
ASTLASGVPSRFSGSGSGTEFTLTISSLQPDDFATYYCQQGFATSNVENP
FGQGTKLTVLGGGGSGGGGSGGGGSGGGGSEVQLVESGGGSVQPGGSLR
LSCTVSGFSLSRYGVSWVRQAPGKGLEWVGAIGETGRAYYANWAKSRSTI
SRDTSKNTVYLQMNSLRAEDTATYYCARGEEFNNGWGAFNIWGQGTTVTV
SS EP15minmax
SEQ ID NO: 111
EIVMTQSPSTLSASVGDRVIITCQASENIYTSLAWYQQKPGKAPKLLIYS
ASTLASGVPSRFSGSGSGAEFTLTISSLQPDDFATYYCQQGFATSNVENP
FGQGTKLTVLGGGGSGGGGSGGGGSGGGGSEVQLVESGGGSVQPGGSLR
LSCTVSGFSLSRYGVSWVRQAPGKGLEWVGAIGETGRAYYANWAKSRSTI
SRDTSKNTVYLQMNSLRAEDTATYYCARGEEFNNGWGAFNIWGQGTTVTV
SS EP19minmod
SEQ ID NO: 112
EIVMTQSPSTLSASVGDRVIITCQASDNIYRGLAWYQQKPGKAPKLLIYD
ASTLQSGVPSRFSGSGSGAEFTLTISSLQPDDFATYYCLGVYGYSSDDGA
AFGQGTKLTVLGGGGSGGGGSGGGGSGGGGSEVQLVESGGGLVQPGGSL
RLSCAASGFSLNSNEISWVRQAPGKGLEWVSYIGNGGMTHYASWAKGRFT
ISRDNSKNTLYLQMNSLRAEDTAVYYCAKSVEYTDLYYLNIWGQGTLVTV
SS EP19maxmod
SEQ ID NO: 113
EIVMTQSPSTLSASVGDRVIITCQASDNIYRGLAWYQQKPGKAPKLLIYD
ASTLQSGVPSRFSGSGGTQFTLTISSLQPDDFATYYCLGVYGYSSDDGAA
FGQGTKLTVLGGGGSGGGGSGGGGSGGGGSEVQLVESGGGLVQPGGSLR
LSCTVSGFSLNSNEISWVRQAPGKGLEWVGYIGNGGMTHYASWAKGRFTI
SRDTSKNTVYLQMNSLRAEDTAVYYCASSVEYTDLYYLNIWGQGTLVTVS
S EP34min
SEQ ID NO: 114
EIVMTQSPSTLSASVGDRVIITCQSSQSVYGNIWMAWYQQKPGKAPKLLI
YQASKLASGVPSRFSGSGSGAEFTLTISSLQPDDFATYYCQGNFNTGDRY
AFGQGTKLTVLGGGGSGGGGSGGGGSGGGGSEVQLVESGGGLVQPGGSL
RLSCAASGFTISRSYWICWVRQAPGKGLEWVSCIYGDNDITPLYANWAKG
RFTISRDNSKNTLYLQMNSLRAEDTAVYYCAKLGYADYAYDLWGQGTLVT
VSS EP34max
SEQ ID NO: 115
EIVMTQSPSTLSASLGDRVIITCQSSQSVYGNIWMAWYQQKSGKAPKLLI
YQASKLASGVPSRFSGSGSGAEFSLTISSLQPDDFATYYCQGNFNTGDRY
AFGQGTKLTVLGGGGSGGGGSGGGGSGGGGSEVQLVESGGGLVQPGGSL
RLSCTASGFTISRSYWICWVRQAPGKGLEWVACIYGDNDITPLYANWAKG
RFPVSTDTSKNTVYLQMNSLRAEDTAVYYCARLGYADYAYDLWGQGTLVT
VSS EP35min
SEQ ID NO: 116
EIVIVITQSPSTLSASVGDRVIITCQASQSISNLLAWYQQKPGKAPKLLI
YAASKLASGVPSRFSGSGSGAEFTLTISSLQPDDFATYYCQQGWSHTNVD
NTFGQGTKLTVLGGGGSGGGGSGGGGSGGGGSEVQLVESGGGLVQPGGS
LRLSCAASGFTFSVGYWICWVRQAPGKGLEWVSCIDAGTSGGTYYATWAK
GRFTISRDNSKNTLYLQMNSLRAEDTAVYYCAKGVSSNGYYFKLWGQGTL
VTVSS EP35max
SEQ ID NO: 117
EIVIVITQSPSTLSASVGDRVIITCQASQSISNLLAWYQQKPGKAPKLLI
VAASKLASGVPSRFSGSGSGTEFTLTISSLQPDDFATYYCQQGWSHTNVD
NTFGQGTKLTVLGGGGSGGGGSGGGGSGGGGSEVQLVESGGGSVQPGGS
LRLSCTASGFSFSVGYWICWVRQAPGKGLEWVACIDAGTSGGTYYATWAK
GRFTISKDTSKNTVYLQMNSLRAEDTATYYCARGVSSNGYYFKLWGQGTT
VTVSS -continued EP35minmax
SEQ ID NO: 118
EIVIVITQSPSTLSASVGDRVIITCQASQSISNLLAWYQQKPGKAPKLLI
YAASKLASGVPSRFSGSGSGAEFTLTISSLQPDDFATYYCQQGWSHTNVD
NTFGQGTKLTVLGGGGSGGGGSGGGGSGGGGSEVQLVESGGGSVQPGGS
LRLSCTASGFSFSVGYWICWVRQAPGKGLEWVACIDAGTSGGTYYATWAK
GRFTISKDTSKNTVYLQMNSLRAEDTATYYCARGVSSNGYYFKLWGQGTT
VTVSS EP42min
SEQ ID NO: 119
EIVIVITQSPSTLSASVGDRVIITCQSTESVYKNNYLAWYQQKPGKAPKL
LIYDASTLASGVPSRFSGSGSGAEFTLTISSLQPDDFATYYCAGYYRSGF
GTANGSFGQGTKLTVLGGGGSGGGGSGGGGSGGGGSEVQLVESGGGLVQ
PGGSLRLSCAASGFTFRNDAISWVRQAPGKGLEWVSYISDWGIKYYASWV
KGRFTISRDNSKNTLYLQMNSLRAEDTAVYYCAKGAPGAGDNGIWGQGTL
VTVSS EP42max
SEQ ID NO: 120
EIVIVITQSPSTLSASVGDRVIITCQSTESVYKNNYLAWYQQKPGKAPKL
LIYDASTLASGVPSRFSGSGSGTEFTLTISSLQPDDFATYYCAGYYRSGF
GTANGSFGQGTKLTVLGGGGSGGGGSGGGGSGGGGSEVQLVESGGGSVQ
PGGSLRLSCTVSGIDLRNDAISWVRQAPGKGLEWVSYISDWGIKYYASWV
KGRFTISKDTSKNTVYLQMNSLRAEDTATYYCARGAPGAGDNGIWGQGTT
VTVSS EP42minmax
SEQ ID NO: 121
EIVMTQSPSTLSASVGDRVIITCQSTESVYKNNYLAWYQQKPGKAPKLLI
YDASTLASGVPSRFSGSGSGAEFTLTISSLQPDDFATYYCAGYYRSGFGT
ANGSFGQGTKLTVLGGGGSGGGGSGGGGSGGGGSEVQLVESGGGSVQPG
GSLRLSCTVSGIDLRNDAISWVRQAPGKGLEWVSYISDWGIKYYASWVKG
RFTISKDTSKNTVYLQMNSLRAEDTATYYCARGAPGAGDNGIWGQGTTVT
VSS In a preferred embodiment, a sequence has at least 90% identity, more preferably at least 95% identity and most preferably 100% identity to anyone of sequences SEQ ID No. 94-121.

Uses of Anti-TNF Antibodies

For therapeutic applications, the anti-TNF antibodies of the invention are administered to a mammal, preferably a human, in a pharmaceutically acceptable dosage form such as those discussed above, including those that may be administered to a human intravenously as a bolus or by continuous infusion over a period of time, by intramuscular, intraperitoneal, intra-cerebrospinal, subcutaneous, intra-articular, intrasynovial, intrathecal, oral, topical, or inhalation routes. The antibodies also are suitably administered by intra tumoral, peritumoral, intralesional, or perilesional routes, to exert local as well as systemic therapeutic effects.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

The anti-TNF antibodies are useful in the treatment of TNF-mediated diseases. Depending on the type and severity of the disease, about 1 µg/kg to about 50 mg/kg (e.g., 0.1-20 mg/kg) of antibody is an initial candidate dosage for administration to the patient, whether, for example, by one or more separate administrations, or by continuous infusion. A typical daily or weekly dosage might range from about 1 µg/kg to about 20 mg/kg or more, depending on the factors mentioned above. For repeated administrations over several days or longer, depending on the condition, the treatment is repeated until a desired suppression of disease symptoms occurs. However, other dosage regimens may be useful. The progress of this therapy is easily monitored by conventional techniques and assays, including, for example, radiographic tumor imaging.

According to another embodiment of the invention, the effectiveness of the antibody in preventing or treating disease may be improved by administering the antibody serially or in combination with another agent that is effective for those purposes, such as vascular endothelial growth factor (VEGF), an antibody capable of inhibiting or neutralizing the angiogenic activity of acidic or basic fibroblast growth factor (FGF) or hepatocyte growth factor (HGF), an antibody capable of inhibiting or neutralizing the coagulant activities of tissue factor, protein C, or protein S (see Esmon et al., PCT Patent Publication No. WO 91/01753, published 21 Feb. 1991), an antibody capable of binding to HER2 receptor (see Hudziak et al., PCT Patent Publication No. WO 89/06692, published 27 Jul. 1989), or one or more conventional therapeutic agents such as, for example, alkylating agents, folic acid antagonists, anti-metabolites of nucleic acid metabolism, antibiotics, pyrimidine analogs, 5-fluorouracil, cisplatin, purine nucleosides, amines, amino acids, triazol nucleosides, or corticosteroids. Such other agents may be present in the composition being administered or may be administered separately. Also, the antibody is suitably administered serially or in combination with radiological treatments, whether involving irradiation or administration of radioactive substances.

The antibodies of the invention may be used as affinity purification agents. In this process, the antibodies are immobilized on a solid phase such a Sephadex resin or filter paper, using methods well known in the art. The immobilized antibody is contacted with a sample containing the TNF protein (or fragment thereof) to be purified, and thereafter the support is washed with a suitable solvent that will remove substantially all the material in the sample except the TNF protein, which is bound to the immobilized antibody. Finally, the support is washed with another suitable solvent, such as glycine buffer, pH 5.0, that will release the TNF protein from the antibody.

Anti-TNF antibodies may also be useful in diagnostic assays for TNF protein, e.g., detecting its expression in specific cells, tissues, or serum. Such diagnostic methods may be useful in cancer diagnosis.

For diagnostic applications, the antibody typically will be labeled with a detectable moiety. Numerous labels are available which can be generally grouped into the following categories:

(a) Radioisotopes, such as $^{111}$In, $^{99}$Tc, $^{14}$C, $^{131}$I, $^{125}$I, $^{3}$H, $^{32}$P or 35S. The antibody can be labeled with the radioisotope using the techniques described in Current Protocols in Immunology, Volumes 1 and 2, Coligen et al., Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981). Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) .beta.-D-galactosidase (.beta.-D-Gal) with a chromogenic substrate (e.g., P-nitrophenyl-.beta.-D-galactosidase) or fluorogenic substrate 4-methylumbelliferyl-.beta.-D-galactosidase.

Numerous other enzyme-substrate combinations are available to those skilled in the art. For a general review of these, see U.S. Pat. Nos. 4,275,149 and 4,318,980. Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-TNF antibody need not be labeled, and the presence thereof can be detected using a labeled antibody which binds to the TNF antibody.

The antibodies of the present invention may be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

Competitive binding assays rely on the ability of a labeled standard to compete with the test sample analyte for binding with a limited amount of antibody. The amount of TNF protein in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Generally, the antibody is labeled with a radio nuclide (such as .sup.$^{111}$In, .$^{99}$Tc, .$^{14}$C, .$^{131}$I, $^{125}$I, $^{3}$H, $^{32}$P or $^{35}$S) so that the tumor can be localized using immunoscintiography.

The antibody of the present invention can be provided in a kit, a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Pharmaceutical Preparations

In one aspect the invention provides pharmaceutical formulations comprising anti-TNF antibodies for the treatment of TNF-mediated diseases. The term "pharmaceutical formulation" refers to preparations which are in such form as to permit the biological activity of the antibody or antibody derivative to be unequivocally effective, and which contain no additional components which are toxic to the subjects to which the formulation would be administered. "Pharmaceutically acceptable" excipients (vehicles, additives) are those which can reasonably be administered to a subject mammal to provide an effective dose of the active ingredient employed.

A "stable" formulation is one in which the antibody or antibody derivative therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. Preferably, the formulation is stable at room temperature (about 30° C.) or at 40° C. for at least 1 month and/or stable at about 2-8° C. for at least 1 year for at least 2 years. Furthermore, the formulation is preferably stable following freezing (to, e.g., −70° C.) and thawing of the formulation.

An antibody or antibody derivative "retains its physical stability" in a pharmaceutical formulation if it shows no signs of aggregation, precipitation and/or denaturation upon visual examination of color and/or clarity, or as measured by UV light scattering or by size exclusion chromatography.

An antibody or antibody derivative "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography, for example.

An antibody or antibody derivative "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example. Other "biological activity" assays for antibodies are elaborated herein below.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

A "polyol" is a substance with multiple hydroxyl groups, and includes sugars (reducing and non-reducing sugars), sugar alcohols and sugar acids. Preferred polyols herein have a molecular weight which is less than about 600 kD (e.g. in the range from about 120 to about 400 kD). A "reducing sugar" is one which contains a hemiacetal group that can reduce metal ions or react covalently with lysine and other amino groups in proteins and a "non-reducing sugar" is one which does not have these properties of a reducing sugar. Examples of reducing sugars are fructose, mannose, maltose, lactose, arabinose, xylose, ribose, rhamnose, galactose and glucose. Non-reducing sugars include sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof. Where it is desired that the formulation is freeze-thaw stable, the polyol is preferably one which does not crystallize at freezing temperatures (e.g. −20° C.) such that it destabilizes the antibody in the formulation. Non-reducing sugars such as sucrose and trehalose are the preferred polyols herein, with trehalose being preferred over sucrose, because of the superior solution stability of trehalose.

As used herein, "buffer" refers to a buffered solution that resists changes in pH by the action of its acid-base conjugate components. The buffer of this invention has a pH in the range from about 4.5 to about 6.0; preferably from about 4.8 to about 5.5; and most preferably has a pH of about 5.0. Examples of buffers that will control the pH in this range include acetate (e.g. sodium acetate), succinate (such as sodium succinate), gluconate, histidine, citrate and other organic acid buffers. Where a freeze-thaw stable formulation is desired, the buffer is preferably not phosphate.

In a pharmacological sense, in the context of the present invention, a "therapeutically effective amount" of an antibody or antibody derivative refers to an amount effective in the prevention or treatment of a disorder for the treatment of which the antibody or antibody derivative is effective. A "disease/disorder" is any condition that would benefit from treatment with the antibody or antibody derivative. This includes chronic and acute disorders or diseases including those pathological conditions which predispose the mammal to the disorder in question.

A "preservative" is a compound which can be included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkyl-benzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

The present invention also provides pharmaceutical compositions comprising one or more antibodies or antibody derivative compounds, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. As noted above, other active ingredients may (but need not) be included in the pharmaceutical compositions provided herein.

A carrier is a substance that may be associated with an antibody or antibody derivative prior to administration to a patient, often for the purpose of controlling stability or bioavailability of the compound. Carriers for use within such formulations are generally biocompatible, and may also be biodegradable. Carriers include, for example, monovalent or multivalent molecules such as serum albumin (e.g., human or bovine), egg albumin, peptides, polylysine and polysaccharides such as aminodextran and polyamidoamines. Carriers also include solid support materials such as beads and microparticles comprising, for example, polylactate polyglycolate, poly(lactide-co-glycolide), polyacrylate, latex, starch, cellulose or dextran. A carrier may bear the compounds in a variety of ways, including covalent bonding (either directly or via a linker group), noncovalent interaction or admixture.

Pharmaceutical compositions may be formulated for any appropriate manner of administration, including, for example, topical, oral, nasal, rectal or parenteral administration. In certain embodiments, compositions in a form suitable for oral use are preferred. Such forms include, for example, pills, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. The term parenteral as used herein includes subcutaneous, intradermal, intravascular (e.g., intravenous), intramuscular, spinal, intracranial, intrathecal and intraperitoneal injection, as well as any similar injection or infusion technique.

Compositions intended for oral use may be prepared according to any method known to the art for the manufacture of pharmaceutical compositions and may contain one or more agents, such as sweetening agents, flavoring agents, coloring agent, and preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil). Aqueous suspensions contain the antibody or antibody derivative in admixture with excipients suitable for the manufacture of aqueous suspensions. Such excipients include suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, for example ethyl or n-propyl p-hydroxybenzoate, one or more coloring agents, one or more flavoring agents, and one or more sweetening agents, such as sucrose or saccharin. Syrups and elixirs may be formulated with sweetening agents, such as glycerol, propylene glycol, sorbitol, or sucrose. Such formulations may also comprise one or more demulcents, preservatives, flavoring agents, and/or coloring agents.

Oily suspensions may be formulated by suspending the active ingredients in a vegetable oil (e.g., arachis oil, olive oil, sesame oil, or coconut oil) or in a mineral oil such as liquid paraffin. The oily suspensions may contain a thickening agent such as beeswax, hard paraffin, or cetyl alcohol. Sweetening agents, such as those set forth above, and/or flavoring agents may be added to provide palatable oral preparations. Such suspensions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions may also be in the form of oil-in-water emulsions. The oily phase may be a vegetable oil (e.g., olive oil or arachis oil), a mineral oil (e.g., liquid paraffin), or a mixture thereof. Suitable emulsifying agents include naturally-occurring gums (e.g., gum acacia or gum tragacanth), naturally-occurring phosphatides (e.g., soy bean, lecithin, and esters or partial esters derived from fatty acids and hexitol), anhydrides (e.g., sorbitan monoleate), and condensation products of partial esters derived from fatty acids and hexitol with ethylene oxide (e.g., polyoxyethylene sorbitan monoleate). An emulsion may also comprise one or more sweetening and/or flavoring agents.

The pharmaceutical composition may be prepared as a sterile injectable aqueous or oleaginous suspension in which the modulator, depending on the vehicle and concentration used, is either suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid may be used in the preparation of injectable compositions, and adjuvants such as local anesthetics, preservatives and/or buffering agents can be dissolved in the vehicle.

Pharmaceutical compositions may be formulated as sustained release formulations (i.e., a formulation such as a capsule that effects a slow release of modulator following administration). Such formulations may generally be prepared using well known technology and administered by, for example, oral, rectal, or subcutaneous implantation, or by implantation at the desired target site. Carriers for use within such formulations are biocompatible, and may also be biodegradable; preferably the formulation provides a relatively constant level of modulator release. The amount of an antibody or antibody derivative contained within a sustained release formulation depends upon, for example, the site of implantation, the rate and expected duration of release and the nature of the disease/disorder to be treated or prevented.

Antibody or antibody derivatives provided herein are generally administered in an amount that achieves a concentration in a body fluid (e.g., blood, plasma, serum, CSF, synovial fluid, lymph, cellular interstitial fluid, tears or urine) that is sufficient to detectably bind to TNF and prevent or inhibit TNF-mediated diseases/disorders. A dose is considered to be effective if it results in a discernible patient benefit as described herein. Preferred systemic doses range from about 0.1 mg to about 140 mg per kilogram of body weight per day (about 0.5 mg to about 7 g per patient per day), with oral doses generally being about 5-20 fold higher than intravenous doses. The amount of antibody or antibody derivative that may be combined with the carrier materials to produce a single dosage form will vary depending upon the host treated and the particular mode of administration. Dosage unit forms will generally contain between from about 1 mg to about 500 mg of an active ingredient.

Pharmaceutical compositions may be packaged for treating conditions responsive to an antibody or antibody derivative directed to TNF. Packaged pharmaceutical compositions may include a container holding a effective amount of at least one antibody or antibody derivative as described herein and instructions (e.g., labeling) indicating that the contained composition is to be used for treating a disease/disorder responsive to one antibody or antibody derivative following administration in the patient.

The antibodies or antibody derivatives of the present invention can also be chemically modified. Preferred modifying groups are polymers, for example an optionally substituted straight or branched chain polyalkene, polyalkenylene, or polyoxyalkylene polymer or a branched or unbranched polysaccharide. Such effector group may increase the half-live of the antibody in vivo. Particular examples of synthetic polymers include optionally substituted straight or branched chain poly(ethyleneglycol) (PEG), poly(propyleneglycol), poly(vinylalcohol) or derivatives thereof. Particular naturally occurring polymers include lactose, amylose, dextran, glycogen or derivatives thereof. The size of the polymer may be varied as desired, but will generally be in an average molecular weight range from 500 Da to 50000 Da. For local application where the antibody is designed to penetrate tissue, a preferred molecular weight of the polymer is around 5000 Da. The polymer molecule can be attached to the antibody, in particular to the C-terminal end of the Fab fragment heavy chain via a covalently linked hinge peptide as described in WO0194585. Regarding the attachment of PEG moieties, reference is made to "Poly (ethyleneglycol) Chemistry, Biotechnological and Biomedical Applications", 1992, J. Milton Harris (ed), Plenum Press, New York and "Bioconjugation Protein Coupling Techniques for the Biomedical Sciences", 1998, M. Aslam and A. Dent, Grove Publishers, New York.

After preparation of the antibody or antibody derivative of interest as described above, the pharmaceutical formulation comprising it is prepared. The antibody to be formulated has not been subjected to prior lyophilization and the formulation of interest herein is an aqueous formulation. Preferably the antibody or antibody derivative in the formulation is an antibody fragment, such as an scFv. The therapeutically effective amount of antibody present in the formulation is determined by taking into account the desired dose volumes and mode(s) of administration, for example. From about 0.1 mg/ml to about 50 mg/ml, preferably from about 0.5 mg/ml to about 25 mg/ml and most preferably from about 2 mg/ml to about 10 mg/ml is an exemplary antibody concentration in the formulation.

An aqueous formulation is prepared comprising the antibody or antibody derivative in a pH-buffered solution The buffer of this invention has a pH in the range from about 4.5 to about 6.0, preferably from about 4.8 to about 5.5, and most preferably has a pH of about 5.0. Examples of buffers that will control the pH within this range include acetate (e.g. sodium acetate), succinate (such as sodium succinate), gluconate, histidine, citrate and other organic acid buffers. The buffer concentration can be from about 1 mM to about 50 mM, preferably from about 5 mM to about 30 mM, depending, for example, on the buffer and the desired isotonicity of the formulation. The preferred buffer is sodium acetate (about 10 mM), pH 5.0.

A polyol, which acts as a tonicifier and may stabilize the antibody, is included in the formulation. In preferred embodiments, the formulation does not contain a tonicifying amount of a salt such as sodium chloride, as this may cause the antibody or antibody derivative to precipitate and/or may result in oxidation at low pH. In preferred embodiments, the polyol is a non-reducing sugar, such as sucrose or trehalose. The polyol is added to the formulation in an amount which may vary with respect to the desired isotonicity of the formulation. Preferably the aqueous formulation is isotonic, in which case suitable concentrations of the polyol in the formulation are in the range from about 1% to about 15% w/v, preferably in the range from about 2% to about 10% w/v, for example. However, hypertonic or hypotonic formulations may also be suitable. The amount of polyol added may also alter with respect to the molecular weight of the polyol. For example, a lower amount of a monosaccharide (e.g. mannitol) may be added, compared to a disaccharide (such as trehalose).

A surfactant is also added to the antibody or antibody derivative formulation. Exemplary surfactants include nonionic surfactants such as polysorbates (e.g. polysorbates 20, 80 etc) or poloxamers (e.g. poloxamer 188). The amount of surfactant added is such that it reduces aggregation of the formulated antibody/antibody derivative and/or minimizes the formation of particulates in the formulation and/or reduces adsorption. For example, the surfactant may be present in the formulation in an amount from about 0.001% to about 0.5%, preferably from about 0.005% to about 0.2% and most preferably from about 0.01% to about 0.1%.

In one embodiment, the formulation contains the above-identified agents (i.e. antibody or antibody derivative, buffer, polyol and surfactant) and is essentially free of one or more preservatives, such as benzyl alcohol, phenol, m-cresol, chlorobutanol and benzethonium Cl. In another embodiment, a preservative may be included in the formulation, particularly where the formulation is a multidose formulation. The concentration of preservative may be in the range from about 0.1% to about 2%, most preferably from about 0.5% to about 1%. One or more other pharmaceutically acceptable carriers, excipients or stabilizers such as those described in Remington's Pharmaceutical Sciences 21st edition, Osol, A. Ed. (2006) may be included in the formulation provided that they do not adversely affect the desired characteristics of the formulation. Acceptable carriers, excipients or stabilizers are non-toxic to recipients at the dosages and concentrations employed and include; additional buffering agents; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The formulations to be used for in vivo administration must be sterile. This is readily accomplished by filtration through sterile filtration membranes, prior to, or following, preparation of the formulation.

The formulation is administered to a mammal in need of treatment with the antibody, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In preferred embodiments, the formulation is administered to the mammal by intravenous administration. For such purposes, the formulation may be injected using a syringe or via an IV line, for example.

The appropriate dosage ("therapeutically effective amount") of the antibody will depend, for example, on the condition to be treated, the severity and course of the condition, whether the antibody is administered for preventive or therapeutic purposes, previous therapy, the patient's clinical history and response to the antibody, the type of antibody used, and the discretion of the attending physician. The antibody or antibody derivative is suitably administered to the patent at one time or over a series of treatments and may be administered to the patent at any time from diagnosis onwards. The antibody or antibody derivative may be administered as the sole treatment or in conjunction with other drugs or therapies useful in treating the condition in question.

As a general proposition, the therapeutically effective amount of the antibody or antibody derivative administered will be in the range of about 0.1 to about 50 mg/kg of patent body weight whether by one or more administrations, with the typical range of antibody used being about 0.3 to about 20 mg/kg, more preferably about 0.3 to about 15 mg/kg, administered daily, for example. However, other dosage regimens may be useful. The progress of this therapy is easily monitored by conventional techniques.

Articles of Manufacture

In another embodiment of the invention, an article of manufacture is provided comprising a container which holds the pharmaceutical formulation of the present invention, preferably an aqueous pharmaceutical formulation, and optionally provides instructions for its use. Suitable containers include, for example, bottles, vials and syringes. The container may be formed from a variety of materials such as glass or plastic. An exemplary container is a 3-20 cc single use glass vial. Alternatively, for a multidose formulation, the container may be 3-100 cc glass vial. The container holds the formulation and the label on, or associated with, the container may indicate directions for use. The article of manufacture may further include other materials desirable from a commercial and user standpoint, including other buffers, diluents, filters, needles, syringes, and package inserts with instructions for use.

Exemplification

The present disclosure is further illustrated by the following examples, which should not be construed as further limiting. The contents of all figures and all references, patents and published patent applications cited throughout this application are expressly incorporated herein by reference in their entireties.

Throughout the examples, the following materials and methods were used unless otherwise stated.

General Materials and Methods

In general, the practice of the present invention employs, unless otherwise indicated, conventional techniques of chemistry, molecular biology, recombinant DNA technology, immunology (especially, e.g., antibody technology), and standard techniques of polypeptide preparation. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); and Current Protocols in Molecular Biology, eds. Ausubel et al., John Wiley & Sons (1992).

Thermostability Measurements

Attenuated total reflectance Fourier transform IR (FTIR-ATR) spectra were obtained for various single chains and follow up molecules using the FT-IR Bio-ATR cell in a Tensor Bruker. The molecules were concentrated up to 3 mg/ml and dialyzed overnight at 4° C. against PBS, pH 6.5 and the buffer flow through was collected as blank. The denaturation profiles were obtained by thermo challenging the molecules with a broad range of temperatures in 5° C. steps (25 to 95° C.). All spectra manipulations were performed using OPUS software. The main buffer and transient atmospheric ($CO_2$ and $H_2O$) background were subtracted from the protein spectrum. The resulting protein spectrum was then baseline corrected and the protein amide I spectra was determined from the width of the widest resolvable peak in the expected region. Second derivative spectra were obtained for the amide I band spectra using a third degree polynomial function with a smoothing function. Changes in protein structure were estimated by amide I second derivative analysis using a linear calibration curve for the initial curve-fit calculations assuming 0% denaturation for the 3 lower measurements and 100% denaturation for the 3 higher measurements. The denaturation profiles were used to approximate midpoints of the thermal unfolding transitions (TM) for every variant applying the Boltzmann sigmoidal model.

Solubility Measurements

Relative solubility of various scFv molecules was measured after enhancing protein aggregation and precipitation in presence of ammonium sulfate. Ammonium sulfate was added to the protein in aqueous solutions to yield increments of 5% of saturation in the final mixture salt-protein. The precipitation in the dynamic range was determined empirically and the saturation intervals reduced in this range to 2.5% intervals saturation in the final mixture. After ammonium sulfate addition, samples were gently mixed and centrifuged 30 minutes at 6000 rpm. The remaining protein in supernatants was recovered for each ammonium sulfate percentage of saturation. Solubility curves were determined by measuring the protein concentration in the supernatant using NanoDrop™ 1000 Spectrophotometer. Measurements of remaining soluble protein in supernatants were normalized and used to estimate midpoints of relative solubility for every variant applying the Boltzmann sigmoidal model.

Short Term Stability Test

Protein was examined after two weeks incubation at 40° C. for soluble aggregates and degradation products. Proteins with a concentration of 10 mg/ml were dialyzed overnight at 4° C. against PBS with a broad range of pHs (3.5, 4.5, 5.5, 6.5, 7.0, 7.5 and 8.5). Control protein with the same concentration in standard buffer PBS (pH 6.5) was stored at −80° C. during the 2 weeks period. Determination of degradation bands by SDS-PAGE was done at t=0 and t=14d time points and soluble aggregates were assessed in the SEC-HPLC. Determination of remaining activity after 2 weeks at 40° C. was done using Biacore.

Potency Assay

The neutralizing activity of anti-TNFa binders was assessed in a L929 TNFa-mediated cytotoxicity assay. Toxicity of Mouse L929 fibroblast cells treated with Actinomycin was induced with recombinant human TNF (hTNF). 90% of maximal hTNF-induced cytotoxicity was determined to be at a TNF concentration of 1000 pg/ml. All L929 cells were cultured in RPMI 1640 with phenolred, with L-Glutamine medium supplemented with fetal calf serum (10% v/v). The neutralizing activity of anti-TNFa binders was assessed in RPMI 1640 without phenolred and 5% fetal calf serum. Different concentrations (0-374 ng/mL) of anti-TNF binders are added to L929 cells in presence of 1000 pg/ml hTNF in order to determine the concentration at which the antagonistic effect reaches half-maximal inhibition (EC50%) The dose response curve was fitted with nonlinear sigmoidal regression with variable slope and the EC50 was calculated.

Biacore Binding Analysis of Anti-TNF scFvs

For binding affinity measurements at pH5 and pH 7.4 (data not shown), surface Plasmon resonance measurements with BIAcore™-T100 were employed using a NTA sensor chip and His-tagged TNF (produced at ESBATech). The surface of the NTA sensor chip consists of a carboxymethylated dextran matrix pre-immobilized with nitrilotriacetic acid (NTA) for capture of histidine tagged molecules via $Ni^{2+}$NTA chelation. Human TNFa N-his trimers (5 nM) are captured by the nickel via their N-terminal his-tags and ESBA105 (analyte) is injected at several concentrations ranging from 30 nM to 0.014 nM in 3 fold serial dilution steps. At the regeneration step, the complex formed by nickel, ligand and analyte is washed away. This allows the use of the same regeneration conditions for different samples. The response signal is generated by surface Plasmon resonance (SPR) technology and measured in resonance units (RU). All the measurements are performed at 25° C. Sensorgrams were generated for each anti-TNF scFv sample after in-line reference cell correction followed by buffer sample subtraction. The apparent dissociation rate constant ($k_d$), the apparent association rate constant ($k_a$) and the apparent dissociation equilibrium constant ($K_D$) were calculated using one-to-one Langmuir binding model with BIAcore T100 evaluation Software version 1.1.

EXAMPLE 1

CDR Grafting and Functional Humanization of Monoclonal Rabbit Anti-TNF Antibodies Grafting of Rabbit CDRs Unlike traditional humanization methods which employ the human antibody acceptor framework that shares the greatest sequence homology with the non-human donor antibody, the rabbit CDRs were grafted into either framework FW 1.4 (SEQ ID Nos. 1 and 2, linked by a $(GGGGS)_4$ linker (SEQ ID No: 72)) to generate a Min-graft or into the "rabbitized" framework rFW1.4 (SEQ ID No. 92) or its variant rFW1.4(v2) (SEQ ID No. 93) to generate a Max-graft. Both frameworks were selected primarily for desirable functional properties (solubility and stability), structural suitability to accommodate a large variety of rabbit CDRs and reasonable homology to the rabbit variable domain consensus sequence. Framework rFW1.4 is a derivative of FW1.4 that was further engineered with the aim to serve as universal acceptor framework for virtually any set of rabbit CDRs. Although the stable and soluble framework sequence FW1.4 exhibits high homology to rabbit antibodies, it is not the most homologous sequence available.

Identification of Residues Potentially Involved in Binding

For each rabbit variable domain sequence, the nearest rabbit germline counterpart was identified. If the closest germline could not be established, the sequence was compared against the subgroup consensus or the consensus of rabbit sequences with a high percentage of similarity. Rare framework residues were considered as possible result of somatic hypermutation and therefore playing a role in antigen binding. Consequently, such residues were considered for grafting onto the acceptor framework rFW1.4 or rFW1.4 (v2) to generate Max-grafts. Particularly, residues potentially implicated in direct antigen contact or influencing disposition of VL and VH were grafted. Further residues described to influence CDR structure were substituted if required. No framework substitutions were made when CDRs were grafted onto FW1.4 (Min-grafts). Examples of framework positions that were grafted to obtain the Max-grafts as disclosed herein can be identified by making a sequence alignment of the framework regions of rFW1.4, rFW1.4(v2) and the scFv sequences of interest provided herein. Webtools as known in the art may for example be used for said purpose (e.g. ClustalW or MultiAlin). All framework positions at which rFW1.4 and rFW1.4(v2) contain the same residue and at which the scFv of interest reveals a different residue, are framework positions that were grafted to obtain the Max-grafts.

Domain Shuffling

Variable light chains of Min-grafts were combined with variable heavy chain Max-grafts to identify optimal combinations in terms of biophysical properties (solubility and stability) and activity.

Cloning and Expression of scFvs

The scFvs described and characterized herein were produced as follows. The humanized VL sequences and the humanized VH sequences (SEQ ID NOs:51-88, without SEQ ID NO:72) were connected via the linker of SEQ ID NO:72 to yield an scFv of the following orientation: $NH_2$-VL-linker-VH-COOH (see e.g. SEQ ID NOs:94-121). In many cases DNA sequences encoding for the various scFvs were de novo synthesized at the service provider Entelechon GmbH. The resulting DNA inserts were cloned into the bacterial expression vector pGMP002 via NcoI and HindIII restriction sites introduced at the 5' and 3' end of the scFv DNA sequence, respectively. Between the DNA sequence of the VL domain and the VH domain, a BamHI restriction site is located. In some cases the scFv encoding DNA was not de novo synthesized, but the scFv expressing constructs were cloned by domain shuffling. Accordingly, the VL domains were excised and introduced into the new constructs via NcoI and BamHI restriction sites, the VH domains via BamHI and HindIII restriction sites. In other cases, point mutations were introduced into the VH and/or VL domain using state of the art assembling PCR methods. The cloning of GMP002 is described in Example 1 of WO2008006235. The production of the scFvs was done analogue as for ESBA105 as described in Example 1 of WO2008006235.

EXAMPLE 2

Profiling and Selection of Rabbit CDR Donor Antibodies

The general experimental procedure that was followed for the selection of Rabbit antibodies ("RabMabs") with TNF inhibitory activity is as follows: The rabbit antibodies were employed as donor antibodies for CDRs in the generation of highly soluble TNF immunobinders. Rabbits were immunized with TNFα prior to splenectomy. Splenocytes were isolated from the rabbits for the generation of hybridomas. A total of 44 hybridomas were isolated and supernatants from these hybridomas were profiled for binding affinity, biological potency, and binding specificity.

Figure 1A:
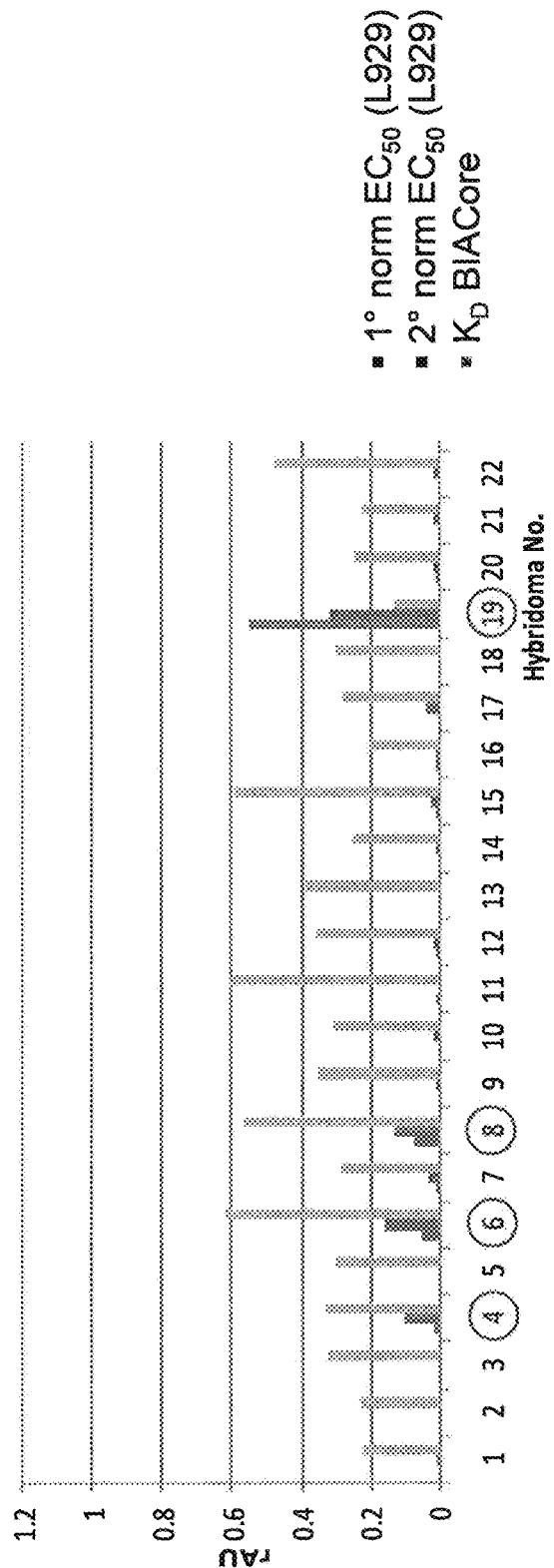

FIG. 1 depicts the relative ability of the supernatants from the 44 anti-TNF RabMab hybridomas in neutralising TNFα in vitro. Neutralization was tested by measuring inhibition of cytotoxicity of TNFα in cultured mouse L929 fibroblasts. The supernatants display different efficacies in the L929 assay. EC50 values (effective concentration to achieve 50% inhibition) were determined in a primary (blue bars) and secondary screens (red bars) and normalized with respect to the best performer in each assay. TNF Binding affinity was also measured by BIACore analysis for each RabMab (green bars).

Figure 2:
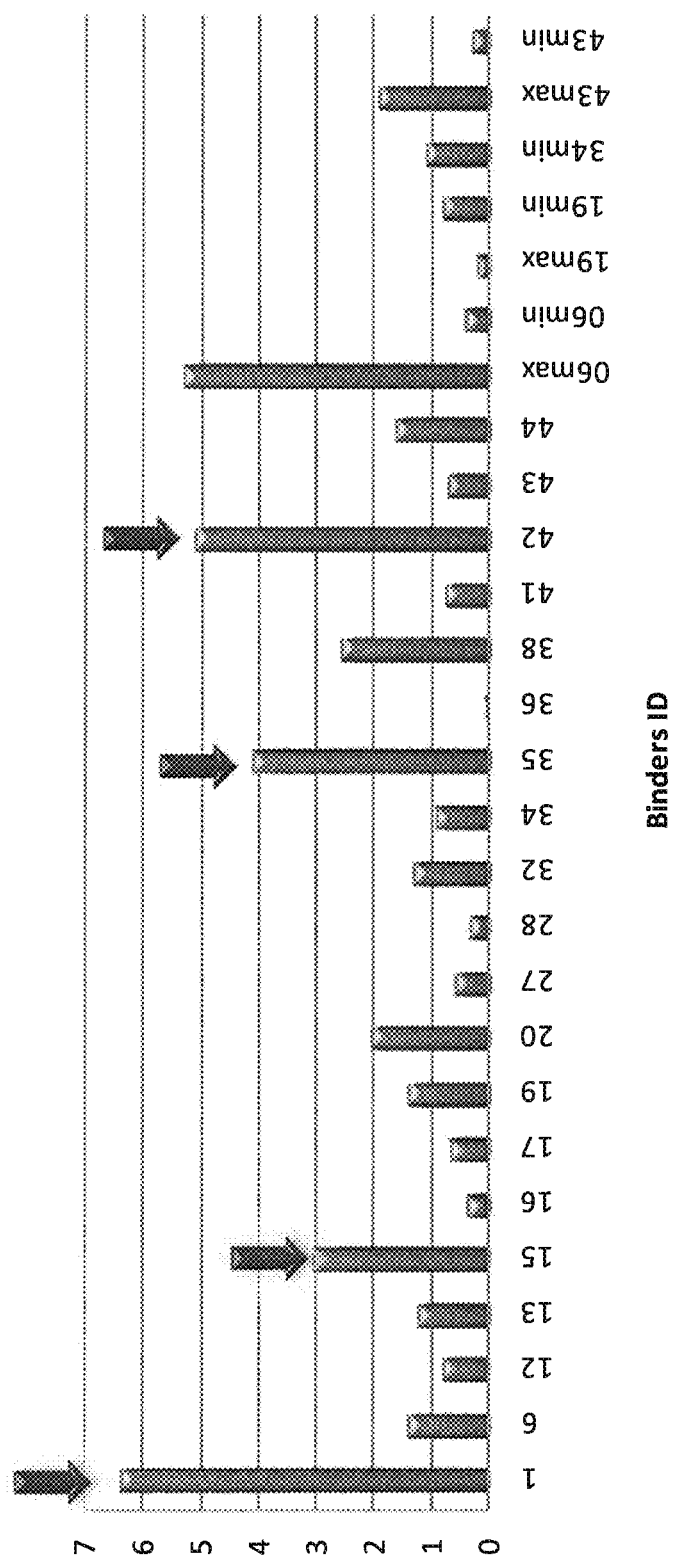
FIG. 2 depicts the ability of 20 anti-TNF RabMab single-chain antibodies and 7 humanized anti-TNF single-chain antibodies in selectively binding TNFα (ELISA secretion assay, please note that for this assay supernatant from bacterial culture was used, which was not normalized for single-chain antibody content).

RabMabs encoded by each hybridoma were also sequenced and the sequences subjected to phylogenetic analysis based on the prediction of epitope clusters. Four representative Rabmabs (EPI-6, EPI-19, EPI-34, and EPI-43) with high binding activity and potent neutralizing activity were selected from among different phylogenetic families as donor antibodies for CDR grafting. Additional four (4) Rabmabs (EPI-1, EPI-15, EP-35 and EP-42) were selected for CDR grafting based on their favorable activity in a secretion ELISA (see FIG. 2).

EXAMPLE 3

CDR Grafting and Functional Humanization of Rabbit Donor Antibodies

Unlike traditional humanization methods which employ the human antibody acceptor framework that shares the greatest sequence homology with the non-human donor antibody, the rabbit CDRs were grafted into a human framework (FW 1.4) that was preselected for desirable functional properties (solubility and stability) using a Quality Control assay. Although the stable and soluble framework sequence exhibited high homology with the RabMab, the selected acceptor antibody is not the most homologous sequence available.

A number of CDR grafts were generated for each of the rabmabs. The term "Min-graft" or "min" as used herein refers to a humanized variable domain that was generated by grafting of rabbit CDRs from a rabbit variable domain into a naturally occurring human acceptor framework (FW 1.4, SEQ ID Nos. 1 and 2, linked by a (GGGGS)$_4$ linker (SEQ ID No: 72)). No changes in the framework regions are made. The framework itself was preselected for desirable functional properties (solubility and stability). The term "Max-graft" or "max" as used herein refers to a humanized variable domain that was generated by grafting of rabbit CDRs from a rabbit variable domain into the "rabbitized", human acceptor framework "RabTor" (rFW1.4, SEQ ID No. 92), or into a derivative thereof referred to as rFW1.4(v2) (SEQ ID No. 93). The "RabTor" framework was prepared by incorporating conserved rabbit residues (otherwise which are rather variable in other species) at framework positions generally involved in rabbit variable domain structure and stability, with the aim to generate a universally applicable framework that accepts virtually any set of rabbit CDRs without the need to graft donor framework residues other than at positions that are different in their presumable progenitor sequence, e.g. that were altered during somatic hypermutation and thus, possibly contribute to antigen binding. The presumable progenitor sequence is defined to be the closest rabbit germline counterpart and in case the closest germline counterpart cannot be established, the rabbit subgroup consensus or the consensus of rabbit sequences with a high percentage of similarity. "Min-Max" or "minmax" refer to a humanized variable domain consisting of a "Min-graft" variable light chain combined with a "Max-graft" variable heavy chain, whereas "Max-Min" or "maxmin" refer to a humanized variable domain consisting of a "Max-graft" variable light chain combined with a "Min-graft" variable heavy chain.

Table 2 shows a summary of the detailed characterization data for humanized single chain antibodies that originate from eight different monoclonal rabbit antibodies or rabmabs (EP1, EP6, EP15, EP19, EP34, EP35, EP42 and EP43). So-called "min" grafts (e.g. EP1 min) refer to constructs for which only the rabbit donor CDRs were grafted, whereas for the so-called "max" grafts, not only the CDRs, but also some amino acid positions in the donor framework were grafted. Additionally, the table 2 shows the data for two His-tagged single-chain antibodies (EP34 min_C-His and EP19max_C-His), as well as the reference single chain antibody ESBA105 described in WO 2006/131013. The third column, referred to as "L929" indicates the relative potencies of the different single chain antibodies as determined in a L929 assay an compared to the potency of ESBA105. The values for kon, koff and $K_D$ are given in units of $M^{-1} s^{-1}$, $s^{-1}$ and M, respectively. The seventh column gives the mid point of thermally induced unfolding as determined with FT-IR. The last column indicates the relative yield of correctly folded protein obtained from solubilized inclusion bodies after a refolding approach.

Figure 3A:
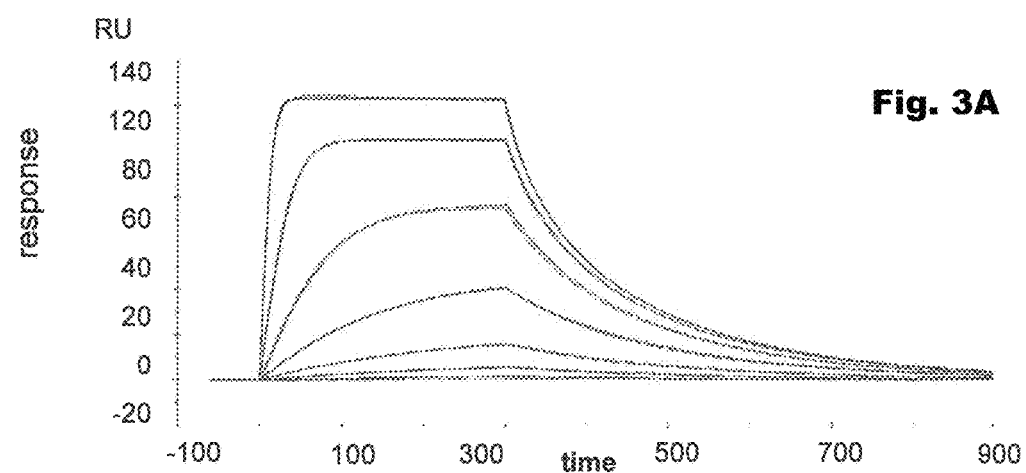
FIG. 3A and FIG. 3B depict the binding kinetics (FIG. 3A) of EP43max and the binding kinetics (FIG. 3B) of EP34max to human TNF alpha.
Figure 3B:
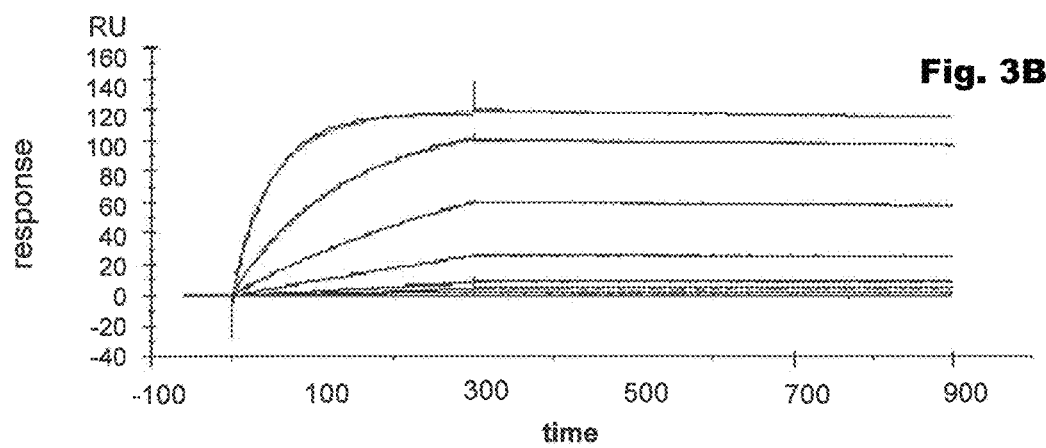
Figure 4:
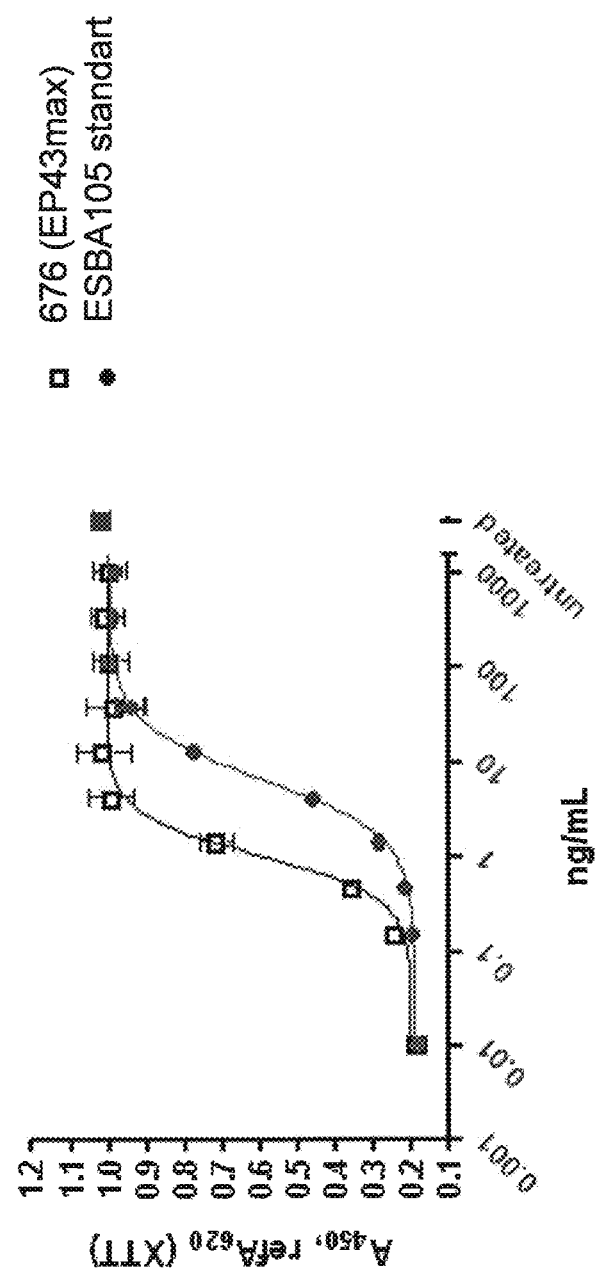
FIG. 4 depicts the potency of EP43max (open squares) the potency (closed circles) of ESBA105. The EC50 of EP43max is 1 ng/ml and the EC50 of ESBA105 is 6.5 ng/ml.

Some examples for BIACore data that went into table 2 are given in FIG. 3: Binding kinetics for ESBA105 (FIG. 3a), EP43max (FIG. 3b) and EP34max (FIG. 3c) binding to human TNFα are shown. Examples for cellular potency assays are given in FIG. 4, which compares ESBA105 (closed circles) against EP43max (open squares) in a L929 assay. Further examples of cellular potency assays that compare EP34max against the marketed antibodies infliximab and adalimumab are given in FIGS. 9 and 10.

TABLE 2

Summary of the detailed characterization data for the four rabbit monoclonals (EP6, EP19, EP34 and EP43) and their CDR grafted variants.

| Description | ID | L929* | kon | koff | $K_D$ | FT-IR TM ° C. | RF yield** |
|---|---|---|---|---|---|---|---|
| EP1_min | 1071 | ND*** | — | — | — | — | 2 |
| EP6_min | 673 | ND*** | 4.67E+04 | 4.94E−03 | 1.06E−07 | 50.2 | 35 |
| EP15_min | 1073 | ND*** | 1.57E+05 | 4.10E−02 | 2.62E−07 | — | 41.5 |
| EP19_min | 616 | ND*** | — | — | — | — | — |
| EP34_min | 643 | ND*** | — | — | — | — | — |
| EP35_min | 1075 | ND*** | — | — | — | — | 1 |
| EP42_min | 1076 | ND*** | 1.42E+05 | 8.35E−03 | 5.87E−08 | — | 3 |
| EP43_min | 705 | ND*** | 5.38E+03 | 2.98E−02 | 5.54E−06 | 70.2 | 30.0 |
| EP1_max | 1072 | ND*** | 1.11E+04 | 6.30E−04 | 5.69E−08 | — | 44 |
| EP6_max | 674 | 1.1 | 2.84E+05 | 1.45E−04 | 5.12E−10 | 48.1 | 12 |
| EP15_max | 1074 | 0.39 | 1.53E+06 | 2.26E−03 | 1.48E−09 | 68.6 | 57.8 |

TABLE 2-continued

Summary of the detailed characterization data for the four rabbit monoclonals (EP6, EP19, EP34 and EP43) and their CDR grafted variants.

| Description | ID | L929* | kon | koff | $K_D$ | FT-IR TM ° C. | RF yield** |
|---|---|---|---|---|---|---|---|
| EP19_max | 1007 | 0.6 | 2.25E+04 | 6.54E−05 | 2.91E−09 | 53.5 | 52 |
| EP34_max | 791 | 10.5 | 5.86E+05 | 1.68E−05 | 2.86E−11 | 72.4 | 4.05 |
| EP35_max | 1089 | 5.20 | 7.72E+05 | 1.50E−04 | 1.94E−10 | — | 0.66 |
| EP42_max | 1077 | ND*** | 1.21E+05 | 4.19E−04 | 3.46E−09 | — | 47.6 |
| EP43_max | 676 | 6.4 | 1.78E+05 | 4.48E−05 | 2.51E−10 | 74.3 | 21.73 |
| EP34min_C-His | 790 | 0.2 | | | | | |
| EP19max_C-His | 789 | 1.9 | | | | | |

*L929 [EC50-E105/EC50-X], compared in mass units [ng/ml] relative to the performance of ESBA105 (WO06/131013)
**(mg/L refolding solution);
***Not Determined

EXAMPLE 4

Solubility and Stability Optimization of EP43max, a Potent TNFα Binder

Figure 5:
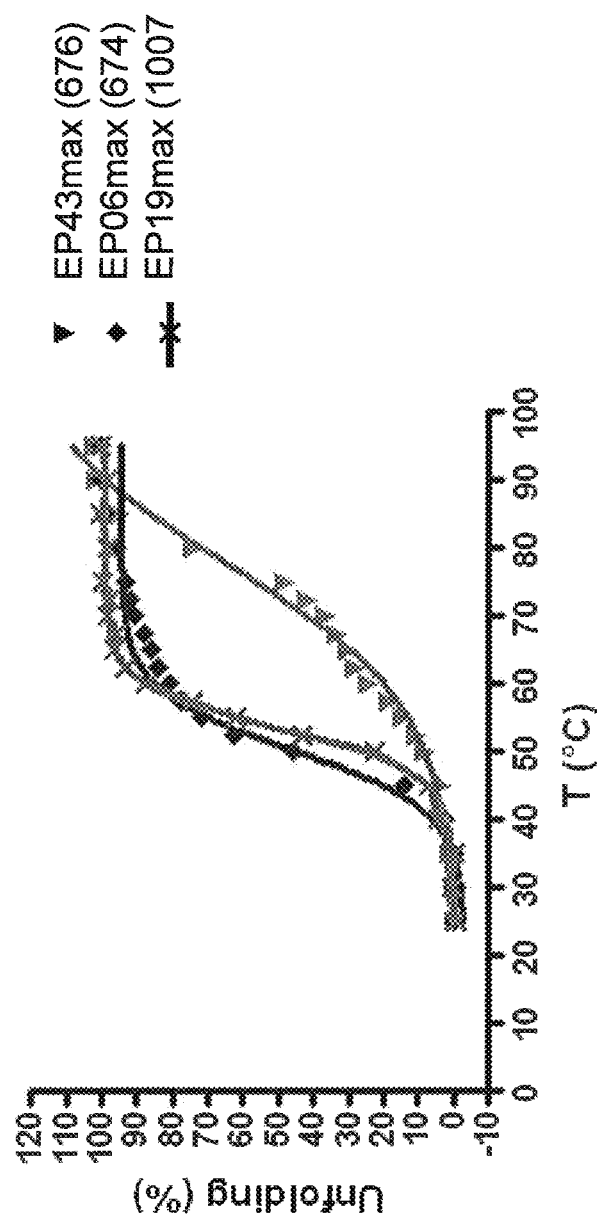
FIG. 5 depicts the performance of EP43max, EP6max and EP19max in a thermal unfolding assay (FTIR).

EP43max was selected for further optimization based on its potent TNF binding activity. Biophysical characterization of this immunobinder revealed that it exhibits a high midpoint of denaturation (Tm>70° C.) in a thermal unfolding assay (FTIR) (see FIG. 5). Nevertheless, EP43max was subjected to solubility optimization to narrow its broad transition phase in thermal unfolding. In order to improve the solubility of the native EP43max, the three residue positions 12, 103, or 144 in the VH chain were substituted with amino acids with higher hydophilicity. This combination was shown to increase the solubility of the native protein without affecting stability or binding activity. (V→S at AHo position 12, V→T at AHo position 103, and L→T at AHo position 144) were introduced to replace hydrophobic residues in the V-C domain interface of the variable heavy chain (VH) region of EP43max. In addition to the solubility enhancing mutations, nine stabilizing mutations (T10S, K47R, Y57S, L91F and T103V in the VL and E1Q, E6Q, S7T and V103L I the VH) were identified in EP43max (see Table 3). These stabilizing residues were identified from a functional consensus analysis of ESBATech's quality control (QC) frameworks. Stabilizing residues at positions 1 and 3 in the VL and position 89 in the VH were already present in the EP43max molecule. An additional stabilizing mutation (M→L) was identified at VL position 4, but was eliminated from consideration based on it predicted role in antigen binding.

TABLE 3

Stabilizing Mutations in EP43max

| Domain | Position | Parental Residue | Preferred Substition | Stabilizing Mutation |
|---|---|---|---|---|
| VL | 1 | E | E | Already Present |
| VL | 3 | V | V | Already Present |
| VL | 4 | M | L | Involved in Binding |
| VL | 10 | T | S | T10S |
| VL | 47 | K | R | K47R |
| VL | 57 | Y | S | Y57S |
| VL | 91 | L | F | L91F |
| VL | 103 | T | V | T103V |
| VH | 1 | E | Q | E1Q |
| VH | 6 | E | Q | E6Q |
| VH | 7 | S | T | S7T |
| VH | 89 | V | V | Already Present |
| VH | 103 | V | L | V103L |

Column 1, Variable domain.
Column 2, AHo amino acid position.
Column 3, parental residue in EP43max.
Column 4, preferred substitution for the position indicated in column 2.
Column 5, stabilizing mutation.

EXAMPLE 5

Optimized Variants of EP43max, a Potent TNFα Binder

Tables 4 and 5 show the characterization data for three optimized variants of EP43max. EP43_maxDHP is solubility enhanced variant of EP43max and comprises the three solubility enhancing mutations above (V→S at AHo position 12, V→T at AHo position 103, and L→T at AHo position 144). EP43_maxmin and EP43_minmax variants were generated by domain shuffling between "min" and "max" grafts. E.g., the "minmax" variant comprises the minimal graft (CDR-graft only) version of the light chain and maximal graft version of the heavy chain (i.e., grafted rabbit CDRs plus rabbit framework residues involved in antigen binding) whereas, the "maxmin" variant comprised the maximal graft version of the light chain and the minimal graft version of the heavy chain.

TABLE 4

Characterization data for EP43max and variant thereof.

|  | FW | L929* | Kon | Koff | KD | FT-IR stability TM ° C. |
|---|---|---|---|---|---|---|
| EP43_max | 1.4 | 6.4 | 2.28E+05 | 5.68E−05 | 2.49E−10 | 74.32 |
| EP43_maxDHP | 1.4 | 6.7 | 2.35E+05 | 2.73E−05 | 1.16E−10 | 60.15 |
| EP43_maxmin | 1.4 | Inactive | 1.46E+05 | 5.33E−03 | 3.66E−08 | 51.76 |
| EP43_minmax | 1.4 | 1.6 | 2.28E+05 | 1.98E−04 | 8.68E−10 | 65.81 |

*L929 [EC50-E105/EC50-X], compared in mass units [ng/ml]

TABLE 5

Characterization data for EP43max and variant thereof.

|  | RF yield | Expression | Refolding screening | Purification |
|---|---|---|---|---|
| EP43_max | 27.73 | +++ | ok | ok |
| EP43_maxDHP | 17 | +++ | ok | ok |
| EP43_maxmin | 11 | +++ | ok | ok |
| EP43_minmax | 46 | +++ | ok | ok |

Figure 6:
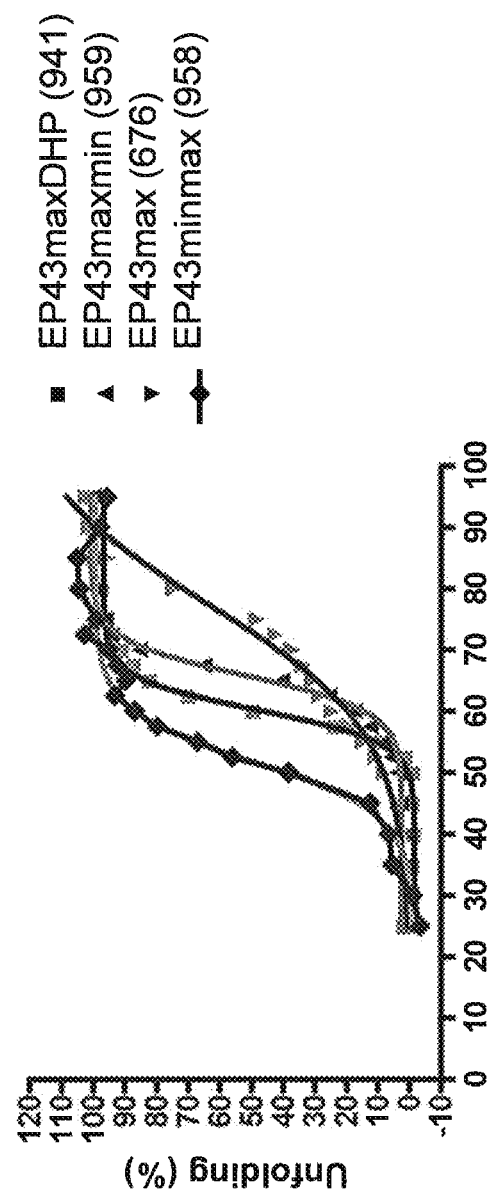
FIG. 6 depicts the thermal denaturation curves of EP43max and derivatives thereof as compared by FTIR analysis.

The thermal denaturation curves of EP43max and its optimized variants were compared by FTIR analysis (see FIG. 6 and Table 6). EP43minmax was found to have a lower midpoint of unfolding than EP43max.

TABLE 6

Comparison of thermal denaturation curves of EP43max and its optimized variants by FTIR analysis

|  | EP43maxDHP | EP43maxmin (959) | EP43max (676) | EP43minmax (958) |
|---|---|---|---|---|
| Tm° C. | 60.15 | 65.81 | 77.78 | 51.76 |
| Slope | 2.618 | 2.908 | 10.43 | 4.297 |
| $R^2$ | 0.9974 | 0.9969 | 0.9855 | 0.9936 |

Figure 7A:
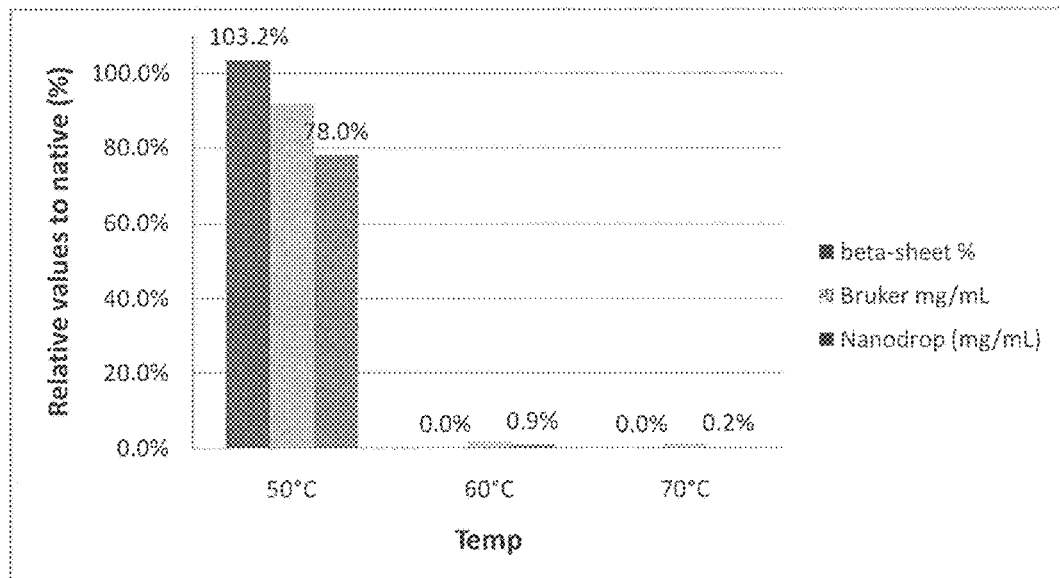
FIG. 7A and FIG. 7B depict the comparison of EP43 max (FIG. 7A) and its EP43minmax variant (FIG. 7B) in a thermal stress test.
Figure 7B:
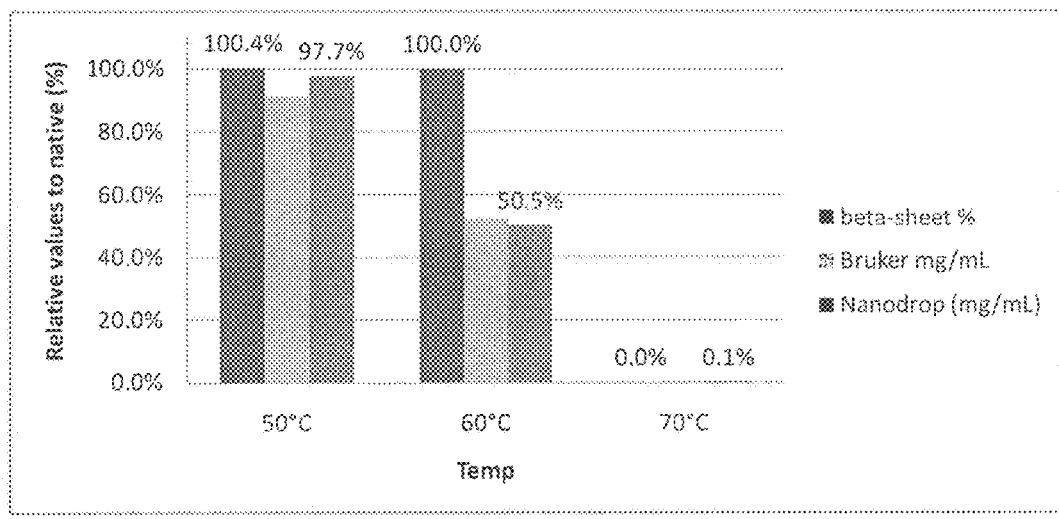

Moreover, the mimax variant exhibited a one-step unfolding transition, indicating that both domains unfold at very similar temperatures. EP43 max (FIG. 7A) and its EP43minmax variant (FIG. 7B) were further compared in a thermal stress test. Beta-sheet content and concentration of soluble protein were evaluated following thermal concentration at increasing temperatures (50, 60 and 70° C.). EP43minmax was considerably more stable than EP43max at the intermediate temperature of 60° C.

EXAMPLE 6

Comparison of EP34max with Commercially Available TNFα Binders

The capacity of EP34max, Adalimumab and Infliximab to block cytotoxic activity of 1000 pg/ml recombinant human TNFalpha was compared as detailed above in a L929 assay. The capacity of EP43max, Adalimumab and Infliximab to block cytotoxic activity of 10 pg/ml recombinant human TNFalpha was assessed in a Kym-1 assay. The results are shown in FIGS. 9a, b and FIGS. 10a, b, respectively.

Figure 9A:
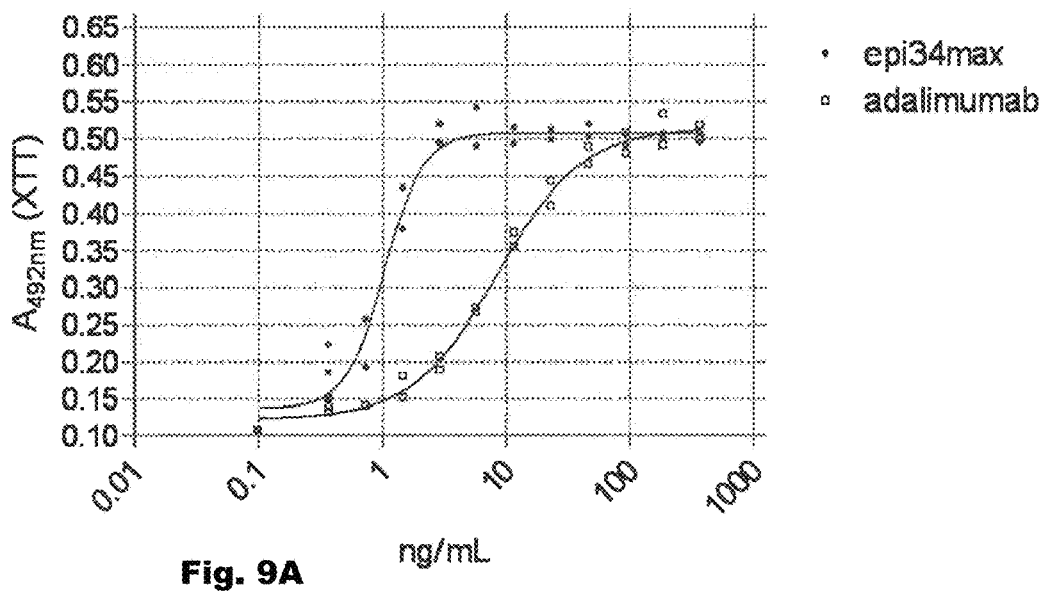
FIG. 9A illustrates the potency of Epi34max and Adalimumab to block cytotoxic activity of 1000 pg/ml recombinant human TNFalpha (murine L929 cells). The $IC_{50}$ for Ep34max and Adalimumab was determined to be 1.03 ng/ml and 8.46 ng/ml, respectively.
Figure 9B:
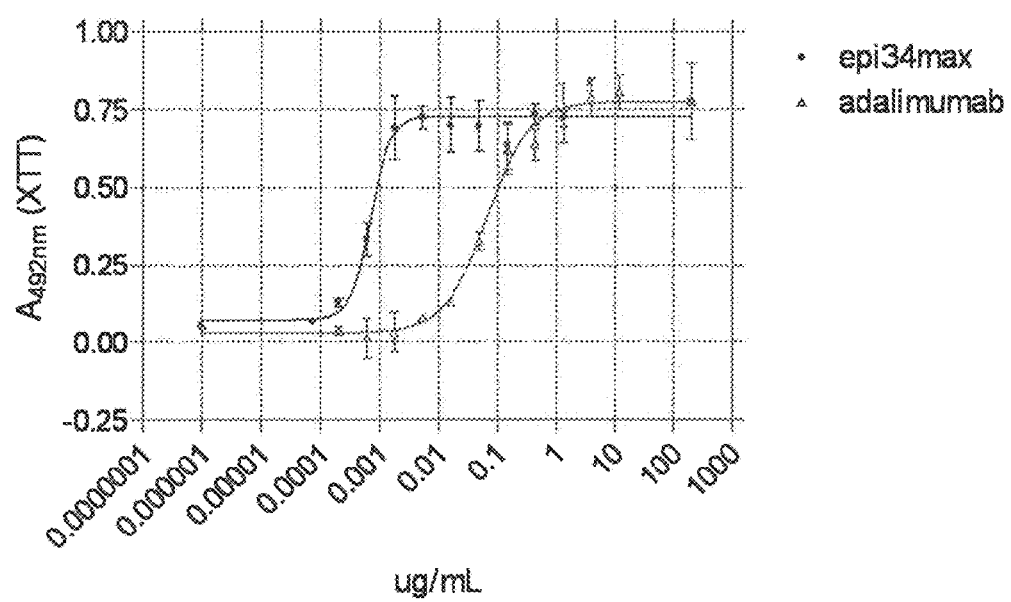
FIG. 9B illustrates the potency of Adalimumab and Ep34max to block cytotoxic activity of 10 pg/ml recombinant human TNFalpha (human Kym-1 cells). The $IC_{50}$ for Infliximab and Ep34max (791) was determined to be 66.2 ng/ml and 0.69 ng/ml respectively.
Figure 11:
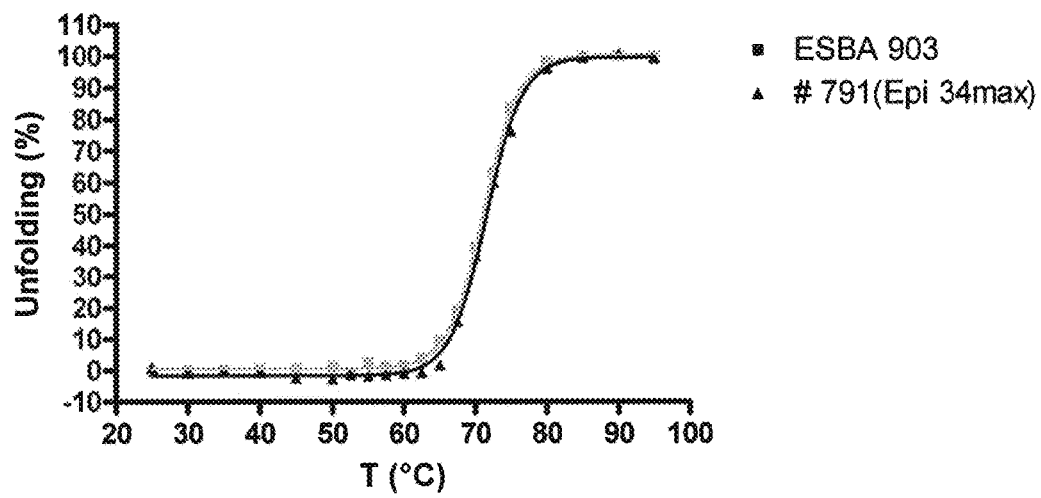
FIG. 11 illustrates the BioATR FT-IR thermal denaturation profile fitted from Fourier transformed infrared spectra in the amide I band region of Ep34 max in comparison to ESBA903. V50 for ESBA903 was 71.12 and for EP34max 71.50; the slope or ESBA903 2.481 and 2.540 for EP34max.
Figure 12:
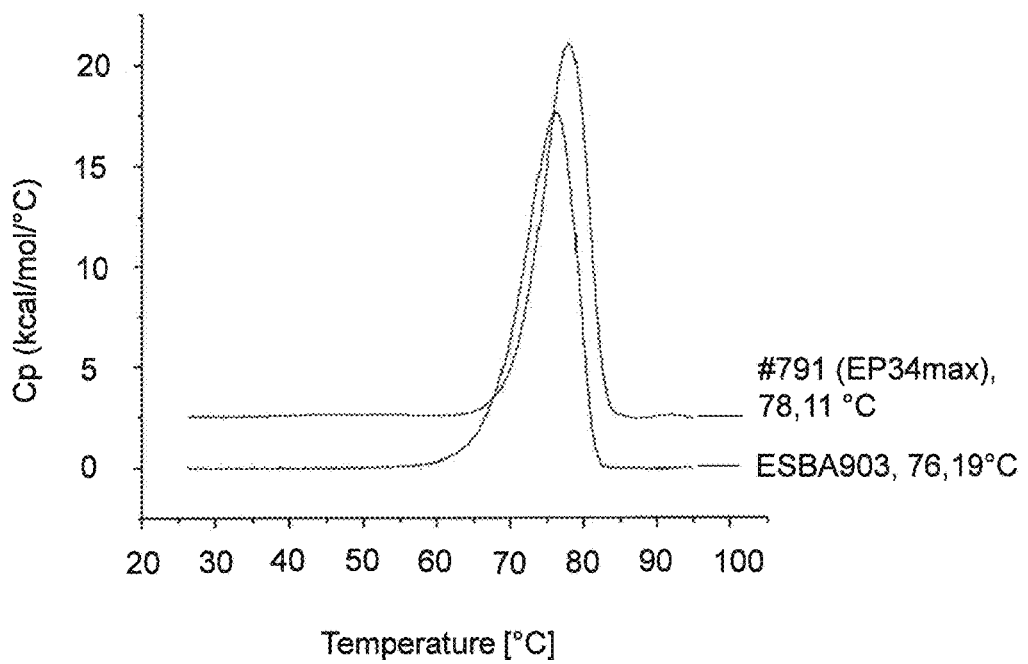
FIG. 12 illustrates the DSC thermal unfolding curves of Ep34max and ESBA903 scFv antibodies. Tm of EP 34max is 78.11° C. and Tm for ESBA903 is 76.19° C.

FIG. 9a illustrates the potency of EP34max and Adalimumab to block cytotoxic activity of 1000 pg/ml recombinant human TNFalpha (murine L929 cells). The $IC_{50}$ for EP34max and Adalimumab was determined to be 1.03 ng/ml and 8.45 ng/ml, respectively. FIG. 9b illustrates the potency of Adalimumab and EP34max to block cytotoxic activity of 10 pg/ml recombinant human TNFalpha (human Kym-1 cells). The $IC_{50}$ for Adalimumab and EP34max (791) was determined to be 66.2 ng/ml and 0.69 ng/ml respectively.

FIG. 10a illustrates the potency of EP34max and Infliximab to block cytotoxic activity of 1000 pg/ml recombinant human TNFalpha (murine L929 cells). The $IC_{50}$ for EP34max and Infliximab was determined to be 1.04 ng/ml and 13.9 ng/m, respectively. FIG. 10b illustrates the potency of Infliximab and EP34max (791) to block cytotoxic activity of 10 pg/ml recombinant human TNFalpha (human Kym-1 cells). The $IC_{50}$ for Infliximab and EP34max was determined to be 14.98 ng/ml and 0.63 ng/ml respectively. Thus, in both cases, EP34max showed better performance as Infliximab.

Other Embodiments

It is understood that the invention also includes any of the methodologies, references, and/or compositions set forth in the attached Appendices A to E.

Equivalents

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations, web pages, figures and/or appendices, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

While the present inventions have been described in conjunction with various embodiments and examples, it is not intended that the present teachings be limited to such embodiments or examples. On the contrary, the present inventions encompass various alternatives, modifications, and equivalents, as will be appreciated by those of skill in the art.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

The invention claimed is:

1. An isolated nucleic acid molecule encoding at least one of a variable heavy (VH) chain region and a variable light (VL) chain region, wherein:

the variable heavy chain region has a human heavy chain variable framework sequence and CDR H1, CDR H2 and CDR H3 sequences, wherein the human heavy chain variable region framework has at least 90% identity to SEQ ID NO:2; and the variable light chain region has a human light chain variable framework sequence and CDR L1, CDR L2 and CDR L3 sequences, wherein the human light chain variable region framework sequence has at least 85% identity to SEQ ID NO:1, wherein (a) the CDR sequences are SEQ ID NO: 3, SEQ ID NO: 4, SEQ ID NO: 5, SEQ ID NO: 6, SEQ ID NO: 7 and SEQ ID NO: 8;

(b) the CDR sequences are SEQ ID NO: 9, SEQ ID NO: 10, SEQ ID NO: 11, SEQ ID NO: 12, SEQ ID NO: 13 and SEQ ID NO: 14;

(c) the CDR sequences are SEQ ID NO: 15, SEQ ID NO: 16, SEQ ID NO: 17, SEQ ID NO: 18, SEQ ID NO: 19 and SEQ ID NO: 20;

(d) the CDR sequences are SEQ ID NO: 21, SEQ ID NO: 22, SEQ ID NO: 23, SEQ ID NO: 24, SEQ ID NO: 25 and SEQ ID NO: 26;
(e) the CDR sequences are SEQ ID NO: 27, SEQ ID NO: 28, SEQ ID NO: 29, SEQ ID NO: 30, SEQ ID NO: 31 and SEQ ID NO: 32;
(f) the CDR sequences are SEQ ID NO: 33, SEQ ID NO: 34, SEQ ID NO: 35, SEQ ID NO: 36, SEQ ID NO: 37 and SEQ ID NO: 38;
(g) the CDR sequences are SEQ ID NO: 39, SEQ ID NO: 40, SEQ ID NO: 41, SEQ ID NO: 42, SEQ ID NO: 43 and SEQ ID NO: 44; or
(h) the CDR sequences are SEQ ID NO: 45, SEQ ID NO: 46, SEQ ID NO: 47, SEQ ID NO: 48, SEQ ID NO: 49 and SEQ ID NO: 50.

2. The isolated nucleic acid molecule of claim 1, wherein the human heavy chain variable region framework is or comprises SEQ ID NO:2, SEQ ID NO: 89, or SEQ ID NO: 90, and the human light chain variable region framework sequence is or comprises SEQ ID NO: 1 or SEQ ID NO: 91.

3. The isolated nucleic acid molecule of claim 1, comprising one or more substitutions in the heavy chain framework (VH) at a position from the group consisting of positions H24, H25, H56, H82, H84, H89 and H108; and/or a substitution in the light chain framework (VL) at position L87 according to the AHo numbering system.

4. The isolated nucleic acid molecule of claim 3, wherein the substitution is selected from the group consisting of threonine (T) at position H24, valine (V) at position H25, glycine (G) or alanine (A) at position H56, lysine (K) at position H82, threonine (T) at position H84, valine (V) at position H89 and arginine (R) at position H108 and threonine (T) at position L87 according to the AHo numbering system.

5. The isolated nucleic acid molecule of claim 1, wherein heavy chain framework (VH) comprises a solubility enhancing substitution in at least one of heavy chain amino positions 12, 103 and 144 (AHo numbering).

6. The isolated nucleic acid molecule of claim 5, wherein the solubility enhancing substitution is selected from the group consisting of: (a) Serine (S) at position 12; (b) Threonine (T) at position 103; and (c) Threonine (T) at position 144.

7. The isolated nucleic acid molecule of claim 1, wherein:
(a) the heavy chain variable region (VH) has at least 90% sequence identity to a sequence selected from the group consisting of SEQ ID NO:51, SEQ ID NO:53 and SEQ ID NO: 55, and the light chain variable region (VL) has at least 90% sequence identity to a sequence selected from the group consisting of SEQ ID NO:52, SEQ ID NO:54, SEQ ID NO: 56, SEQ ID NO: 57, SEQ ID NO:58 and SEQ ID NO: 59;
(b) the heavy chain variable region (VH) has at least 90% sequence identity to a sequence selected from the group consisting of SEQ ID NO:60 and SEQ ID NO:62, and the light chain variable region (VL) having at least 90% sequence identity to a sequence selected from the group consisting of SEQ ID NO:61 and SEQ ID NO:63;
(c) the heavy chain variable region (VH) has at least 90% sequence identity to a sequence selected from the group consisting of SEQ ID NO:64 and SEQ ID NO:66, and the light chain variable region (VL) has at least 90% sequence identity to a sequence selected from the group consisting of SEQ ID NO:65 and SEQ ID NO:67;
(d) the heavy chain variable region (VH) has at least 90% sequence identity to a sequence selected from the group consisting of SEQ ID NO:64 and SEQ ID NO:66, and the light chain variable region (VL) has at least 90% sequence identity to a sequence selected from the group consisting of SEQ ID NO:65 and SEQ ID NO:67;
(e) the heavy chain variable region (VH) has at least 90% sequence identity to a sequence selected from the group consisting of SEQ ID NO:68 and SEQ ID NO:70, and the light chain variable region (VL) has at least 90% sequence identity to a sequence selected from the group consisting of SEQ ID NO:69 and SEQ ID NO:71;
(f) the heavy chain variable region (VH) has at least 90% sequence identity to a sequence selected from the group consisting of SEQ ID NO:73 and SEQ ID NO:75, and the light chain variable region (VL) has at least 90% sequence identity to a sequence selected from the group consisting of SEQ ID NO:74 and SEQ ID NO:76;
(g) the heavy chain variable region (VH) has at least 90% sequence identity to a sequence selected from the group consisting of SEQ ID NO:77 and SEQ ID NO:79, and the light chain variable region (VL) has at least 90% sequence identity to a sequence selected from the group consisting of SEQ ID NO:78 and SEQ ID NO:80;
(h) the heavy chain variable region (VH) has at least 90% sequence identity to a sequence selected from the group consisting of SEQ ID NO:81 and SEQ ID NO:83, and the light chain variable region (VL) has at least 90% sequence identity to a sequence selected from the group consisting of SEQ ID NO:82 and SEQ ID NO:84; or
(i) the heavy chain variable region (VH) has at least 90% sequence identity to a sequence selected from the group consisting of SEQ ID NO:85 and SEQ ID NO:87, and the light chain variable region (VL) has at least 90% sequence identity to a sequence selected from the group consisting of SEQ ID NO:86 and SEQ ID NO:88.

8. An expression vector comprising the nucleic acid molecule of claim 1.

9. An isolated host cell comprising the expression vector of claim 8.

10. An isolated nucleic acid molecule encoding an immmunobinder, which specifically binds TNFβ, the immunobinder comprising:
a human heavy chain variable framework sequence and CDR H1, CDR H2 and CDR H3 sequences, wherein the human heavy chain variable region framework has at least 90% identity to SEQ ID NO:2; and
a human light chain variable framework sequence and CDR L1, CDR L2 and CDR L3 sequences, wherein the human light chain variable region framework sequence has at least 85% identity to SEQ ID NO:1, wherein
(a) the CDR sequences are SEQ ID NO: 3, SEQ ID NO: 4, SEQ ID NO: 5, SEQ ID NO: 6, SEQ ID NO: 7 and SEQ ID NO: 8;
(b) the CDR sequences are SEQ ID NO: 9, SEQ ID NO: 10, SEQ ID NO: 11, SEQ ID NO: 12, SEQ ID NO: 13 and SEQ ID NO: 14;
(c) the CDR sequences are SEQ ID NO: 15, SEQ ID NO: 16, SEQ ID NO: 17, SEQ ID NO: 18, SEQ ID NO: 19 and SEQ ID NO: 20;
(d) the CDR sequences are SEQ ID NO: 21, SEQ ID NO: 22, SEQ ID NO: 23, SEQ ID NO: 24, SEQ ID NO: 25 and SEQ ID NO: 26;
(e) the CDR sequences are SEQ ID NO: 27, SEQ ID NO: 28, SEQ ID NO: 29, SEQ ID NO: 30, SEQ ID NO: 31 and SEQ ID NO: 32;
(f) the CDR sequences are SEQ ID NO: 33, SEQ ID NO: 34, SEQ ID NO: 35, SEQ ID NO: 36, SEQ ID NO: 37 and SEQ ID NO: 38;

(g) the CDR sequences are SEQ ID NO: 39, SEQ ID NO: 40, SEQ ID NO: 41, SEQ ID NO: 42, SEQ ID NO: 43 and SEQ ID NO: 44; or (h) the CDR sequences are SEQ ID NO: 45, SEQ ID NO: 46, SEQ ID NO: 47, SEQ ID NO: 48, SEQ ID NO: 49 and SEQ ID NO: 50.

11. The isolated nucleic acid molecule of claim 10, wherein the human heavy chain variable region framework is or comprises SEQ ID NO:2, SEQ ID NO: 89, or SEQ ID NO: 90, and the human light chain variable region framework sequence is or comprises SEQ ID NO: 1 or SEQ ID NO: 91.

12. The isolated nucleic acid molecule of claim 10, wherein the immunobinder comprises one or more substitutions in the heavy chain framework (VH) at a position from the group consisting of positions H24, H25, H56, H82, H84, H89 and H108; and/or a substitution in the light chain framework (VL) at position L87 according to the AHo numbering system.

13. The isolated nucleic acid molecule of claim 12, wherein the substitution is selected from the group consisting of threonine (T) at position H24, valine (V) at position H25, glycine (G) or alanine (A) at position H56, lysine (K) at position H82, threonine (T) at position H84, valine (V) at position H89 and arginine (R) at position H108 and threonine (T) at position L87 according to the AHo numbering system.

14. The isolated nucleic acid molecule of claim 10, wherein heavy chain framework (VH) comprises a solubility enhancing substitution in at least one of heavy chain amino positions 12, 103 and 144 (AHo numbering).

15. The isolated nucleic acid molecule of claim 14, wherein the solubility enhancing substitution is selected from the group consisting of: (a) Serine (S) at position 12; (b) Threonine (T) at position 103; and (c) Threonine (T) at position 144.

16. The isolated nucleic acid molecule of claim 10, wherein:

(a) the heavy chain variable region (VH) has at least 90% sequence identity to a sequence selected from the group consisting of SEQ ID NO:51, SEQ ID NO:53 and SEQ ID NO: 55, and the light chain variable region (VL) has at least 90% sequence identity to a sequence selected from the group consisting of SEQ ID NO:52, SEQ ID NO:54, SEQ ID NO: 56, SEQ ID NO: 57, SEQ ID NO:58and SEQ ID NO: 59;

(b) the heavy chain variable region (VH) has at least 90% sequence identity to a sequence selected from the group consisting of SEQ ID NO:60 and SEQ ID NO:62, and the light chain variable region (VL) having at least 90% sequence identity to a sequence selected from the group consisting of SEQ ID NO:61 and SEQ ID NO:63;

(c) the heavy chain variable region (VH) has at least 90% sequence identity to a sequence selected from the group consisting of SEQ ID NO:64 and SEQ ID NO:66, and the light chain variable region (VL) has at least 90% sequence identity to a sequence selected from the group consisting of SEQ ID NO:65 and SEQ ID NO:67;

(d) the heavy chain variable region (VH) has at least 90% sequence identity to a sequence selected from the group consisting of SEQ ID NO:64 and SEQ ID NO:66, and the light chain variable region (VL) has at least 90% sequence identity to a sequence selected from the group consisting of SEQ ID NO:65 and SEQ ID NO:67;

(e) the heavy chain variable region (VH) has at least 90% sequence identity to a sequence selected from the group consisting of SEQ ID NO:68 and SEQ ID NO:70, and the light chain variable region (VL) has at least 90% sequence identity to a sequence selected from the group consisting of SEQ ID NO:69 and SEQ ID NO:71;

(f) the heavy chain variable region (VH) has at least 90% sequence identity to a sequence selected from the group consisting of SEQ ID NO:73 and SEQ ID NO:75, and the light chain variable region (VL) has at least 90% sequence identity to a sequence selected from the group consisting of SEQ ID NO:74 and SEQ ID NO:76;

(g) the heavy chain variable region (VH) has at least 90% sequence identity to a sequence selected from the group consisting of SEQ ID NO:77 and SEQ ID NO:79, and the light chain variable region (VL) has at least 90% sequence identity to a sequence selected from the group consisting of SEQ ID NO:78 and SEQ ID NO:80;

(h) the heavy chain variable region (VH) has at least 90% sequence identity to a sequence selected from the group consisting of SEQ ID NO:81 and SEQ ID NO:83, and the light chain variable region (VL) has at least 90% sequence identity to a sequence selected from the group consisting of SEQ ID NO:82 and SEQ ID NO:84; or (i) the heavy chain variable region (VH) has at least 90% sequence identity to a sequence selected from the group consisting of SEQ ID NO:85 and SEQ ID NO:87, and the light chain variable region (VL) has at least 90% sequence identity to a sequence selected from the group consisting of SEQ ID NO:86 and SEQ ID NO:88.

17. The isolated nucleic acid molecule of claim 10, wherein the immunobinder has at least 90% sequence identity to any of SEQ ID NO: 94 to SEQ ID NO: 121.

18. The isolated nucleic acid molecule of claim 10, wherein the immunobinder is an antibody.

19. The isolated nucleic acid molecule of claim 18, wherein the antibody is an scFv, Fab fragment, a Fab' fragment, a F(ab')$_2$ fragment, a Fd fragment, or a Fv fragment.

20. An expression vector comprising the nucleic acid molecule of claim 10.

21. An isolated host cell comprising the expression vector of claim 20.

* * * * *